(12) United States Patent
Cowan et al.

(10) Patent No.: US 10,039,889 B2
(45) Date of Patent: Aug. 7, 2018

(54) SYSTEM AND METHOD FOR SYRINGE FLUID FILL VERIFICATION

(71) Applicant: Bayer HealthCare LLC, Whippany, NJ (US)

(72) Inventors: Kevin P. Cowan, Allison Park, PA (US); Michael A. Spohn, Fenelton, PA (US); Michael McDermott, Pittsburgh, PA (US)

(*) Notice: Subject to any disclaimer, the term of this patent is extended or adjusted under 35 U.S.C. 154(b) by 0 days.

(21) Appl. No.: 15/634,513

(22) Filed: Jun. 27, 2017

(65) Prior Publication Data

US 2017/0290993 A1 Oct. 12, 2017

Related U.S. Application Data

(63) Continuation of application No. 15/249,667, filed on Aug. 29, 2016.
(Continued)

(51) Int. Cl.
*A61M 5/36* (2006.01)
*A61M 5/315* (2006.01)
(Continued)

(52) U.S. Cl.
CPC ............ *A61M 5/365* (2013.01); *A61M 5/007* (2013.01); *A61M 5/315* (2013.01); *G01F 23/02* (2013.01);
(Continued)

(58) Field of Classification Search
CPC .................. A61M 5/365; A61M 5/315; A61M 2205/3313; A61M 2205/6081; A61M 2205/587; A61M 2205/3306
See application file for complete search history.

(56) References Cited

U.S. PATENT DOCUMENTS 1,265,537 A * 5/1918 Shull ...................... G01F 19/00
 222/158
1,950,137 A 3/1934 Dowe
(Continued)

FOREIGN PATENT DOCUMENTS

CN 1876191 A 12/2006
EP 1932555 A1 6/2008
(Continued)

OTHER PUBLICATIONS

Braunstein, "Post-Claim Construction Declaration of Thomas H. Braunstein" (Redacted), from the lawsuit styled Liebel-Flarshiem Company v. Medrad, Inc., Civil Action No. C-1-98-858, in the United States District Court for the Southern District of Ohio, dated Nov. 19, 2001, pp. 1-11.
(Continued)

*Primary Examiner* — Bradley J Osinski
(74) *Attorney, Agent, or Firm* — Joseph L. Kent; David Schramm; James R. Stevenson

(57) ABSTRACT

A fluid injection system and a fluid verification system for confirming that a syringe, containing a fluid for injection, is fully filled with fluid and neither has free space (i.e., air) near the distal end thereof when the syringe is provided in an upright position nor contains air bubbles. Imaging processing techniques and systems are also provided to determine various injection parameters and to verify the type and certain properties of fluid that is present within a syringe.

30 Claims, 57 Drawing Sheets

Related U.S. Application Data

(60) Provisional application No. 62/211,462, filed on Aug. 28, 2015, provisional application No. 62/259,824, filed on Nov. 25, 2015.

(51) Int. Cl.
*A61M 5/00* (2006.01)
*G01F 23/02* (2006.01)

(52) U.S. Cl.
CPC ............... *A61M 2205/3306* (2013.01); *A61M 2205/3313* (2013.01); *A61M 2205/3368* (2013.01); *A61M 2205/505* (2013.01); *A61M 2205/587* (2013.01); *A61M 2205/6072* (2013.01); *A61M 2205/6081* (2013.01)

(56) References Cited

U.S. PATENT DOCUMENTS

| | | |
|---|---|---|
| 4,006,736 A | 2/1977 | Kranys et al. |
| 4,278,086 A | 7/1981 | Hodgins et al. |
| 4,452,251 A | 6/1984 | Heilman |
| 4,650,475 A | 3/1987 | Smith et al. |
| 4,677,980 A * | 7/1987 | Reilly .................. A61M 5/007 128/DIG. 1 |
| 4,978,335 A | 12/1990 | Arthur, III |
| 5,066,859 A | 11/1991 | Karkar et al. |
| 5,254,101 A | 10/1993 | Trombley, III |
| 5,383,858 A | 1/1995 | Reilly et al. |
| 5,461,239 A | 10/1995 | Atherton |
| 5,520,653 A | 5/1996 | Reilly et al. |
| 5,531,698 A | 7/1996 | Olsen |
| 5,662,612 A | 9/1997 | Niehoff |
| 5,741,232 A | 4/1998 | Reilly et al. |
| 5,806,519 A | 9/1998 | Evans, III et al. |
| 5,843,037 A | 12/1998 | Uber, III |
| 5,873,861 A | 2/1999 | Hitchins et al. |
| 5,916,197 A | 6/1999 | Reilly et al. |
| 5,928,197 A | 7/1999 | Niehoff |
| 5,944,694 A | 8/1999 | Hitchins et al. |
| 5,954,700 A | 9/1999 | Kovelman |
| 5,997,502 A | 12/1999 | Reilly et al. |
| 6,004,292 A | 12/1999 | Battiato et al. |
| 6,019,745 A | 2/2000 | Gray |
| 6,090,064 A | 7/2000 | Reilly et al. |
| 6,221,051 B1 | 4/2001 | Hjertman et al. |
| 6,290,678 B1 | 9/2001 | Aydelotte et al. |
| 6,322,535 B1 | 11/2001 | Hitchins et al. |
| 6,533,183 B2 | 3/2003 | Aasmul et al. |
| 6,652,489 B2 | 11/2003 | Trocki et al. |
| 6,726,657 B1 | 4/2004 | Dedig et al. |
| 6,733,478 B2 | 5/2004 | Reilly et al. |
| 6,743,202 B2 | 6/2004 | Hirschman et al. |
| 6,958,053 B1 | 10/2005 | Reilly |
| 7,018,363 B2 | 3/2006 | Cowan et al. |
| 7,462,166 B2 | 12/2008 | Kowan et al. |
| 7,549,977 B2 | 6/2009 | Schriver et al. |
| 7,553,294 B2 | 6/2009 | Lazzaro et al. |
| 7,666,169 B2 | 2/2010 | Cowan et al. |
| 7,682,345 B2 | 3/2010 | Savage |
| 8,173,995 B2 | 5/2012 | Ramakrishnan et al. |
| 8,403,909 B2 | 3/2013 | Spohn et al. |
| 9,173,995 B1 | 11/2015 | Tucker et al. |
| 9,199,033 B1 | 12/2015 | Cowan et al. |
| 9,474,857 B2 | 10/2016 | Riley et al. |
| 2001/0034506 A1 | 10/2001 | Hirschman et al. |
| 2002/0000471 A1 | 1/2002 | Aasmul et al. |
| 2002/0128606 A1 | 9/2002 | Cowan et al. |
| 2003/0060754 A1 | 3/2003 | Reilly et al. |
| 2003/0065287 A1 | 4/2003 | Spohn et al. |
| 2004/0064101 A1 | 4/2004 | Kowan et al. |
| 2005/0080384 A1 | 4/2005 | Green |
| 2006/0129104 A1 | 6/2006 | Cowan et al. |
| 2007/0203460 A1 | 8/2007 | Nemoto et al. |
| 2010/0013096 A1 | 1/2010 | Irumata et al. |
| 2011/0196312 A1 | 8/2011 | Devega |
| 2014/0249410 A1 | 9/2014 | Uber, III et al. |
| 2015/0105736 A1 | 4/2015 | Bisegna et al. |

FOREIGN PATENT DOCUMENTS

| | | |
|---|---|---|
| WO | 9425089 A1 | 11/1994 |
| WO | 9736635 A1 | 10/1997 |
| WO | 9800187 A1 | 1/1998 |
| WO | 9965548 A1 | 12/1999 |
| WO | 0108727 A1 | 2/2001 |
| WO | 0137903 A2 | 5/2001 |
| WO | 02056934 A2 | 7/2002 |
| WO | 02081011 A1 | 10/2002 |
| WO | 2012155035 A1 | 11/2012 |
| WO | 2015164783 A1 | 10/2015 |
| WO | 2016069711 A1 | 5/2016 |
| WO | 2016069714 A1 | 5/2016 |

OTHER PUBLICATIONS

Comar., "Oral Syringes", Jul. 2015.

"International Search Report and Written Opinion from corresponding PCT Application No. PCT/US2016/048445", dated Oct. 31, 2016.

International Search Report for Counterpart PCT Application No. PCT/US2002/01052 dated Jan. 29, 2003.

International Search Report for PCT Application No. PCT/US2002/010398 dated Aug. 1, 2002.

U.S. Appl. No. 09/365,285, filed Jul. 30, 1999; never published or patented.

Medtron; Ag., "Injektron CT 2, Computer Tomography", Dec. 2, 2004.

* cited by examiner

SYSTEM AND METHOD FOR SYRINGE FLUID FILL VERIFICATION

CROSS REFERENCE TO RELATED APPLICATIONS

This application is a continuation from U.S. application Ser. No. 15/249,667, filed Aug. 29, 2016 and claims priority to U.S. Provisional Patent Application Ser. Nos. 62/211,462, entitled "System and Method for Syringe Fluid Fill Verification and Image Recognition of Power Injector System Features", filed Aug. 28, 2015 and 62/259,824, entitled "System and Method for Syringe Fluid Fill Verification and Image Recognition of Power Injector System Features", filed Nov. 25, 2015, the contents of each of which are incorporated herein by reference.

BACKGROUND OF THE DISCLOSURE

Field

The present disclosure relates to systems and methods for verifying that a syringe is filled with fluid and, in particular, for determining the presence of such fluid based on an illuminated pattern produced by electromagnetic radiation projected through a portion of the filled syringe. In other aspects, the present disclosure relates to systems and methods for identifying the various features and properties of the fluid within the syringe.

Description of Related Art

In many medical, diagnostic, and therapeutic procedures, a medical practitioner, such as a physician, injects a patient with a medical fluid. In recent years, a number of injector-actuated syringes and powered injectors for pressurized injection of fluids, such as contrast media (often referred to simply as "contrast"), medicaments, or saline, have been developed for use in imaging procedures such as angiography, computed tomography, ultrasound, and magnetic resonance imaging. In general, these powered injectors are designed to deliver a preset amount of contrast or other fluid at a preset flow rate.

One of the issues involved in the injection of fluids into a patient using such automated injector systems is the possibility that air may be present in the syringe or fluid delivery system prior to injection. This issue is of particular concern in injection procedures for contrast medium, which are frequently colorless or only tinted to a limited degree. Further, imaging procedures are often performed under relatively low light levels to facilitate reading of x-rays, computer display screens, and the like. Accordingly, the concern that air in the syringe will not be identified prior to the injection procedure is increased. It is, therefore, desirable to readily detect if the syringe has not been filled with the fluid or is only partially filled with fluid (i.e., the syringe contains an amount of air) prior to the attempted injection.

Some solutions have been previously provided, in which the presence of liquid is indicated by an alteration of shape of an indicator pattern on the barrel of the syringe, as discussed, for example, in U.S. Pat. No. 4,452,251 to Heilman and U.S. Pat. No. 5,254,101 to Trombley, III, each of which are incorporated by reference herein in their entireties. However, systems and methods are needed to further aid in indicating the presence of liquid when the syringe is viewed from a distance or to allow verification of a filled syringe at a glance. Automated systems for verifying that the syringe is fully filled and does not include any air are also desirable.

In addition, since most medical fluids used with power injectors are clear, it is very difficult for a technician to quickly and easily distinguish between the fluid and air present in a translucent syringe. Accordingly, a need exists for a system used with a fluid injection device that is capable of differentiating between air and different types of fluid. In addition, automated systems that can determine various properties of the fluid, for example by analyzing properties and/or changes of the interaction between electromagnetic radiation with the contents of the syringe, and communicating those properties to the user, for example via a display screen, are also desirable.

SUMMARY

The systems and methods discussed herein provide an indication to the operator of a fluid injector of the presence of liquid in a syringe when the syringe is viewed from a distance or to allow verification of a filled syringe at a glance. In addition, automated systems for verifying that the syringe is fully filled and does not include any air are also provided. Such systems allow for the differentiation between air and/or different types of fluids contained within a syringe of the fluid injector, thereby enhancing safety by preventing air injections as well as facilitating improved workflow by preventing technicians from mixing up the fluid types. Further, in certain aspects the system may determine one or more properties of the fluid within the syringe and/or the injection procedure.

According to one aspect of the present disclosure, provided is a syringe comprising: a syringe barrel comprising a proximal end and a distal end comprising an angled surface; and a plunger slideably disposed in the syringe barrel and configured to advance through the barrel to expel a fluid therefrom. The plunger comprises a transparent or translucent material configured to transmit electromagnetic radiation therethrough such that an illuminated identification pattern is formed at a predetermined portion of the distal end of the syringe barrel when the syringe is filled with the fluid.

In one aspect, the syringe barrel may be shaped such that when an interior volume of the syringe barrel is completely or partially filled with air, at least one property of the illuminated identification pattern is different compared to when the syringe is completely filled with the fluid. The at least one property may comprise at least one of presence of, size, shape, and brightness of the illuminated identification pattern.

In one aspect, the illuminated identification pattern may not be visible when a percentage of a volume of air present in the distal end of the syringe is greater than about 15% of the volume of the distal end of the syringe having the angled surface. In another aspect, the illuminated identification pattern may be visible to an observer or to a sensor when the syringe is viewed from a side, at a straight-on orientation, or a tilted forward or tilted backward orientation. The angled surface of the distal end of the syringe barrel may have an angle of about 30 degrees to 60 degrees relative to a longitudinal axis of the syringe.

In one aspect, the electromagnetic radiation source may comprise a light bulb, an LED bulb, a photon emitter, an infrared emitter, a laser, or ambient light. In another aspect, at least one reference line or marking may be formed on a distal end of the syringe barrel and extend around a circumference of the distal end of the syringe barrel. The at least one reference line or marking may be formed on the barrel of the syringe by at least one of printing, overmolding, and etching. In one aspect, a first reference line or marking of the at least one reference line or marking is configured to align with a first predetermined portion of the illuminated identification pattern if a first fluid is present within the syringe and a second reference line or marking is configured to align with a second predetermined portion of the illuminated identification pattern if a second fluid is present within the syringe. The at least one reference line or marking may be configured to align with a predetermined portion of the illuminated identification pattern if a first fluid is present within the syringe and may be configured to be positioned away from the illuminated identification pattern if a second fluid is present within the syringe.

According to another aspect of the present disclosure, provided is a system for indicating whether a syringe is ready for use in injecting a fluid therein into a patient. The system comprises: a syringe comprising a barrel comprising a distal end having an angled surface and defining an interior volume configured to receive the fluid; and an electromagnetic radiation source positioned to emit electromagnetic radiation through at least a portion of the syringe. The syringe is shaped such that, when the syringe is filled with the fluid, at least a portion of the electromagnetic radiation is affected by an interaction of the electromagnetic radiation with at least one interface associated with the fluid and the syringe to form an illuminated identification pattern indicative of contents of the syringe on a predetermined portion of the syringe.

In one aspect, the syringe may be shaped such that when the interior volume is completely or partially filled with air, at least one property of the illuminated identification pattern is different compared to when the interior volume is completely filled with the fluid. The at least one property may comprise at least one of presence of, size, shape, and brightness of the illuminated identification pattern. The illuminated identification pattern may not be visible when a percentage of a volume of air present in the distal end of the syringe is greater than about 15% of the volume of the distal end of the syringe having the angled surface.

In another aspect, the system may further include at least one sensor configured to measure the at least one property of the illuminated identification pattern when present. The at least one sensor may comprise at least one of an imaging sensor, an optical sensor, an electromagnetic radiation detector, or a digital camera. In another aspect, the system may also include a fluid injector configured to interface with the syringe to eject the fluid from the syringe. The fluid injector may comprise a controller configured to receive a confirmation signal from the at least one sensor when the measurement of the at least one property of the illuminated identification pattern indicates that the syringe is substantially filled with fluid, and the controller is configured to actuate the injector to perform an injection when the confirmation signal is received.

In one aspect, the illuminated identification pattern may be visible to an observer or to a sensor when the syringe is viewed from a side, at a straight-on orientation, or at a tilted forward or tilted backward orientation. In another aspect, the illuminated identification pattern may comprise an annular shape extending about at least a portion of the distal end of the syringe barrel. In yet another aspect, the angled surface of the distal end of the barrel may have an angle of about 30 degrees to 60 degrees relative to a longitudinal axis of the syringe. In one aspect, the electromagnetic radiation source may comprise a light bulb, an LED bulb, a photon emitter, an infrared emitter, a laser, or ambient light.

In certain aspects, the syringe may further comprise a plunger, and the electromagnetic radiation source is positioned to project at least a portion of the electromagnetic radiation to reflect off or transmit through the plunger. In one example, at least a portion of the plunger comprises a transparent or translucent material. In another example, at least a portion of the plunger comprises a colored material.

According to another aspect of the present disclosure, provided is a method for syringe fluid fill verification comprising: emitting electromagnetic radiation through at least a portion of a syringe; identifying whether at least a portion of the electromagnetic radiation produces an illuminated identification pattern on a predetermined portion of the syringe; and determining contents of the syringe based on at least one property of the illuminated identification pattern.

In one aspect, the at least one property may be at least one of a presence of the illuminated identification pattern, a size of the illuminated identification pattern, a shape of the illuminated identification pattern, and a brightness of the illuminated identification pattern. In another aspect, the step of: identifying whether the at least a portion of the electromagnetic radiation produces an illuminated identification pattern may comprise: measuring the at least one property of the illuminated identification pattern by at least one sensor associated with the syringe; and receiving a confirmation signal from the at least one sensor indicating a value for the at least one property of the illuminated identification pattern. In an additional aspect, emitting electromagnetic radiation through at least the portion of the syringe may comprises emitting electromagnetic radiation through a syringe plunger, at least a portion of which comprises a transparent or translucent material.

According to another aspect of the present disclosure, provided is a fluid injection system that comprises: a fluid injector; at least one syringe operatively engaged with the fluid injector; and an electromagnetic radiation source. The at least one syringe comprises a barrel comprising a distal end having an angled surface and defining an interior volume configured to receive a fluid. The electromagnetic radiation source is positioned relative to the at least one syringe to emit electromagnetic radiation through at least a portion of the at least one syringe such that, when the syringe is filled with the fluid, at least a portion of the electromagnetic radiation is affected by an interaction of the electromagnetic radiation with at least one interface associated with the fluid and the syringe to form an illuminated identification pattern indicative of contents of the at least one syringe on a predetermined portion of the at least one syringe. The fluid injection system also comprises: an image capture device positioned to capture an image of the illuminated identification pattern; and at least one computing device in communication with the image capture device and the fluid injector. The at least one computing device comprises at least one processor configured to: determine a distance from a bottom to a top of the illuminated identification pattern in the image of the illuminated identification pattern; compare the distance from the bottom to the top of the illuminated identification pattern to at least one predetermined distance; and based on the comparison of the distance from the bottom to the top of the illuminated identification pattern to the at least one predetermined distance, at least one of i) display on a display device in communication with the at least one processor an indication of a characteristic of the at least one syringe; ii) enable the fluid injector to perform a function; and iii) disable the fluid injector from performing an action.

In one aspect, determining a distance from the bottom to the top of the illuminated identification pattern may comprise determining a bottom edge of the illuminated identification pattern and determining a top edge of the illuminated identification pattern. The bottom edge and the top edge of the illuminated identification pattern may be determined by determining a change in contrast between neighboring pixels in the image of the illuminated identification pattern.

In another aspect, the characteristic of the at least one syringe may be the presence of air in the at least one syringe and the at least one processor may be further configured to, if the distance from the bottom to the top of the illuminated identification pattern is less than the at least one predetermined distance, provide an indication that air is present in the at least one syringe and disable the fluid injector from conducting an injection procedure. In addition, the at least one processor may be configured to determine a size of the at least one syringe prior to determining the distance from the bottom to the top of the illuminated identification pattern by matching a first template of a known illuminated identification pattern for a syringe having a first size with the image of the illuminated identification pattern. In one aspect, the at least one processor may be further configured to provide an indication that the at least one syringe has the first size if the first template matches the image of the illuminated identification pattern. The at least one processor may be further configured to match a second template of a known illuminated identification pattern for a syringe having a second size with the image of the illuminated identification pattern if the first template does not match the image of the illuminated identification pattern. The at least one processor may be further configured to provide an indication that the at least one syringe has the second size if the second template matches the image of the illuminated identification pattern.

In another aspect, the characteristic of the at least one syringe may be contents of the at least one syringe. The at least one predetermined distance may comprise a first predetermined distance indicative of a first fluid as the contents contained in the at least one syringe and a second predetermined distance indicative of a second fluid as the contents contained within the at least one syringe. If the distance from the bottom to the top of the illuminated identification pattern corresponds to the first predetermined distance, an indication that the first fluid is contained in the at least one syringe may be provided, and, if the distance from the bottom to the top of the illuminated identification pattern corresponds to the second predetermined distance, an indication that the second fluid is contained in the at least one syringe may be provided. If the at least one processor determines that the first fluid is present in the at least one syringe, a color of the electromagnetic radiation forming the illuminated identification pattern may be set to a first color and, if the at least one processor determines that the second fluid is present in the at least one syringe, the color of the electromagnetic radiation forming the illuminated identification pattern may be set to a second color different from the first color.

In other aspects, the at least one syringe may further comprise a plunger, and the electromagnetic radiation source may be positioned to project at least some of the electromagnetic radiation through the plunger. In such aspects, the plunger may comprise a transparent or translucent material. In still other aspects, the electromagnetic radiation source may be positioned such that the electromagnetic radiation reflects from a distal surface of the plunger through the barrel. In such aspects, the plunger may comprise an opaque, colored material. In other aspects, the electromagnetic radiation source may be positioned adjacent to the barrel of the at least one syringe and the electromagnetic radiation is reflected from a mirror located near the distal end of the barrel and directed toward a distal surface of the plunger such that the electromagnetic radiation reflects from the plunger through the barrel.

According to an additional aspect of the present disclosure, provided is a fluid injection system comprising: a fluid injector; at least one syringe operatively engaged with the fluid injector, the syringe comprising a barrel comprising a distal end having an angled surface and defining an interior volume configured to receive the fluid; an electromagnetic radiation source positioned relative to the at least one syringe to emit electromagnetic radiation through at least a portion of the at least one syringe such that, when the syringe is filled with the fluid, at least a portion of the electromagnetic radiation is affected by an interaction of the electromagnetic radiation with at least one interface associated with the fluid and the syringe to form an illuminated identification pattern indicative of contents of the at least one syringe on a predetermined portion of the at least one syringe; an image capture device positioned to capture an image of the illuminated identification pattern; and at least one computing device in communication with the fluid injector and the image capture device. The at least one computing device comprises at least one processor configured to: determine a distance from a bottom to a top of the illuminated identification pattern in the image of the illuminated identification pattern; compare the distance from the bottom to the top of the illuminated identification pattern to a predetermined distance; and if the distance from the bottom to the top of the illuminated identification pattern is less than the predetermined distance, provide an indication that air is present in the at least one syringe and disable the fluid injector from conducting an injection procedure.

In one aspect, determining a distance from the bottom to the top of the illuminated identification pattern may comprise determining a bottom edge of the illuminated identification pattern and determining a top edge of the illuminated identification pattern. The bottom edge and the top edge of the illuminated identification pattern may be determined by determining a change in contrast between neighboring pixels in the image of the illuminated identification pattern.

In another aspect, the at least one processor may be configured to determine a size of the at least one syringe prior to determining the distance from the bottom to the top of the illuminated identification pattern by matching a first template of a known illuminated identification pattern for a syringe having a first size with the image of the illuminated identification pattern. The at least one processor may be further configured to provide an indication that the at least one syringe has the first size if the first template matches the image of the illuminated identification pattern. The at least one processor may be further configured to match a second template of a known illuminated identification pattern for a syringe having a second size with the image of the illuminated identification pattern if the first template does not match the image of the illuminated identification pattern. The at least one processor may be further configured to provide an indication that the at least one syringe has the second size if the second template matches the image of the illuminated identification pattern.

According to another aspect of the present disclosure, provided is a fluid injection system that comprises: a fluid injector; at least one syringe operatively engaged with the fluid injector and configured to be illuminated with an electromagnetic radiation source to illuminate fluid contained therein; a sensor positioned to capture an image of the illuminated fluid; and at least one computing device in communication with the fluid injector and the sensor. The at least one computing device comprises at least one processor configured to: obtain from the sensor the image of the illuminated fluid; determine, based on the image of the illuminated fluid, at least one of: a type of the fluid contained within the at least one syringe; and whether air is contained within the at least one syringe; and automatically display on a display device in communication with the at least one processor one of: an indication of the type of the fluid contained within the at least one syringe; and an indication that air is contained within the at least one syringe.

In certain aspects, the at least one processor may be configured to disable the fluid injector from conducting an injection procedure if air is determined to be contained within the at least one syringe. Brightness measurements may be performed in a region of interest in the image of the illuminated fluid are utilized to determine at least one of: type of fluid contained within the at least one syringe; and whether air is contained within the at least one syringe.

According to another aspect of the present disclosure, provided is a fluid injection system comprising: a fluid injector; a syringe operatively engaged with the fluid injector; an image capture device; and at least one computing device in communication with the fluid injector and the image capture device. The syringe comprises a barrel and defining an interior volume and at least one feature provided on the barrel of the syringe. The at least one feature has a different appearance when viewed through different types of fluid contained within the syringe. The image capture device is positioned to capture an image of the at least one feature through a content of the syringe. The at least one computing device comprises at least one processor configured to: obtain the image of the at least one feature through the fluid contained within the syringe; determine, based on the image of the at least one feature, an appearance of the at least one feature; compare the determined appearance with templates of appearances of the at least one feature when viewed through different types of fluids; and automatically display on a display device in communication with the at least one processor an indication of a characteristic of the syringe based on the comparison.

In one aspect, the at least one feature may be formed on the barrel of the syringe by at least one of printing, overmolding, and etching. In another aspect, the at least one feature may be a fluid dot, a line, a series of lines, or any combination thereof. The appearance of the at least one feature may comprise at least one of a shape of the at least one feature and an orientation of the at least one feature.

In one aspect, the characteristic of the syringe may be the presence of air in the syringe and the at least one processor may be further configured to, if the determined appearance matches one of the templates of appearances of the at least one feature when viewed through air, provide an indication that air is present in the at least one syringe and disable the fluid injector from conducting an injection procedure.

In another aspect, the characteristic of the at least one syringe may be the contents of the at least one syringe and the at least one processor may be further configured to, if the determined appearance matches one of the templates of appearances of the at least one feature when viewed through a first fluid, provide an indication that the first fluid is present within the syringe. In one aspect, the at least one processor may be further configured to, if the determined appearance matches one of the templates of appearances of the at least one feature when viewed through a second fluid, provide an indication that the second fluid is present within the syringe.

According to another aspect of the present disclosure, provided is a fluid injection system comprising: a fluid injector; a syringe operatively engaged with the fluid injector in a vertical orientation, the syringe comprising a barrel and defining an interior volume configured to receive a fluid and at least one object having a density that is different than the density of the fluid such that the at least one object floats if the fluid is present within the barrel; an image capture device positioned to capture an image of the barrel; and at least one computing device in communication with the fluid injector and the image capture device. The at least one computing device comprises at least one processor configured to: obtain the image of the barrel; determine, based on the image of the barrel, a position of the at least one object within the barrel and thus whether the barrel is one of (i) filled completely with the fluid and (ii) filled at least partially with air; provide an indication, based on the determination, that air is present in the syringe based on the position of the at least one object; and disable the fluid injector from conducting an injection procedure.

According to still another aspect of the present disclosure, provided is a fluid injection system comprising: a fluid injector; a syringe operatively engaged with the fluid injector; an image capture device positioned to capture an image of at least a portion of the syringe; and at least one computing device in communication with the fluid injector and the image capture device. The at least one computing device comprises at least one processor configured to: obtain the image of at least a portion of the syringe; determine, based on at least a portion of the syringe, at least one characteristic of an injection procedure performed by the fluid injector; and adjust the at least one characteristic of the injection procedure performed by the fluid injector to ensure that fluid is delivered to a predetermined region of interest in a body of a patient at a particular time such that viable images are produced during an imaging procedure.

In one aspect, the at least one characteristic of the injection procedure may be at least one of flow rate, volume of fluid remaining within the syringe, and capacitance measurement of the syringe.

These and other features and characteristics of the systems and/or devices of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the systems and/or devices of the present disclosure. As used in the specification and claims, the singular form of "a", "an", and "the" include plural referents unless the context clearly dictates otherwise.

DETAILED DESCRIPTION

Figure 1:
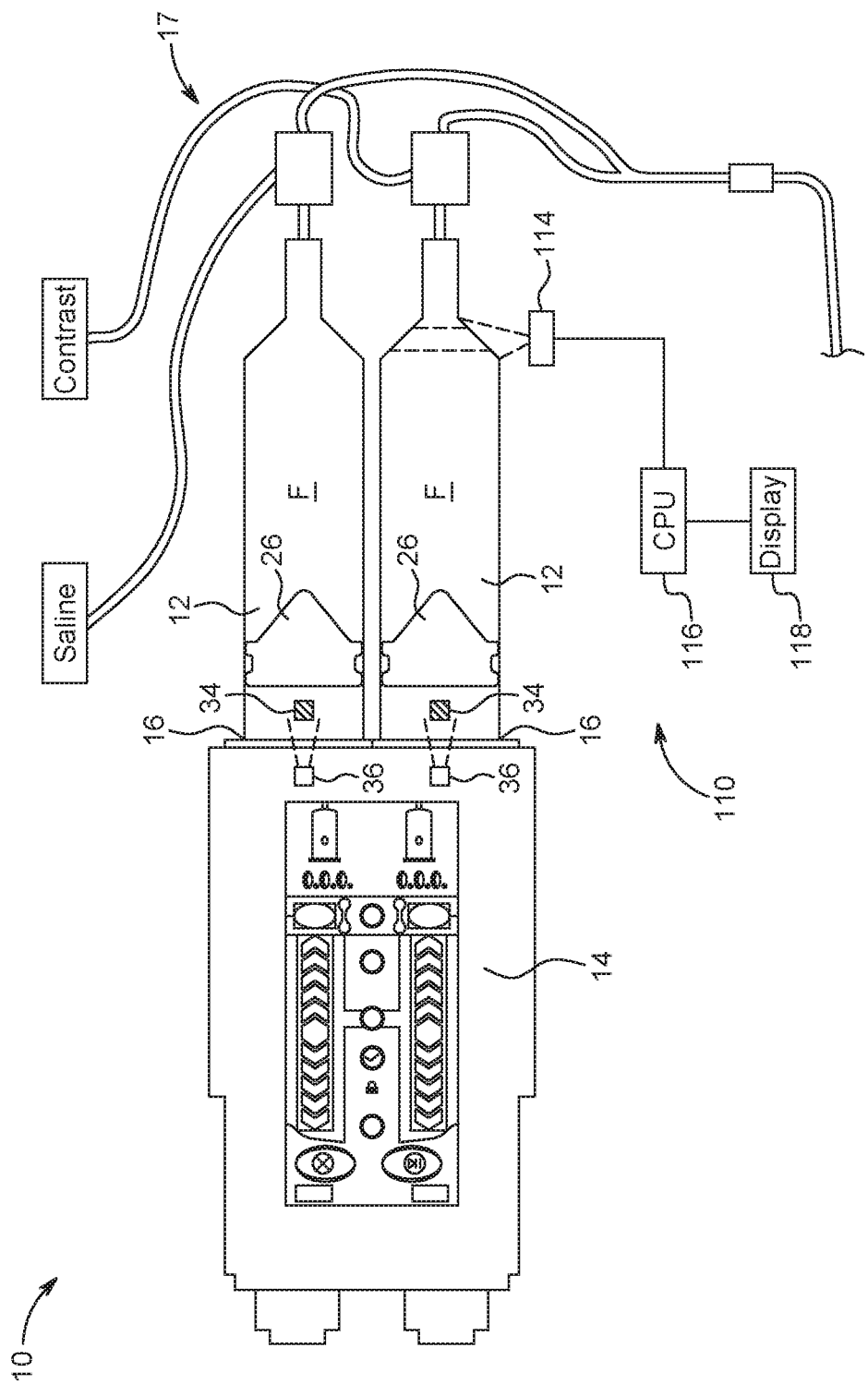
FIG. 1 is a schematic drawing of a fluid injector and fluid verification system, according to an aspect of the disclosure.

For purposes of the description herein, the terms "upper", "lower", "right", "left", "vertical", "horizontal", "top", "bottom", "lateral", "longitudinal", and derivatives thereof shall relate to the disclosure as it is oriented in the drawing figures. When used in relation to a syringe, the term "proximal" refers to the portion of a syringe nearest to an injector, when a syringe is connected to an injector. The term "distal" refers to the portion of a syringe farthest away from an injector. It is to be understood, however, that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the embodiments disclosed herein are not to be considered as limiting.

One aspect of the present disclosure is directed to a fluid injection system and a fluid verification system for confirming, using image processing techniques, that a syringe, containing a fluid for injection, is fully filled with fluid and neither has free space (i.e., air) near the distal end thereof when the syringe is provided in an upright position nor contains air bubbles. The present disclosure is also generally directed to using imaging processing techniques to determine various injection parameters to verify the type and certain properties of fluid that is present within a syringe.

As used herein, fluid and/or medical fluid refer to liquid substances or solutions, such as, but not limited to, contrast, saline, and therapeutic liquids. In certain aspects, the fluid verification system is configured to emit electromagnetic radiation, such as a visible or infrared light, through at least a portion of the syringe barrel. Electromagnetic radiation refers to radiant energy that propagates through space in the form of one or more electromagnetic waves. Electromagnetic radiation can be visible (e.g. having a wavelength of between approximately 400 nm to 700 nm) or non-visible to the human eye, as is the case, for example, with x-rays, radio rays, infrared radiation, and ultraviolet radiation. In addition, as used herein electromagnetic radiation may be ambient light. When the syringe is fully filled with a fluid, the electromagnetic radiation is refracted by the fluid and/or the syringe barrel to illuminate the distal end of the syringe to provide a distinctive identification pattern. The illuminated area defining the identification pattern on the distal end of the syringe is referred to herein as a halo. As used herein the term "halo" includes an illuminated identification pattern that includes a circular colored/illuminated ring around or a conical sub-portion of the distal portion of the conical distal end of the syringe. This halo may be readily identified by an operator when viewed at a straight-on, true side view, or slightly elevated position. In one example, this straight-on or true side view may be in a plane generally parallel to a plane extending through a central axis of the syringe and generally along a plane extending through a distal end of the syringe. Illuminating the syringe in the manner described herein may also cause any air bubbles present along the sidewalls of the syringe barrel to be illuminated, thereby allowing an operator or sensor to more easily identify the presence of such air bubbles.

In some aspects, one or more sensors may be configured to capture images of the distal end of the syringe, for example to detect the halo pattern via automated image processing techniques. If the syringe is entirely filled with fluid, a distinctly observable halo, for example in a form of a lighted band on at least a portion of the distal end of the syringe, is illuminated as an identification that the syringe is fully filled with fluid. If the syringe is not entirely filled with fluid, such as when the syringe is completely or partially filled with air, the size and/or brightness of the halo is substantially reduced or disappears. As used herein, fluid refers to a medical grade liquid configured to be delivered to a patient, such as saline or various types and concentrations of contrast, as opposed to air or other gases.

I. Generation of Illuminated Identification Pattern

A. Exemplary Fluid Injection System

With reference to FIG. 1, a fluid injector 10, such as an automated or powered fluid injector, is illustrated, which is adapted to interface with and actuate one or more syringes 12, which may be filed with a fluid F, such as contrast media, saline solution, or any desired medical fluid. The fluid injector 10 can be used during an angiographic, computed tomography (CT), magnetic resonance imaging (MRI), molecular imaging, or other medical procedure to inject contrast and/or a common flushing agent, such as saline, into the body of a patient. In some examples, the fluid injector 10 can be at least a dual-syringe injector, wherein the two fluid delivery syringes 12 are oriented in a side-by-side or other spatial relationship and are separately actuated by respective linear actuators or piston elements associated with the injector 10.

The injector 10 can be enclosed within a housing 14 formed from a suitable structural material, such as plastic and/or metal. The housing 14 can be formed in various shapes and sizes depending on the desired application. For example, the injector 10 can be a free-standing structure configured to be placed on the floor or may be configured for placement on a suitable table or support frame. The injector 10 includes one or more syringe ports 16 for connecting to the proximal ends of the one or more syringes 12 and to connect plungers 26 to respective piston elements. The syringe ports 16 are generally located on a side of the housing 14, as shown, for example, in FIG. 1. The housing 14 can be rotatable to direct the syringe port 16 and syringe 12 extending therefrom in the vertical, horizontal, or downward facing direction. In some examples, the syringe 12 can include at least one identification tag 34, such as a label or bar code, including information about the syringe dimensions, volume, pressure tolerances, and/or information about the fluid contained in the syringe 12. The at least one identification tag 34 can be read by a sensor 36, positioned on or recessed in the side of the housing 14 or within at least a portion of the inner surface of the at least one syringe port 16 of the injector 10.

A fluid path set 17 can be interfaced with the syringe 12 for delivering one or more fluids from the syringe 12 to a catheter (not shown) inserted into a patient at a vascular access site. For example, a flow of saline solution from a first syringe 12 and contrast from a second syringe 12 may be regulated by a fluid control module (not shown) associated with the injector 10. The fluid control module operably controls injection rates, pressures, valves and flow regulating structures, such as pistons or linear actuators, to regulate the delivery of the saline solution and/or contrast to the patient based on user selected injection parameters, such as injection flow rate, duration, total injection volume, and ratio of contrast media and saline, which may be programmed or otherwise entered into the injector fluid control module.

A suitable front-loading fluid injector for use with the above-described system is disclosed in U.S. Pat. No. 5,383,858 to Reilly et al., which is incorporated by reference in its entirety. Other exemplary multi-fluid delivery systems and components are found in U.S. Pat. No. 7,553,294 to Lazzaro et al.; U.S. Pat. Nos. 7,666,169 and 9,199,033 to Cowan et al.; U.S. Pat. No. 9,173,995 to Tucker et al.; PCT Publication No. WO 2012/155035 to Shearer et al.; and U.S. Patent Application Publication No. 2014/0027009 to Riley et al., all of which are assigned to the assignee of the present application, and the disclosures of which are incorporated herein by reference.

B. Exemplary Syringe for Use with the Fluid Injection Device

1. Details of Syringe Body

Figure 2:
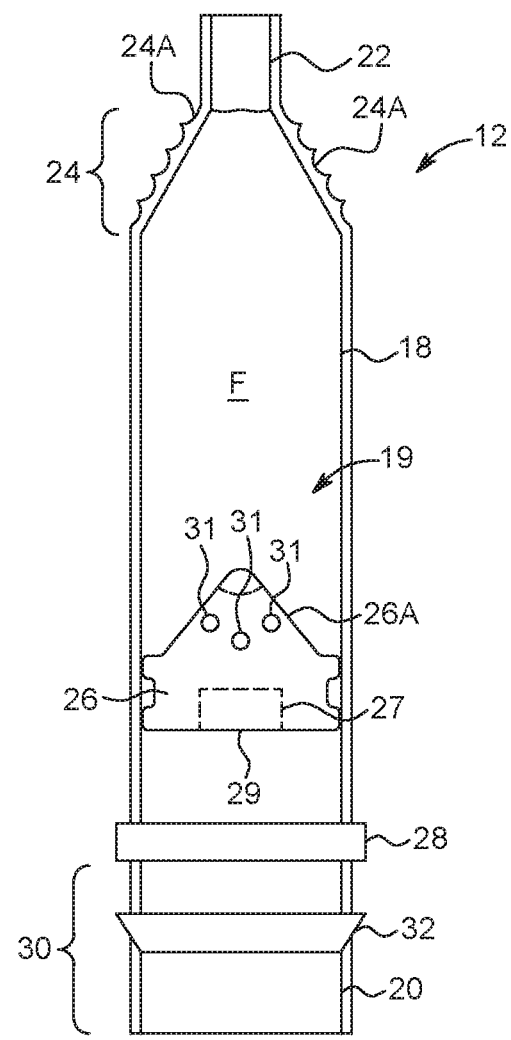
FIG. 2 is a schematic drawing of a syringe according to an aspect of the disclosure for use with the injector of FIG. 1.

Having described the general structure and function of the fluid injector 10, a syringe 12 configured for connection to the injector 10 and containing a fluid F will now be discussed in detail. With reference to FIG. 2, the syringe 12 comprises a substantially cylindrical barrel 18 formed from glass or a suitable medical-grade plastic and defining an interior volume 19. For example, the barrel 18 can be formed from medical grade polyethylene terephthalate (PET) or other medical-grade plastic material. The barrel 18 has a proximal end 20 and a tapered, conical distal end 24 extending to a nozzle 22. The barrel 18 can be formed from a transparent or translucent material so that a user or system operator can observe fluid F contained therein and, as is discussed herein, when used with a fluid verification system, can identify the halo on the distal end 24 of the barrel 18. In other examples, only the distal end 24 of the barrel 18 is transparent or translucent, and other portions of the barrel 18 are formed from an opaque reflective material for increasing transmission of light through the barrel 18. In some aspects, a shield (not shown) may be provided around an outer circumference of the barrel 18. The shield may be formed from an opaque reflective material for increasing the transmission of light through the barrel 18. The fluid F generally has an index of refraction greater than that of air and may be different from the material of the barrel 18 and, therefore, alters the path of electromagnetic radiation, such as visible light, traveling through the barrel 18 of the syringe 12. For example, the refractive index of air is about 1, the refractive index of saline is about 1.34, the refractive index of contrast is about 1.46, and the refractive index of PET is about 1.57. Without intending to be bound by theory, a travel path of electromagnetic radiation is governed by the reflection and refraction characteristics of the media through which electromagnetic radiation travels.

Figure 3A:
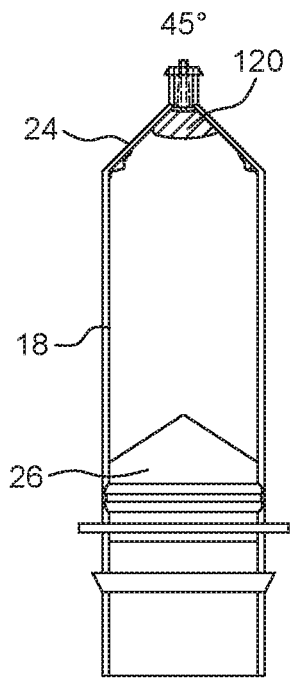
FIGS. 3A-3D are schematic drawings of syringes having various shaped distal ends along with the appearance of an illuminated identification pattern, according to an aspect of the present disclosure.
Figure 3B:
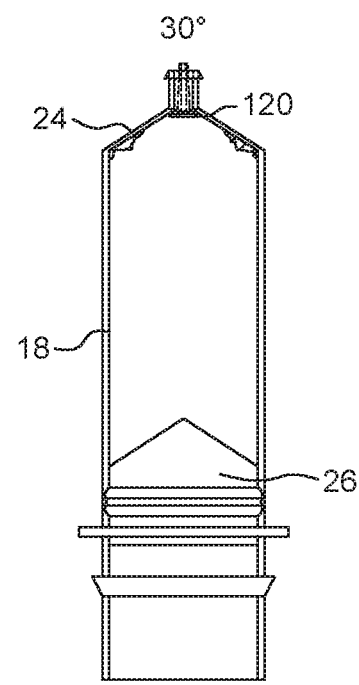
Figure 3C:
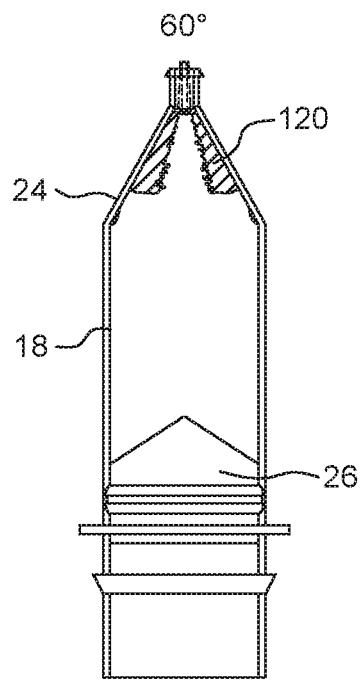
Figure 3D:
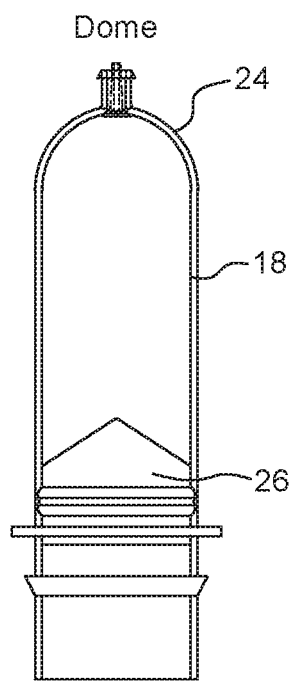

The appearance of an illuminated area or halo 120 is determined, at least in part, based on the angle and/or shape of the tapered distal end 24 of the barrel 18 as shown in FIGS. 3A-3D. In some aspects, the tapered distal end 24 of the barrel 18 may be tapered at an angle ranging from 30 degrees to 60 degrees, and in other aspects from 40 degrees to 50 degrees relative to the horizontal or to a latitudinal or radial axis extending through the syringe 12. In one example, the angle of the tapered distal end 24 of the barrel 18 is about 45 degrees relative to the horizontal (see FIG. 3A). There are also high and low thresholds where the reflected illuminated area or halo no longer becomes visible. Accordingly, changing the angle and/or shape of the tapered distal end 24 of the barrel 18 may have an impact on the size and visualization of the halo 120. For example, as the angle of the tapered distal end 24 of the barrel increases, the size of the visualized halo increases (see FIG. 3C illustrating a syringe having a tapered distal end 24 with an angle of 60 degrees relative to the horizontal). However, the brightness of the halo generally decreases with such an increase of the angle. This may be compensated for by increasing the intensity of the electromagnetic radiation from the source used to generate the halo. In another example, as the angle of the tapered distal end 24 of the barrel 18 decreases, the size of the halo 120 also decreases as shown in FIG. 3B. Finally, if the distal end 24 of the syringe does not have any angled surfaces, such as the dome shaped syringe shown in FIG. 3D, no halo 120 is generated. The specific details of the manner in which the halo 120 is generated at the distal end of the syringe 12 are provided herein.

Figure 4A:
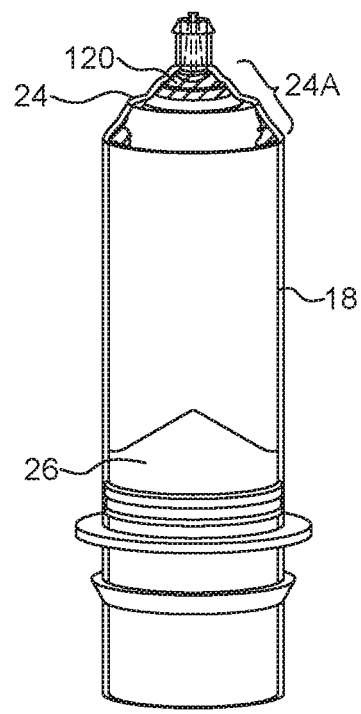
FIGS. 4A-4C are schematic drawings of syringes having various features provided on a distal end thereof to change shape and/or size of the illuminated identification pattern.
Figure 4B:
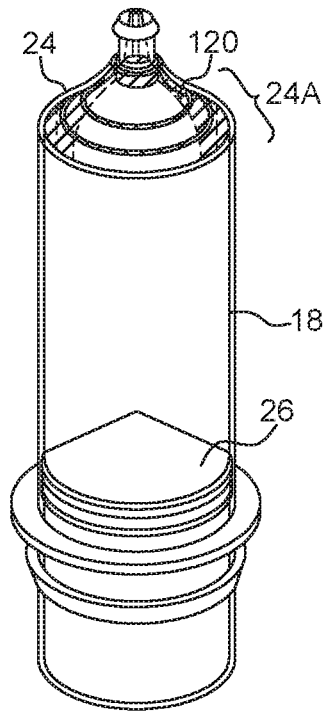
Figure 4C:
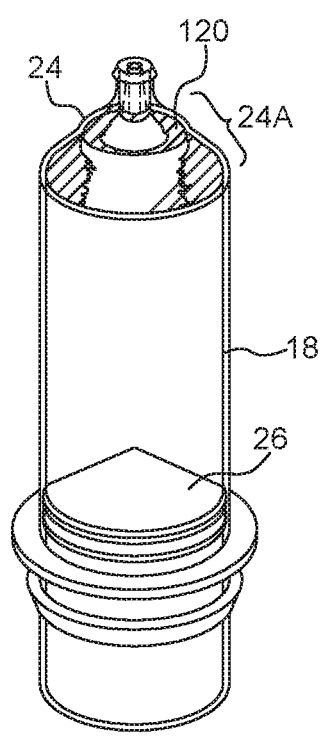

In some examples, at least a portion of the distal end 24 of the syringe barrel 18 can include one or more elements configured to accentuate the appearance of the halo 120. The one or more elements may be in the form of scallops or ridges 24A extending circumferentially around an outer surface of the distal end 24 of the barrel 18. The scallops or ridges 24A can be positioned to refract at least a portion of the halo 120, making it visible over a range of viewing angles and user positions. The scallops or ridges 24A can be used to make multi-part lenses such as a Fresnel lens. Lenses of this type can allow light passing through the portion of the syringe 12 where the halo 120 is visualized to be redirected into a more direct path toward a detector or viewer. Such lenses can also be used to transmit light over a farther distance and appear brighter at a larger number of viewing angles. Additionally, the scallops or ridges 24A allow for enhanced visualization of the halo 120 or other features within the syringe 12. The geometry of the ridges 24A may be determined by the internal reflection of the light and the corresponding combination or convergence of rays back at the eye of the viewer. With reference to FIGS. 4A-4C, different arrangements of the scallops or ridges 24A at the distal end 24 leading to different shapes or sizes of the produced halo 120 are illustrated.

Returning to FIG. 2, in some examples, an annular flange, often referred to as a drip flange 28, extends radially outward from the syringe barrel 18 at a position near the proximal end 20 thereof. When the syringe 12 is inserted in the injector 10 (shown in FIG. 1), the drip flange 28 is positioned relative to a distal opening of the syringe port 16 (shown in FIG. 1) to prevent excess fluid expelled from the syringe 12 from entering the port 16. The portion of the syringe barrel 18 between the drip flange 28 and the proximal end 20 of the barrel 18, referred to herein as the insertion portion 30, is sized and adapted to be inserted in the syringe port 16 of the injector 10. Accordingly, in some examples, the insertion portion 30 of the barrel 18 includes one or more locking structures, such as a locking flange 32, extending radially outward from the barrel 18. The locking flange 32 can be adapted to form a locking engagement with corresponding protrusions or locking structures in syringe port 16 for releasably maintaining syringe 12 in syringe port 16 while injector 10 is in use. Alternatively, insertion portion 30 can include one or more latches, locking mechanisms, or radially extending ribs for connection to corresponding portions of syringe port 16.

Exemplary syringes suitable for use with the injector 10 depicted in FIG. 1, and which can be adopted for use with a fluid verification system, are described in U.S. Pat. No. 5,383,858 to Reilly et al.; U.S. Pat. Nos. 7,666,169 and 9,199,033 to Cowan et al.; and U.S. Pat. No. 9,173,995 to Tucker et al. Additional exemplary syringes are disclosed in U.S. Pat. No. 6,322,535 to Hitchins et al. and U.S. Pat. No. 6,652,489 to Trocki et al. The disclosures of each of these references are incorporated by reference in their entireties.

2. Examples of Plungers for Use with Exemplary Syringe

With continued reference to FIG. 2, the proximal end 20 of the syringe barrel 18 can be sealed with a plunger or plunger cover 26 which is slidably disposed within the syringe barrel 18. The plunger or plunger cover 26 may have a distal surface 26A. The plunger or plunger cover 26 forms a liquid-tight seal against the sidewall of the barrel 18 as it is advanced or withdrawn therethrough. The plunger or plunger cover 26 can include an interior cavity 27 and proximal opening 29 configured to receive and engage a distal end of a piston rod (not shown) extending from the injector 10 (shown in FIG. 1). The piston rod is advanced or retracted through the syringe barrel 18 by the injector 10 to drive the plunger or plunger cover 26 through the interior 19 of the syringe barrel 18 to expel fluid F therefrom or deliver fluid F into the syringe barrel 18.

In some examples, the plunger or plunger cover 26 is at least partially formed from a substantially transparent or translucent material and configured to permit electromagnetic radiation, such as visible light, ambient light, infrared light, or ultraviolet light, to pass through or be emitted from a portion of the plunger or plunger cover 26. For example, the plunger or plunger cover 26 can include a transparent or translucent central portion enclosed by an annular elastomeric ring that provides the seal between the plunger cover 26 and the inner surface of the barrel 18. The emitted electromagnetic radiation radiates, propagates, or travels within and/or through the syringe barrel 18 in a substantially axial direction toward the distal end 24 of the syringe barrel 18, while other electromagnetic radiation is emitted in a non-axial direction but at least a portion of the electromagnetic radiation is reflected off of the interior surface of the syringe barrel 18 toward the distal end 24. It also propagates from the plunger or plunger cover 26 in a non-axial direction with a portion thereof reflecting off the sidewall of the syringe barrel 18 toward the distal end 24 of the syringe 12. Electromagnetic radiation beams can be scattered when passing through the transparent or translucent material of the plunger or plunger cover 26, which contributes to the appearance of the halo. While the plunger or plunger cover 26 can be clear, or tinted white, certain more noticeable colors can be useful in particular applications. For example, the plunger material can be tinted a conspicuous color, such as bright red or bright green, to impart a color to the halo. Imparting a bright, noticeable color to the halo assists the system operator in recognizing the halo, when present. For example, the plunger or plunger cover 26 can be tinted green or blue to increase visibility and as confirmation that the syringe 12 is ready for use (e.g., green is often understood to signify a "begin" or "go" state of readiness). Alternatively, the electromagnetic radiation passing through the plunger or plunger cover 26 may have a color, such as a red, green, blue, or other color from a light source to define a colored halo.

Alternatively, or in addition to including transparent or translucent portions, in other aspects the plunger or plunger cover 26 can include one or more windows or openings 31 that permit the electromagnetic radiation to pass therethrough. For example, the plunger or plunger cover 26 can include a pattern of windows positioned along portions of the cover 26 that contributes to formation of the halo. The windows or openings 31 can be covered by a transparent or translucent material or film to ensure that the plunger or plunger cover 26 is fluid tight. Other portions of the plunger or plunger cover 26 can be formed from an opaque material and, unlike in previously described examples, do not need to be capable of allowing light to pass through. In one example, selective lighting through these windows or openings 31 can be used to change patterns on the visible halo 120 or the color of the halo 120 based on certain system conditions or states. For example, some of the windows or openings 31 can be configured to have red light to emerge therethrough while other windows or openings 31 may be configured to have yellow light to emerge therethrough. Accordingly, the halo 120 may have a red color if only the red lights are turned on, a yellow color if only the yellow lights are turned on, or an orange color if all of the lights are turned. A certain color of the halo 120 may provide an indication of the operation of certain system conditions or states such as, but not limited to, the type of fluid being used, the size of the syringe, the volume of fluid in the syringe, the pressure within the syringe, the volume of fluid within the syringe, the presence of air within the syringe, etc.

Figure 10:
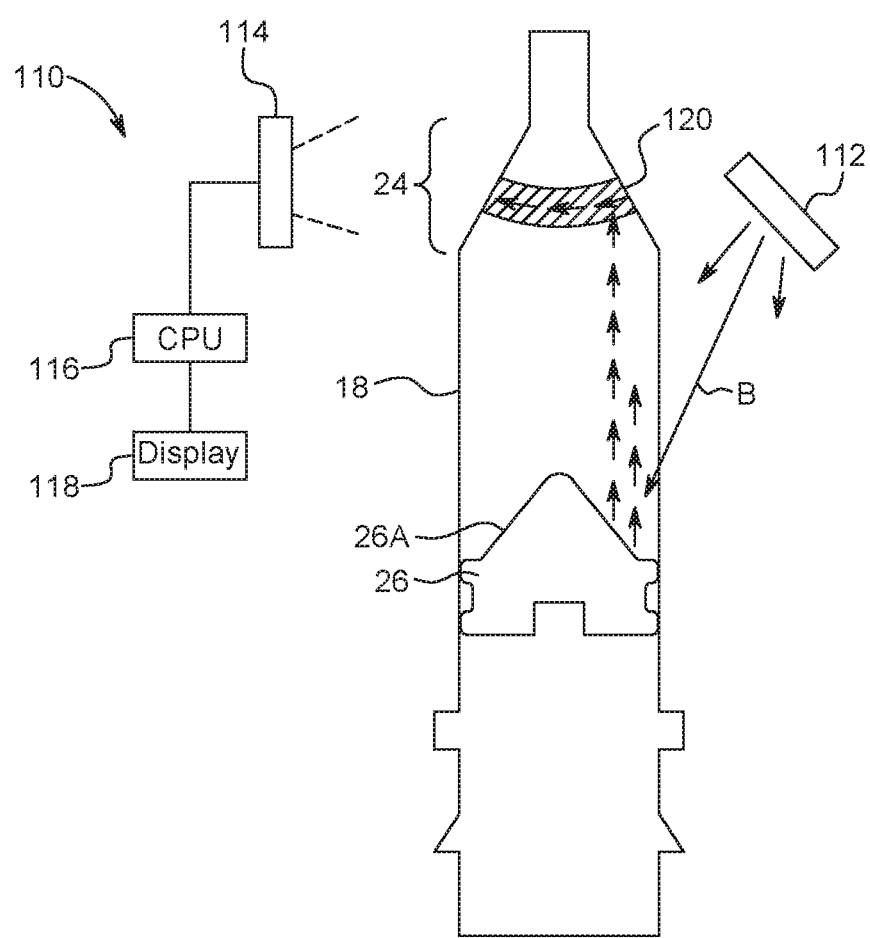
FIG. 10 is a schematic drawing of a syringe and fluid verification system with a reflective plunger.
Figure 11:
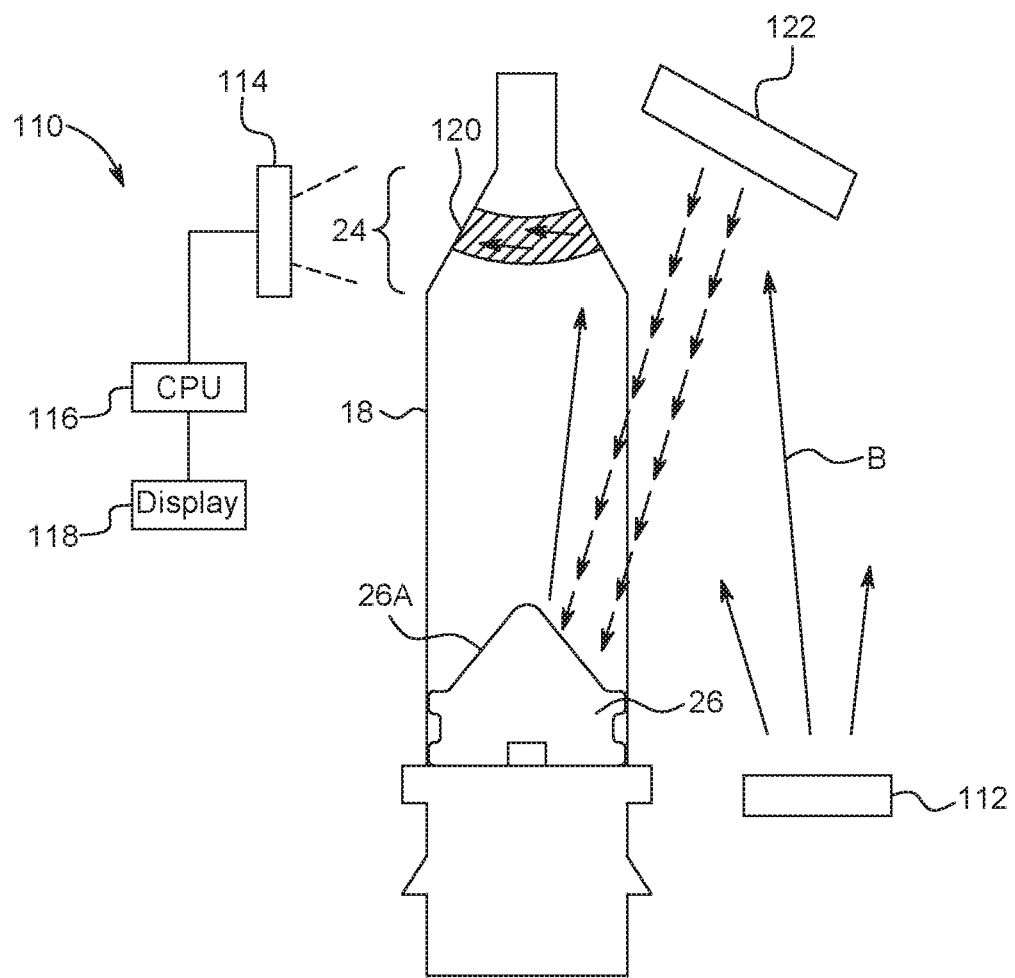
FIG. 11 is a schematic drawing of another embodiment of a syringe and fluid verification system with a reflective plunger.
Figure 12:
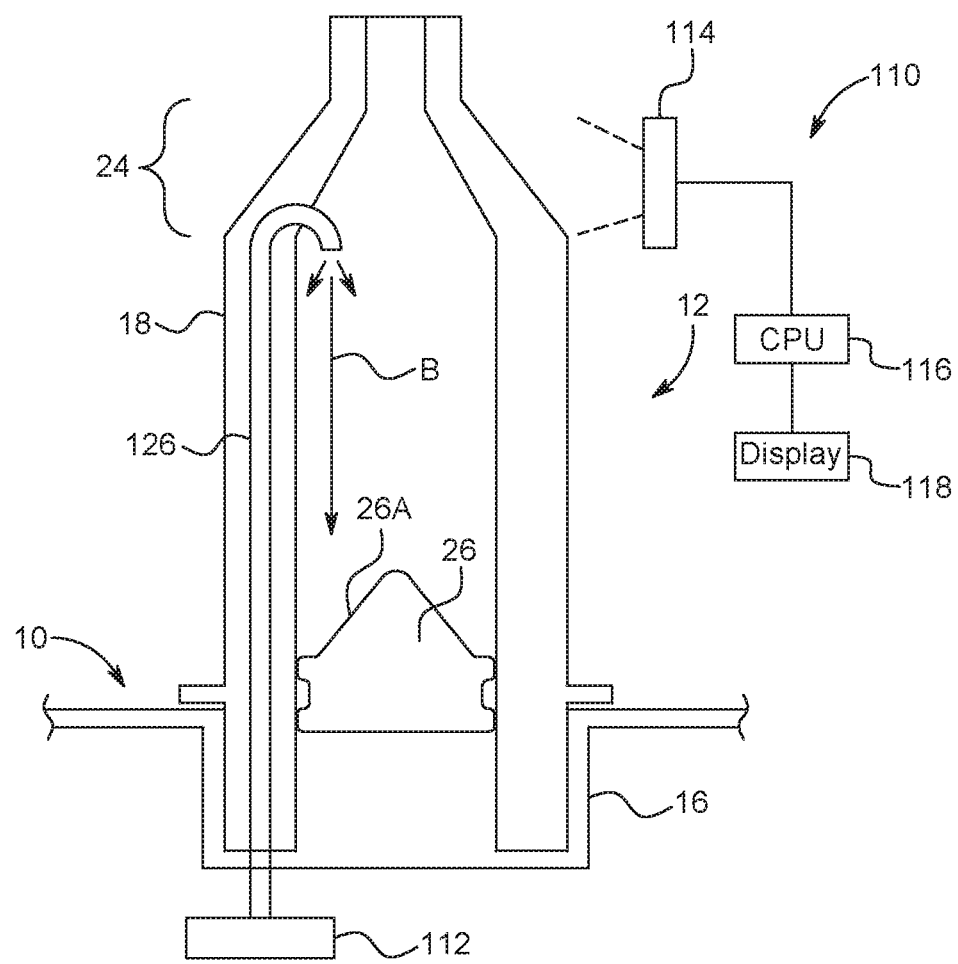
FIG. 12 is a schematic drawing of another embodiment of a syringe and fluid verification system with a reflective plunger and fiber optic light pipe.

In another example, the plunger or plunger cover 26 can be formed from or coated with a reflective or colored material rather than a translucent or transparent material. The reflective or colored material or surface reflects light directed toward the plunger or plunger cover 26 in the distal direction through the syringe barrel 18 to produce the halo. Exemplary fluid verification systems including a reflective plunger are illustrated in FIGS. 10-12, which are discussed herein in detail.

Figure 5A:
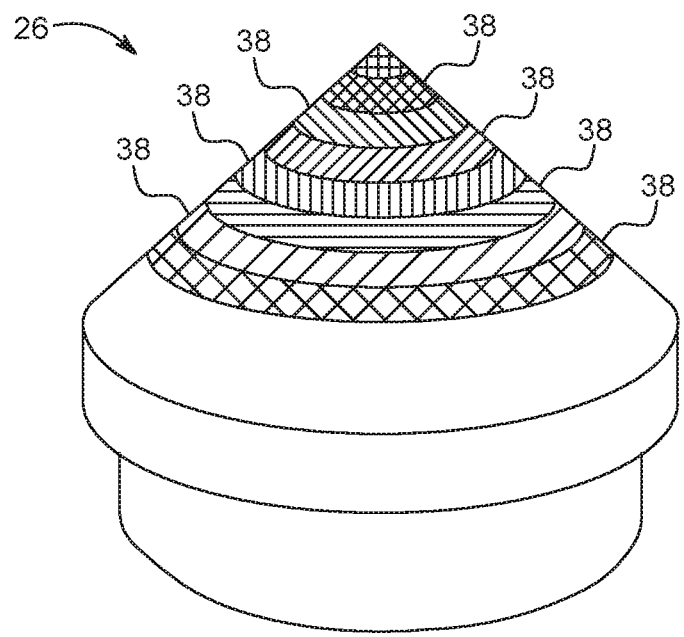
FIGS. 5A and 5B are perspective and schematic views, respectively, of a syringe plunger that may be utilized with the syringe of FIG. 2.
Figure 5B:
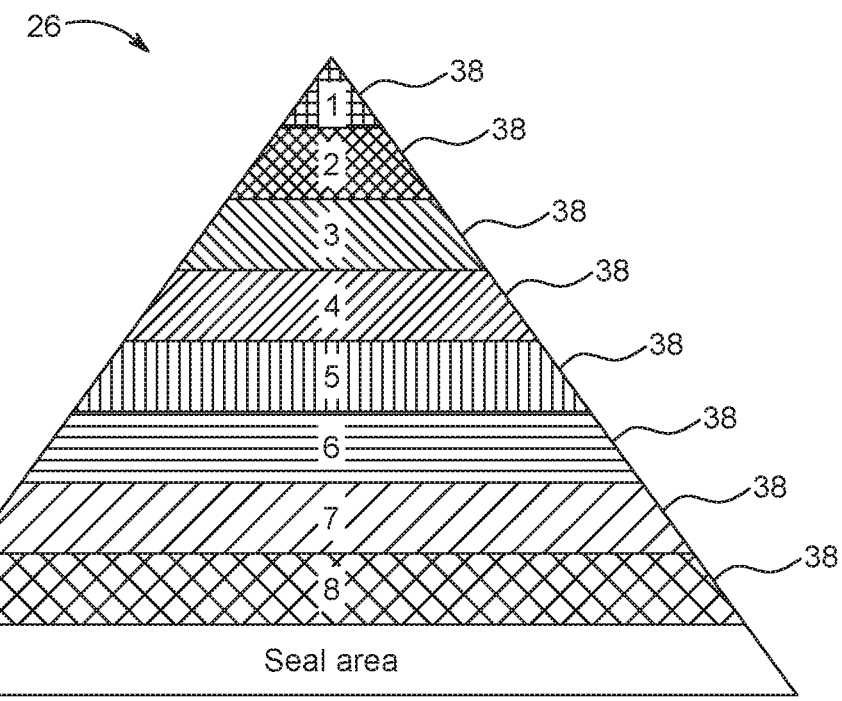

In yet another example, as shown in FIGS. 5A and 5B, the plunger or plunger cover 26 can be formed from or coated with a reflective material having a plurality of different colored stripes 38. The reflective material forming the stripes 38 reflects light directed toward the plunger or plunger cover 26 in the distal direction through the syringe barrel 18 to produce the halo. As the plunger or plunger cover 26 moves through the barrel, light reflects from a different stripe 38 depending on the position of the plunger or plunger cover 26 within the syringe barrel 18. Since each of the stripes 38 of the plunger or plunger cover 26 are different in color, the color and/or appearance of the halo changes depending on the stripe 38 upon which the light is reflected as the plunger or plunger cover 26 advances or retracts through the syringe barrel 18 during an injection or filing procedure. A sensor, such as an image capture device, can be positioned to capture images of the halo as the plunger or plunger cover 26 advances or retracts through the syringe barrel 18 and detect the change in color of the halo. A processor operatively coupled to the sensor and suitably programmed can then be used to determine the volume remaining within the syringe based on the color/appearance of the halo. While the example shown in FIGS. 5A and 5B shows eight (8) different colored stripes, this is not to be construed as limiting the present invention as any suitable number of stripes may be utilized. Alternatively, a plunger or plunger cover 26 may be configured to emit different colors of light at specific portions of the syringe to produce a different colored halo depending on the volume of fluid remaining in the syringe.

Additionally, patterns other than colored stripes could be used to encode information into the plunger in a way that it is viewed in the halo 120. One example of such a pattern is a barcode. In other aspects, symbols and/or words may be printed or applied to the plunger surface to be reflected to the halo portion and out to the user or image recognition means described herein. The process is similar to how a colored plunger creates a halo effect, however with symbols and/or letters in words, the reflection/refraction effect may slightly differ. For example, the syringe barrel represents a cylindrical lens with a focal point near the syringe tip. As an image approaches the focal point, the image may become distorted and stretched in ways which may make it unrecognizable. Additionally, the image may become inverted and difficult to read in the case of words. By controlling how the light reflects within the barrel, for example utilizing a Fresnel lens effect, the light hitting the plunger can be controlled to a point source which will focus on the letters regardless of plunger position. Thus, letters, words and/or symbols can be written on the plunger and then transmitted to the user through the halo only when the syringe is full of fluid. As described herein, no effect would be observed if the syringe contained significant amounts of air. In another aspect, symbols, words, and/or letters may be used to differentiate between saline and contrast in the syringe, as the letters or symbols written on the plunger will become distorted more significantly in contrast than in saline due to differences in the refractive index.

C. Generating an Illuminated Identification Pattern with the Exemplary Syringe

Having generally described various aspects the structure of the syringe 12 and plunger or plunger cover 26, with reference to FIG. 6, components of one example of a fluid verification system 110 will be discussed in detail. The fluid verification system 110 includes an electromagnetic radiation source 112 for generating the radiation beam that forms a halo 120. The electromagnetic radiation source 112 can be a light bulb, LED bulb, visible light emitter, infrared emitter, laser, other electromagnetic radiation sources, or ambient light provided to project an electromagnetic radiation beam through the interior 19 of the syringe 12. In certain aspects, electromagnetic radiation source 112 emits electromagnetic radiation generally in an axial direction through syringe barrel 18 towards the distal end of the syringe.

1. Electromagnetic Radiation Source Positioned Beneath the Plunger

Figure 6:
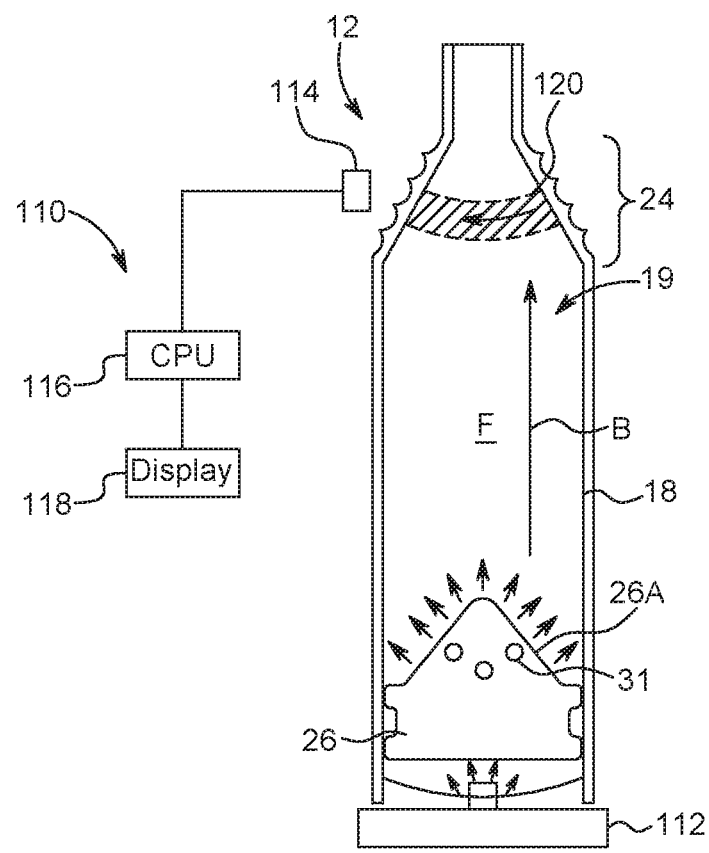
FIG. 6 is a schematic drawing of a syringe and fluid verification system including a backlit plunger, according to an aspect of the disclosure.

For example, as shown in FIG. 6, an electromagnetic radiation beam B passes through the translucent or transparent plunger or plunger cover 26 and toward the distal end 24 of the barrel 18. The electromagnetic radiation source 112 can be configured to increase conspicuousness of the halo 120 or to tailor the halo 120 for particular sensors or electromagnetic radiation detectors. In one example, the electromagnetic radiation source 112 comprises a laser of a specific wavelength, for example in one embodiment having a wavelength of about 532 nm (e.g., a green laser). Lasers emitting electromagnetic radiation at other wavelengths within the visible region are also envisioned. The laser electromagnetic radiation source 112 can be used with neutral colored or transparent plungers and still produce a conspicuous colored halo 120. In other examples, the electromagnetic radiation source 112 can emit electromagnetic radiation outside the visible spectrum provided that the system includes a sensor or camera capable of detecting radiation (e.g. the halo 120) within the emitted wavelength. In still other examples, the electromagnetic radiation source 112 can emit polarized light or certain wavelengths of filtered light, which can be more easily distinguished from ambient light. In other examples, electromagnetic radiation source 112 can be configured to emit pulses of light according to a predetermined and identifiable sequence, which can be identified by a system operator or automatically detected by a sensor.

With continued reference to FIG. 6, the electromagnetic radiation source 112 is disposed below the plunger or plunger cover 26 to backlight the plunger or plunger cover 26. For example, LED bulbs or other electromagnetic radiation emitting devices can be mounted to a base portion of a syringe-receiving stand, a piston, an actuator, or the syringe port configured to receive the syringe 12 and positioned to emit an electromagnetic radiation beam, for example, in the axial direction through the syringe barrel 18. Accordingly, in some examples, the electromagnetic radiation source 112 can be integrated with the injector 10 (shown in FIG. 1). For example, the electromagnetic radiation source 112 can be positioned on the injector port 16 (FIG. 1), adjacent to the drip flange 28 of the syringe barrel 18, or at some other convenient location on the injector adjacent to the syringe port.

In other examples, the fluid verification system 110 can be a standalone structure including a base or holder for receiving a syringe 12 to be tested. The electromagnetic radiation source 112, such as the LED or standard light bulb, can be positioned on or adjacent to the base or holder. In that case, the syringe 12 is verified to ensure that it is properly filled with fluid F. After verification is completed, syringe 12 is removed from the base or holder and transferred to an injector, such as fluid injector 10, for delivery of fluid F to the patient.

Electromagnetic radiation passing through the plunger or plunger cover 26 substantially radiates through the syringe barrel 18 to form the halo 120 when the syringe is filled with fluid. With specific reference to FIG. 7, when the syringe 12 is filled or partially filled with air, the electromagnetic radiation beams pass through the syringe barrel 18, but do not form a distinctive illuminated portion or halo 120 near the distal end 24 thereof. In contrast, as shown in FIG. 8, when the syringe 12 is entirely filled with fluid F, the electromagnetic radiation beams are refracted by the fluid F and the syringe barrel walls, which produces a halo 120 near the distal end 24 of the syringe 12. As discussed in greater detail in connection with the methods and steps for syringe verification herein, a system operator or automated image reading or optical device (e.g. sensor 114) can identify whether the halo 120 is present and, if present, is the correct shape and size. If the halo 120 is too small, not bright enough, or not present at all, this may indicate that the syringe is not filled with sufficient fluid or contains air, and the system operator can add additional fluid F to the syringe 12 for complete filling prior to injection into a patient. If a halo 120 having the correct size, shape, and brightness is identified, then verification that the syringe is filled with fluid is complete and the fluid contents of the syringe 12 are ready for administration to a patient. Accordingly, fluid verification system 110 provides a suitable visual indication of whether a syringe 12 is full of fluid or whether even a small amount of air is present in the syringe interior 19.

Figure 7:
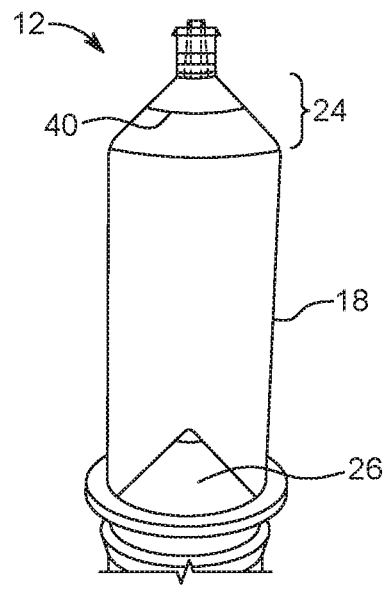
FIG. 7 is a schematic drawing of a syringe that is completely or partially filled with air in use with the fluid verification system of FIG. 6.
Figure 8:
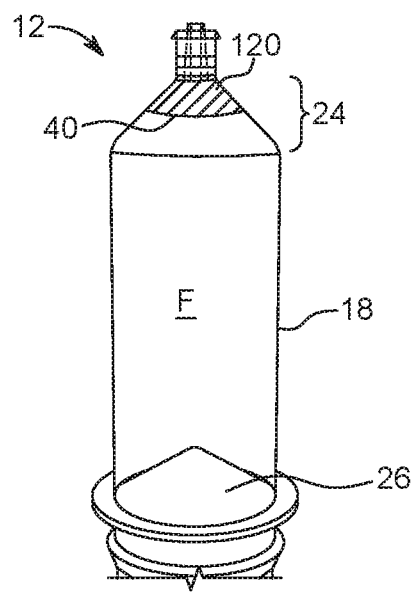
FIG. 8 is a schematic drawing of a fluid filled syringe in use with the fluid verification system of FIG. 6.

In addition, as shown in FIGS. 7 and 8, a line 40 may be formed on a distal end 24 of the syringe barrel 18 and extend around a circumference of the distal end 24 of the syringe barrel 18. The line 40 may be formed on the barrel 18 using any suitable method such as, but not limited to, printing, overmolding, and etching. The line 40 is configured to work in conjunction with the halo 120 to provide the operator with a quick, visual indication of the type of fluid within the syringe 12. For example, the halo 120 will be different sizes depending on the type of fluid present within the syringe due to different properties of different fluids. Accordingly, the line 40 may be formed on the syringe 12 to align with a particular portion of the halo 120, such as the bottom edge as shown in FIG. 8, when a first fluid is present within the syringe 12 and to align with a second predetermined portion of the halo 120, such as a middle portion, if a second fluid is present within the syringe 12 or may be positioned away from the halo 120 if the second fluid is present within the syringe 12. In this manner, the operator can quickly and easily visually determine the location of the line 40 in relation to the halo 120 and, based on this information, determine the type of fluid present within syringe 12.

Figure 9:
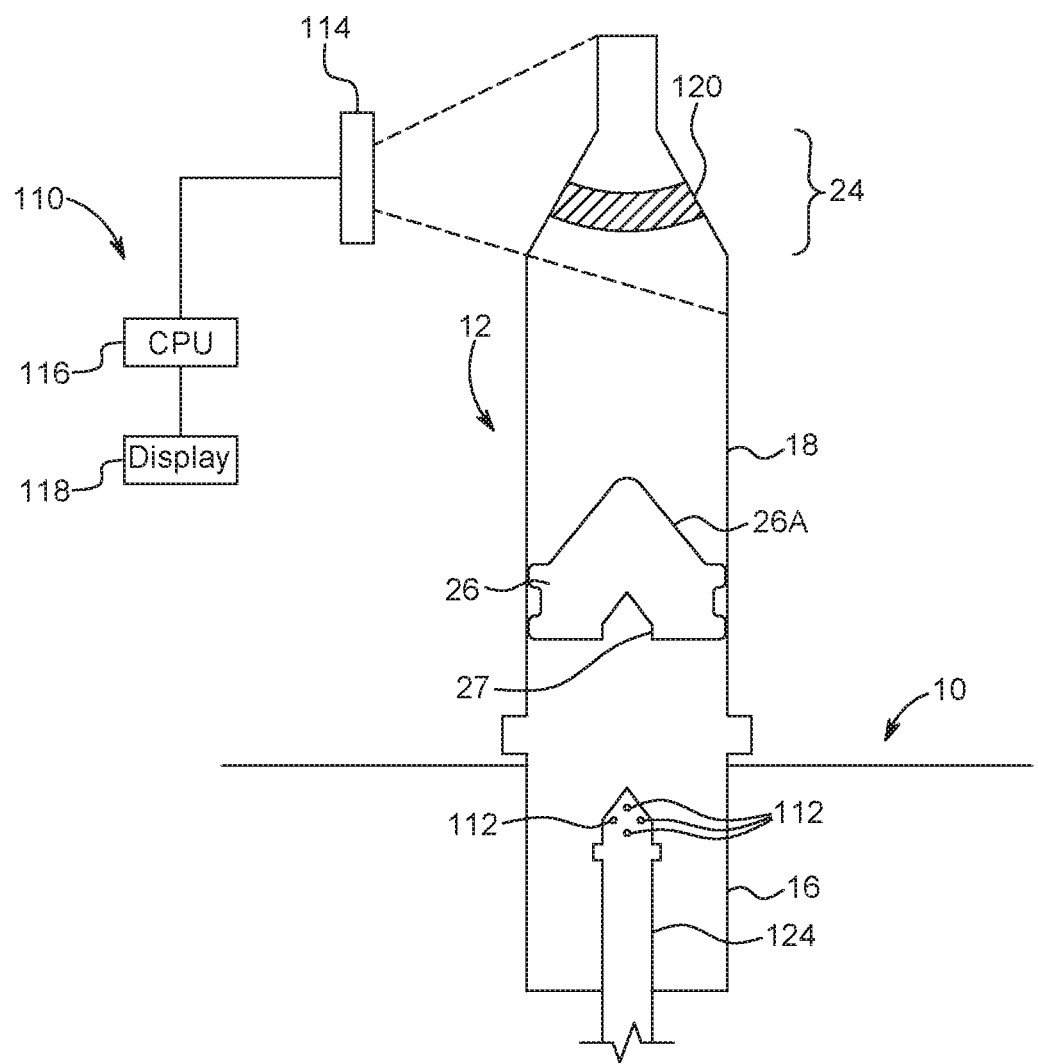
FIG. 9 is a schematic drawing of another example of a syringe and fluid verification system with a backlit plunger, according to an aspect of the disclosure.

With reference to FIG. 9, another example of a syringe 12 and fluid verification system 110, including a backlight translucent or transparent plunger or plunger cover 26, is illustrated. The syringe 12 is mounted to a syringe port 16 of an injector 10. One or more electromagnetic radiation sources 112, such as LEDs, are mounted to or embedded in a distal end of a piston rod 124 of the injector 10. When actuated, the piston rod 124 advances toward and is received within the cavity 27 defined by the plunger or plunger cover 26. The LEDs emit light in the axial direction through the plunger cover 26 for producing the halo 120 adjacent to the distal end 24 of the syringe barrel 18 in the manner discussed above. The halo 120 can be identified by the sensor 114 positioned adjacent to the distal end 24 of the syringe barrel 18.

2. Electromagnetic Radiation Source Positioned so that Radiation Reflects from the Surface of the Plunger With reference to FIG. 10, the radiation source 112 can also be arranged or positioned so that energy or electromagnetic radiation reflects from a distal surface 26A of the plunger or plunger cover 26 axially through the syringe barrel 18 to form the halo 120. For example, an electromagnetic radiation source 112, such as described herein, could be positioned outside the barrel, for example, near the distal end 24 of the barrel 18 to project an electromagnetic radiation or light beam B toward the distal surface 26A of the plunger or plunger cover 26 through the syringe barrel 18. The electromagnetic radiation or light beam B then reflects off the plunger or plunger cover 26 in the distal direction with concomitant refraction/reflection by the fluid and/or syringe wall material to form a visible halo at the distal end of the syringe.

3. Electromagnetic Radiation Source Positioned Adjacent to the Surface of the Injector In another example, as shown in FIG. 11, the system 110 can include an electromagnetic radiation source 112 positioned adjacent to the surface of the injector 10 and/or syringe port 16 (shown in FIG. 1). The electromagnetic radiation source 112, such as described herein, can be configured to focus and reflect a light or radiation beam B from a mirror 122 or other reflective element located near the distal end 24 of the syringe barrel 18. The mirror 122 directs the light or electromagnetic radiation beam toward the distal surface 26A of the plunger or plunger cover 26, so that the radiation or light can reflect from the plunger or plunger cover 26 to form the halo 120 when the syringe is filled with fluid. The halo 120 can be identified visually by the operator or by the detector or sensor 114.

4. Electromagnetic Radiation Source Including Fiber Optics

With reference to FIG. 12, in another example, a fiber optic light pipe 126 is used to provide light or electromagnetic radiation from an electromagnetic radiation source 112 toward the distal end 24 of the barrel 18, for example wherein the source is associated with the injector body, and to shine or direct the light toward the distal surface 26A of the plunger or plunger cover 26. In one example, the light pipe 126 can be embedded in the syringe barrel 18 itself. Alternatively, the light pipe 126 may be embedded in a pressure jacket surrounding the syringe barrel 18. In that case, light can be directed from the electromagnetic radiation source 112 located, for example, in the syringe port 16 of the injector 10 through the light pipe 126 toward the distal end 24 of the barrel 18. Light emitted from the light pipe 126 is shown or directed toward the distal surface 26A of the plunger or plunger cover 26 as shown by the light beam B, and permitted to reflect therefrom in the manner discussed in connection with the examples illustrated in FIGS. 10 and 11 to form a halo at the distal end of the syringe when the syringe is filled with fluid.

5. The Illuminated Identification Pattern or Halo

Figure 13:
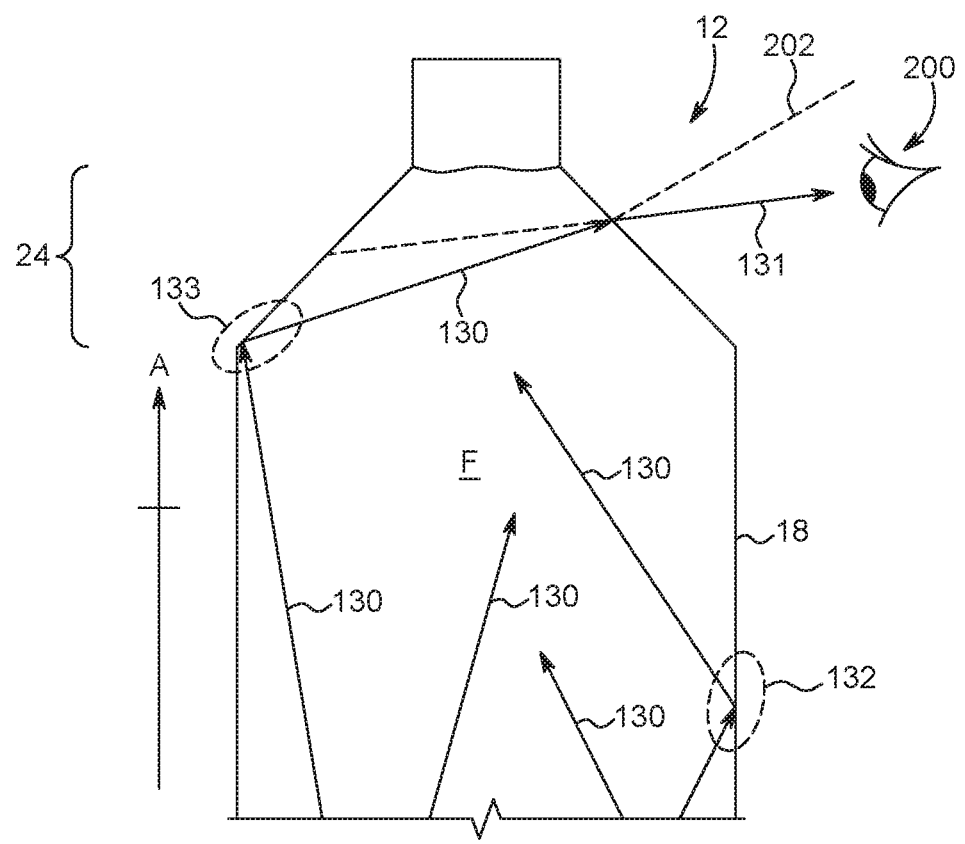
FIG. 13 is a schematic drawing showing light rays reflecting within and transmitting through a fluid filled syringe barrel according to an aspect of the disclosure.

With reference to FIG. 13, details of how electromagnetic radiation is refracted by fluid F and/or the material in the wall of barrel 18 to produce the halo 120 will be discussed in detail. As shown in FIG. 13, light rays, denoted generally as 130, which are scattered in multiple orientations when passing through the plunger or plunger cover 26 (shown in FIGS. 6 and 9), travel generally in the axial direction A toward the distal end 24 of the syringe barrel 18. Some of the light rays 130 exit the syringe barrel 18 through the transparent or translucent sidewall of the syringe barrel 18, meaning that the illuminated plunger 26 is visible to an observer 200. Some light rays 130 reach the tapered, conical distal end 24 of the barrel 18 directly without contacting the sidewall of the barrel 18. Light rays 130 shining directly on the distal end 24 of the barrel 18 would be visible to an observer 200 looking at a top of the syringe 12 from an elevated position. Some light rays 130 are focused to the distal end 24 of the syringe barrel 18 by total or partial internal reflectance, shown at reference number 132, from the syringe barrel 18. For example, light rays 130 directed to one side of the tapered, conical distal end 24 of the syringe barrel 18 are reflected by total internal reflectance, as shown at number 133, toward the opposite side of the tapered distal end 24 when the syringe is filled with fluid and the difference in refractive index between the fluid, the syringe wall material and the air outside the syringe are different to cause internal reflection. If the syringe barrel 18 is filled completely with air or only partially filled with fluid F, the light rays 130 are not sufficiently internally reflected or focused to the distal conical end and would be only faintly visible, if at all, to an observer 200 over the area of syringe 12 filled with air. Without intending to be limited by any theory, it is believed that a large percentage of the light rays travelling through the volume of the syringe containing air are not internally reflected at the syringe barrel wall and, instead, exit the syringe through the sidewall; and since there is no substantial internal reflection, the light rays are not focused to the distal end of the syringe to produce an observable halo. In particular, focused light rays 130 would not be visible as a halo when looking at the syringe barrel 18 from a straight-on position or true side view when air is in the syringe. Thus, the halo 120 does not appear to be present when the syringe barrel 18 is not fully filled with fluid.

However, as shown in FIG. 13, when the syringe 12 is filled with fluid F, the light rays 130 reflected toward and focused to the tapered distal end 24 of the barrel 18 are refracted, as shown at line 131, due to the difference in refractive index of the fluid relative to the outside air and the syringe wall material. Specifically, as discussed herein, air has a refractive index of substantially 1. In comparison, the refractive index of saline is about 1.34, the refractive index of contrast is about 1.46, and the refractive index of PET is about 1.57. The refracted light beams 130 exiting the syringe barrel 18 are viewable to an observer 200 at a lower angle compared to when the syringe barrel 18 is only partially filled with the fluid F. Further, due to the refraction, the light rays 130 may be further focused to increase the intensity of the light halo observed by the observer 200. Accordingly, when looking at the fluid filled syringe 12 at a straight-on, true side view, or slightly elevated position, the observer 200 sees the illuminated halo 120 which has a distinctive appearance.

The structure and geometries of the syringe 12 and particularly the tapered, conical distal end are chosen to ensure that the halo 120 is easily visible at a predetermined portion of the barrel 18 (i.e., the distal end 24) from a particular set of positions or orientations. For example, in some embodiments, the injector 10 holds the syringe 12 at a tilted orientation (e.g., either leaning upwards or downwards from between about 0 to about 30 degrees relative to plane of the injector). To account for the tilted orientation of the syringe 12, the shape of the barrel 18 and distal end 24 of the barrel 18 can be selected to increase visibility of the halo 120 when viewed in a tilted position. If the syringe 12 is held in a substantially straight (e.g., not tilted) position by the injector 10, then the syringe 12 is shaped so that the halo 120 can be easily seen when the syringe 12 is viewed from a straight-on or true side view orientation.

Figure 14A:
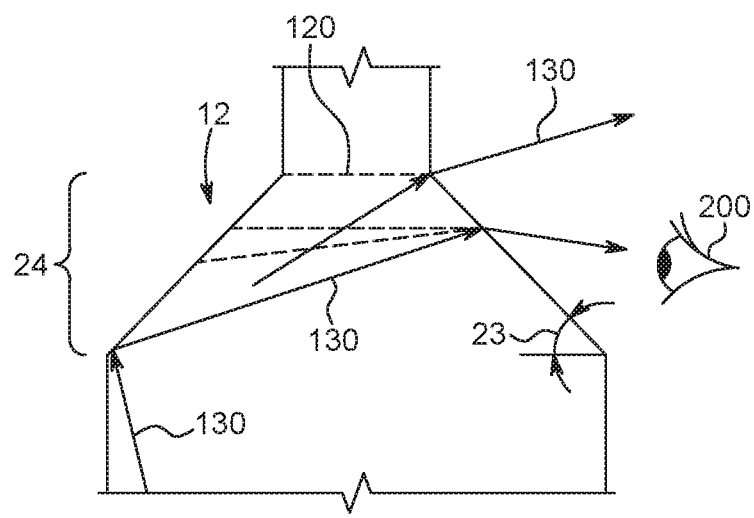
FIGS. 14A-14C are schematic drawings of portions of the distal end of embodiments of a fluid filled syringe for use with a fluid verification system, according to aspects of the disclosure.

More specifically, with reference to FIG. 14A, if the syringe 12 is oriented such that it is generally viewed from a straight-on or tilted back (e.g., from 10 degrees to 30 degrees tilt) orientation, the angle 23 of the tapered distal end 24 of the barrel 18 is from about 30 degrees to 60 degrees, and in certain embodiments about 45 degrees relative to the horizontal. An angle of about 45 degrees creates a halo 120 that may be more easily seen than at a straight-on view angle. In particular, as shown in FIG. 14A, the observer 200 can see the light rays 130 that form the halo 120 at a rather low orientation.

Figure 14B:
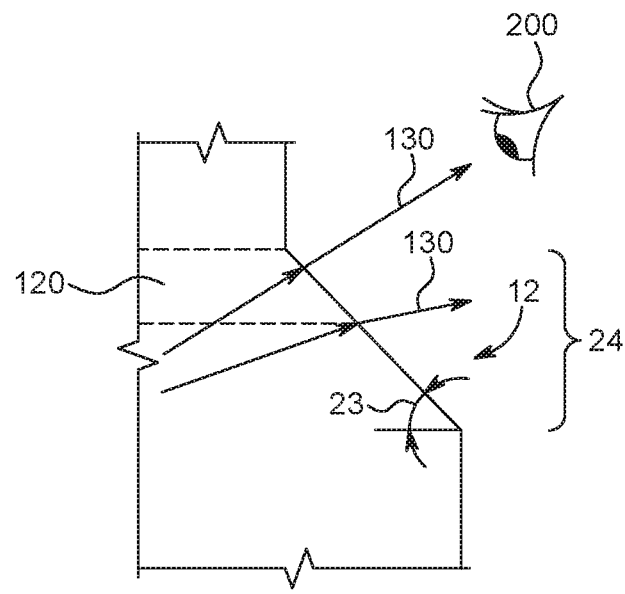

In contrast, as shown in FIG. 14B, for a syringe 12 having a distal end 24 with a steeper angle 23, the halo 120 is visible to the observer 200 at a higher (e.g., downward looking) orientation. If the syringe 12 is expected to be viewed in a tilted forward position, the higher viewpoint may be appropriate. In some examples, the distal end 24 of the barrel 18 can also have a dome shape. However, in most circumstances, the halo 120 may be easier to see through a tapered distal end 24 rather than a dome shaped distal end 24.

Figure 14C:
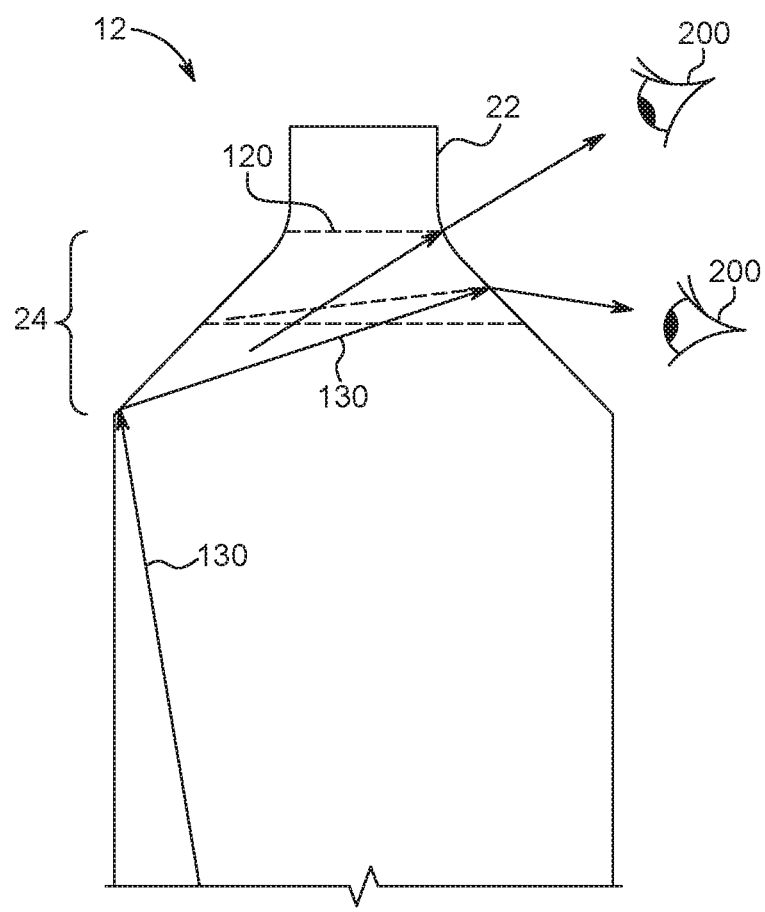

In another example, as shown in FIG. 14C, the distal end of the syringe 12 includes a distal portion 24 that includes a curved and angled portion extending from the barrel 18 to the nozzle 22 or tip. The distal portion 24 having such a curved and angled portion produces a halo 120 that can be seen from a wider range of viewing angles. In particular, as shown in FIG. 14C, the light beams 130 can be seen by the observer 200 at either the straight-on orientation or a more downwardly directed orientation. Accordingly, for a syringe 12 having a distal portion 24 as shown in FIG. 14C, the halo 120 is visible regardless of whether the injector 10 holds the syringe 12 in a slightly tilted or straight position.

6. Operation of Fluid Injection System with the Exemplary Syringe

With reference again to FIGS. 1, 2, and 6, in use, an operator inserts the proximal end 20 of the barrel 18 into a corresponding syringe port 16. The operator may be required to exert some force against each syringe 12 so that the locking flange 32 of the syringe 12 engages with corresponding locking structures (not shown) of the syringe port 16 to form a suitable connection therewith. In certain examples, the operator continues to press the syringe 12 into the port 16 until the insertion portion 30 of the syringe barrel 18 is entirely inserted. In some cases an audible or tactile signal, such as a click, indicates that the syringe barrel is fully inserted, locked, and ready for use.

The syringe 12 may be preloaded with a fluid F. Alternatively, the injector 10 can automatically or manually draw fluid F into the syringe barrel 18 from an external fluid source. Once the syringe 12 is inserted in the port 16 and filled with fluid F, the electromagnetic radiation source 112 is turned on causing light beams to project through the plunger or plunger cover 26. Alternatively, as discussed herein in connection with the exemplary systems illustrated in FIGS. 10-12, electromagnetic radiation or light can be directed toward the distal surface 26A of the plunger cover 26 and reflected therefrom in the axial direction. In some examples, syringe insertion and halo identification can be coordinated such that the electromagnetic radiation source 112 turns on automatically each time that a syringe 12 is loaded into the injector 10. Alternatively, the system operator can manually turn on the electromagnetic radiation source 112 by, for example, inputting a command through the user interface or pressing an activation button. Once the electromagnetic radiation source 112 is activated, the presence or absence of the illuminated portion or halo 120 (shown in FIGS. 6 and 9) can be identified and/or detected, either by the technician or automatically by the sensor. Specifically, if the syringe 12 is fully filled with the fluid F, the halo 120 appears. If the syringe 12 is filled with air or only partially filled with fluid, then the halo 120 is either less pronounced or entirely absent. For example, the halo 120 begins to become less pronounced (i.e., smaller in size and/or less bright) as soon as air is introduced into the syringe and continues to fade until it is entirely absent when about 5 mL of air is present in a syringe 12 of the distal end of the syringe when a syringe such as the syringe shown in FIG. 2 is utilized in the system. In other examples, the halo 120 is not visible when a percentage of a volume of air present in the distal end 24 of the syringe 12 is greater than about 15% of the volume of the conical shaped distal end 24 of the syringe 12. In still other examples, the halo 120 is not visible when a percentage of a volume of air present in the distal end 24 of the syringe 12 is greater than about 10% of the volume of the conical shaped distal end 24 of the syringe 12, and in yet other examples, the halo 120 is not visible when a percentage of a volume of air present in the distal end 24 of the syringe 12 is greater than about 20% of the volume of the conical shaped distal end 24 of the syringe 12. In some examples, the system operator manually confirms, such as by visual verification, that the halo 120 is present before actuating the injector 10.

Alternatively, according to another aspect of the present disclosure, the illuminated halo 120 can be detected automatically by one or more sensors 114, such as a digital camera. More specifically, an image or images of the distal end 24 of the barrel 18 may be obtained by the one or more sensors 114. The obtained image can be analyzed by a processor using image processing techniques (as will be discussed in greater detail herein). For example and as will be discussed in detail herein, pattern recognition algorithms can be used to identify an expected structure and other properties of the syringe 12, fluid fill volume, fluid properties, and shape and/or location of the halo 120, among other properties and features. The pattern recognition can also be used to identify information about the syringe 12, such as syringe fluid volume or preferred injection parameters for a particular syringe size and geometry. Edge to edge distance calculating algorithms can be used to identify the position and length of the halo 120. Edge to edge distance calculating algorithms can also be used to determine a length of the meniscus formed by the fluid F contained in the syringe 12. Recognition of the meniscus position and size can be used to determine the fluid volume contained in the syringe 12 and free space (i.e. air volume), if any, between the meniscus and syringe nozzle. Brightness determining algorithms can be used to determine the intensity of the halo 120. As previously discussed, the brightness of the halo 120 may be used as an indicator of an amount of air present in the syringe 12. Accordingly, the processing algorithm could ensure that the halo brightness exceeds certain predetermined threshold values thus indicating that threshold amounts of air in the syringe are not exceeded.

In some examples, the injector 10 can be configured to "unlock/lock" based on whether the halo 120 is identified. For example, if the halo 120 is not identified, the injector 10 could enter a "locked" state preventing an injection from proceeding and/or request that the tested syringe be replaced with a new one. If the halo 120 is identified, the injector 10 may "unlock" and allow the operator to access other features of the user interface of the injector 10 and allow the injection procedure to proceed. Similarly, the injector 10 can be configured to cancel or halt a scheduled injection procedure if the sensor 114 fails to identify the halo 120 or if the halo 120 is identified but is not of sufficient brightness. If the halo 120 is present, the injector 10 can be configured to automatically begin the injection procedure. Activating the injector 10 causes the linear actuator to advance the piston rod 124 in the distal direction to contact and engage the plunger or plunger cover 26. Advancing the plunger or plunger cover 26 in the distal direction through the barrel 18 expels fluid F from the syringe 12, thereby injecting fluid F into the patient through any known injection structure, such as an IV tube or needle accessory.

D. Alternative Exemplary Syringe for Use with Fluid Injection System

1. Structure of Alternative Exemplary Syringe

Figure 15A:
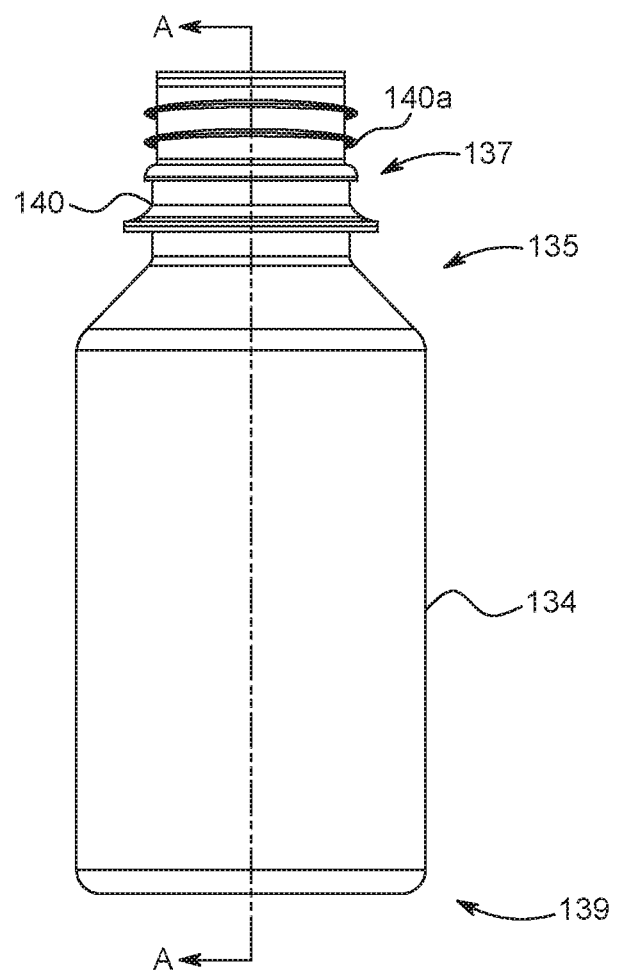
FIG. 15A is a side view of a rolling diaphragm syringe in accordance with one aspect of the present disclosure.
Figure 15B:
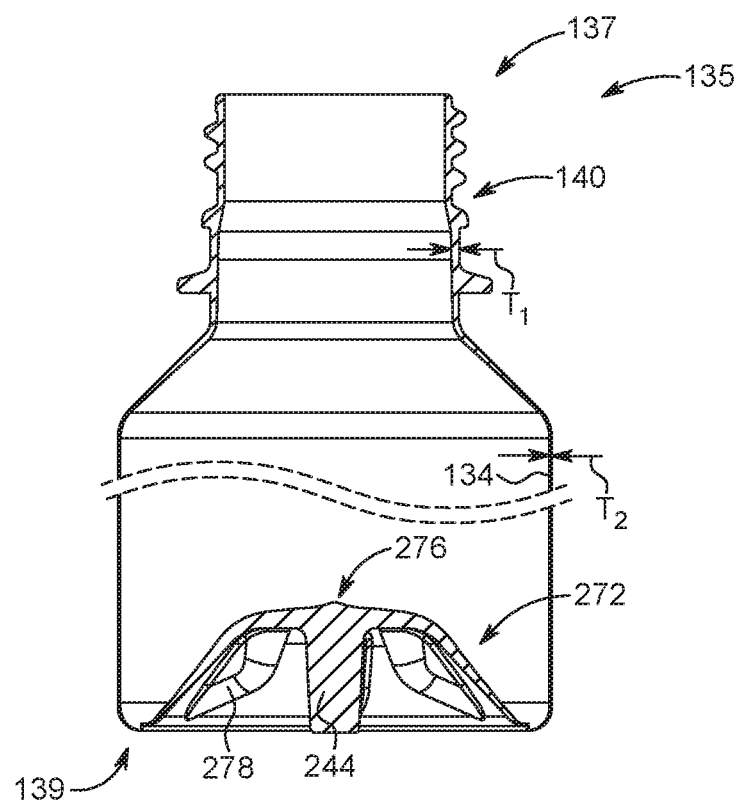
FIG. 15B is a cross-sectional side view of the rolling diaphragm syringe shown in FIG. 15A taken along line A-A.
Figure 18A:
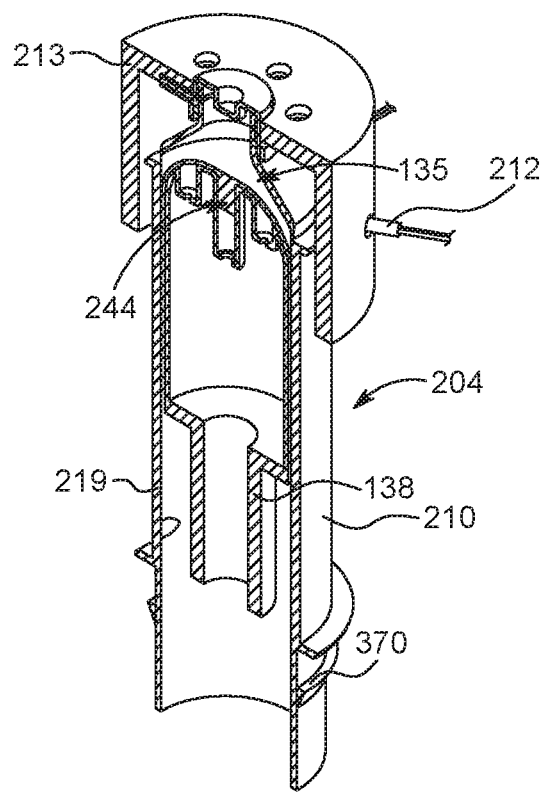
FIGS. 18A and 18B are perspective cross-sectional views of the rolling diaphragm syringe and portions of an engagement mechanism illustrating second and third configurations of an electromagnetic radiation source, according to aspects of the disclosure.
Figure 18B:
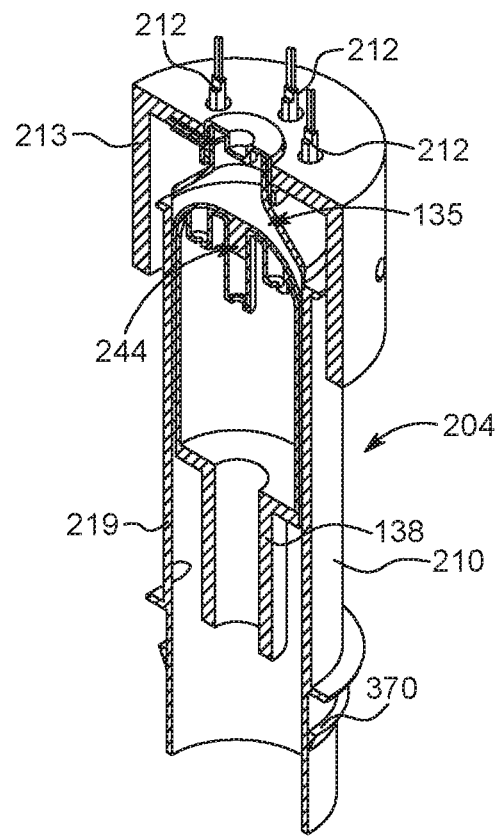

FIGS. 15A and 15B illustrate an alternative exemplary syringe that may be utilized with fluid injector 10. More specifically, these figures illustrate a rolling diaphragm syringe 135 in accordance with another aspect of the present disclosure. Various features of a rolling diaphragm syringe are described in detail in International PCT Application Publication No. WO 2015/164783, the disclosure of which is incorporated by this reference. FIG. 15B is a cross-sectional side view the rolling diaphragm syringe 135 shown in FIG. 15A taken along line A-A. Referring initially to FIG. 15A, the rolling diaphragm syringe 135 generally includes a hollow body that includes a forward or distal end 137, a rearward or proximal end 139, and a flexible sidewall 134 extending therebetween. The sidewall 134 of the rolling diaphragm syringe 135 defines a soft, pliable or flexible, yet self-supporting body that is configured to roll upon itself, as a "rolling diaphragm", under the action of a piston 138 (shown in FIGS. 18A and 18B) of the fluid injection 10. In particular, the sidewall 134 of the rolling diaphragm syringe 135 is configured to roll such that its outer surface is folded and inverted in a radially inward direction as the piston 138 is moved in a distal direction and unroll and unfold in the opposite manner in a radially outward direction as the piston 138, for example a piston releasably attached to a proximal end of an end wall 136 of the rolling diaphragm syringe 135, is retracted in a proximal direction.

The rolling diaphragm syringe 135 may be made of any suitable medical-grade plastic or polymeric material. In various aspects, the clear plastic material may withstand sterilization procedures, such as exposure to ethylene oxide or electromagnetic radiation sterilization procedures.

Figure 17A:
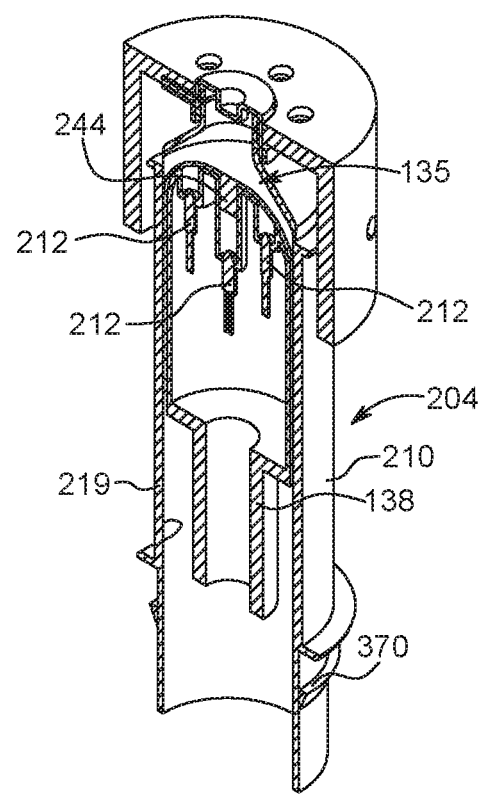
FIGS. 17A and 17B are a perspective cross-sectional view and cross-sectional view of the rolling diaphragm syringe and portions of an engagement mechanism illustrating a first configuration of an electromagnetic radiation source, according to an aspect of the disclosure.
Figure 17B:
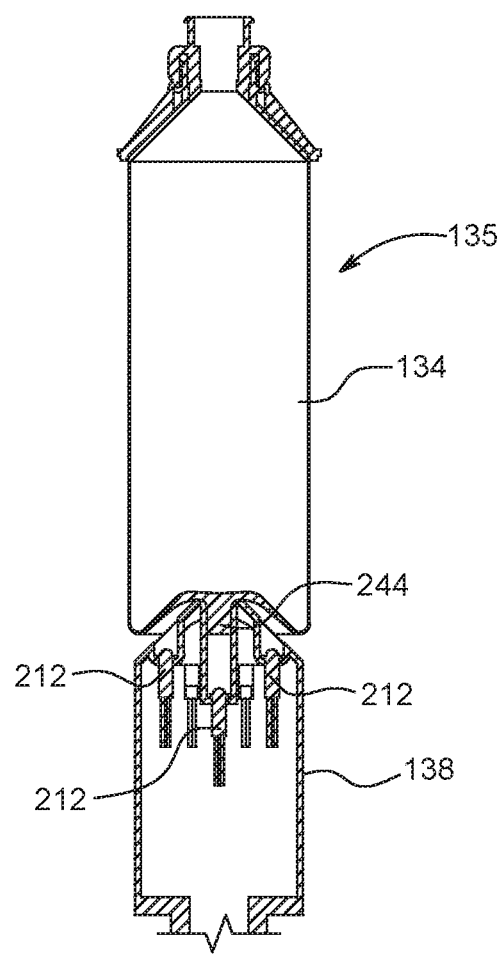

With reference to FIG. 15B and with continued reference to FIG. 15A, the distal end 137 of the rolling diaphragm syringe 135 has an open-ended discharge neck 140 having a connection member 140a for connecting to a corresponding connection member, for example the cap of FIG. 17 as described herein, which may connect to a fluid path set (not shown). The discharge neck 140 has a first sidewall thickness $T_1$ that is greater than a thickness $T_2$ of a sidewall 134. Thickness $T_1$ is selected such that the discharge neck 140 may be sufficiently rigid to allow for connecting to a corresponding connection member of a fluid path set (not shown) without substantially deforming the discharge neck 140, for example during an injection procedure. Thickness T$_2$ is selected such that the sidewall 134 of the rolling diaphragm syringe 135 is flexible to allow for rolling over and unrolling of the sidewall 134 as described herein. The proximal end 139 of the rolling diaphragm syringe 135, such as closed end wall 136, may be reinforced to prevent deformation during rolling over, or in particular aspects, unrolling of the sidewall 134. In some aspects, the proximal end 139 of the rolling diaphragm syringe 135 is configured for engagement with the piston 138.

The end wall 136 may have a central portion 276 having a substantially dome-shaped structure and a piston engagement portion 244 extending proximally from the central portion 276, such as an approximate midpoint of the central portion 276. In some aspects, a distal most end of the central portion 276 may be substantially flat. The piston engagement portion 244 is configured for engagement with the engagement mechanism on the piston 138 of the fluid injector 10. The proximal end 139 of the rolling diaphragm syringe 135 may have one or more ribs 278 protruding radially outward from the piston engagement portion 244 along a proximal surface of a ramp 272.

Figure 16A:
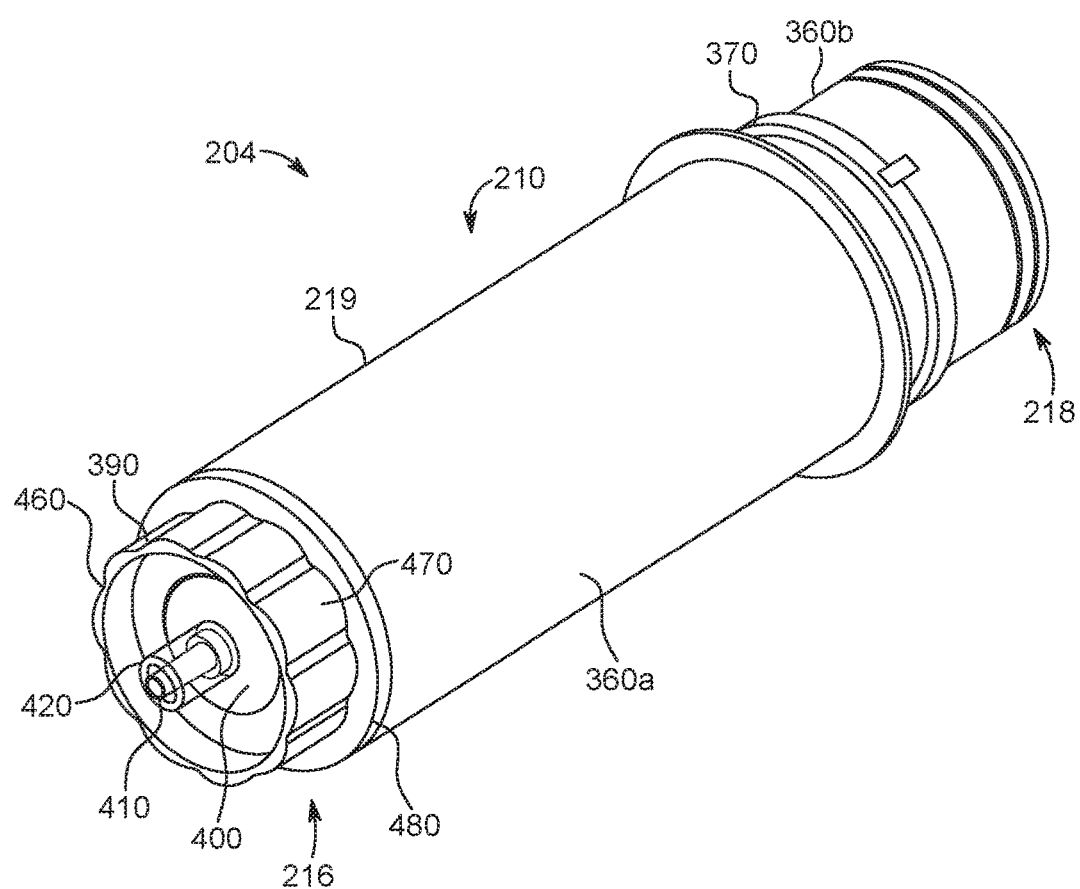
FIG. 16A is a perspective view of a rolling diaphragm syringe and a pressure jacket in accordance with another aspect of the present disclosure.

FIG. 16A is a perspective view of a syringe assembly 204 having a rolling diaphragm syringe 135 (shown in FIG. 16B) and a pressure jacket 210 in accordance with the present disclosure. The syringe assembly 204 includes the pressure jacket 210 that removably interfaces with the injector 10 (shown in FIG. 1), as described herein. The pressure jacket 210 has a distal end 216, a proximal end 218, and a sidewall 219 extending between the distal end 216 and the proximal end 218 along a longitudinal axis of the pressure jacket 210 to define an internal throughbore 221 (shown in FIG. 16B). In some aspects, the sidewall 219 of the pressure jacket 210 is shaped to receive at least a portion of the rolling diaphragm syringe 135 (shown in FIG. 16B) within the throughbore 221. The sidewall 219 of the pressure jacket 210 has a first distal portion 360a for receiving at least a portion of the rolling diaphragm syringe 135, and a second proximal portion 360b for interfacing with the injector 10. The first distal portion 360a may have an open end configured to releasably receive a cap 390 that encloses the interior of the pressure jacket 210. The second proximal portion 360b may have an open end to allow the piston 138 of the fluid injector 10 to extend through the open end and engage rolling diaphragm syringe 135 held within throughbore 221. The rolling diaphragm syringe 135 may be inserted through the open end of the first distal portion 360a or the second proximal portion 360b.

In some aspects, the second proximal portion 360b has a locking lug or lip 370 protruding radially outward from an outer surface of the second proximal portion 360b. The locking lug or lip 370 may extend continuously or discontinuously around an outer circumference of the second proximal portion 360b. The locking lug or lip 370 is configured for interacting with corresponding features on the fluid injector 10 to releasably lock the pressure jacket 210 with the fluid injector 10. In some aspects, the locking lug or lip 370 may have a connection member to releasably secure the pressure jacket 210 to a corresponding locking mechanism of the fluid injector 10 described in U.S. Pat. Nos. 5,383,858; 5,873,861; 6,652,489; 9,173,995; and 9,199,033. Other connection members between the pressure jacket 210 and the fluid injector 10 are described in International Application No. PCT/US2015/057751, filed Oct. 28, 2015, or International Application No. PCT/US2015/057747, filed Oct. 28, 2015, which are hereby incorporated by reference.

Figure 16B:
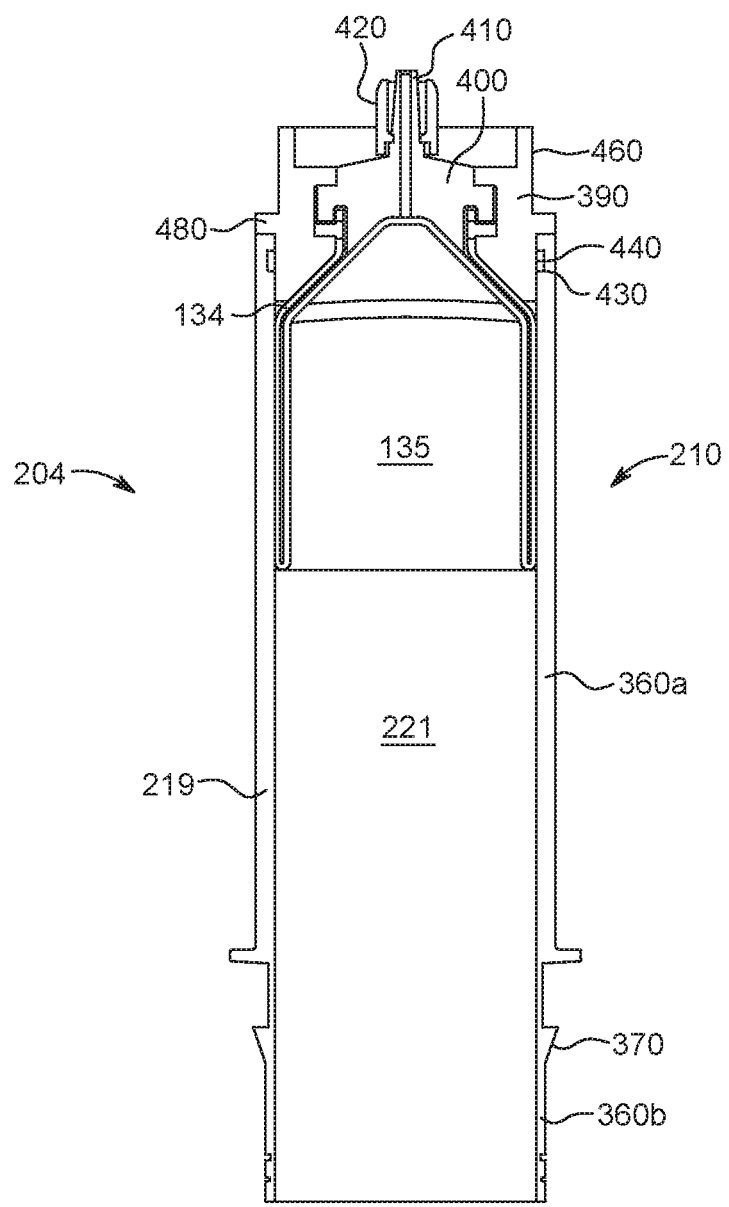
FIG. 16B is a cross-sectional side view of the rolling diaphragm syringe and the pressure jacket shown in FIG. 16A.
Figure 16C:
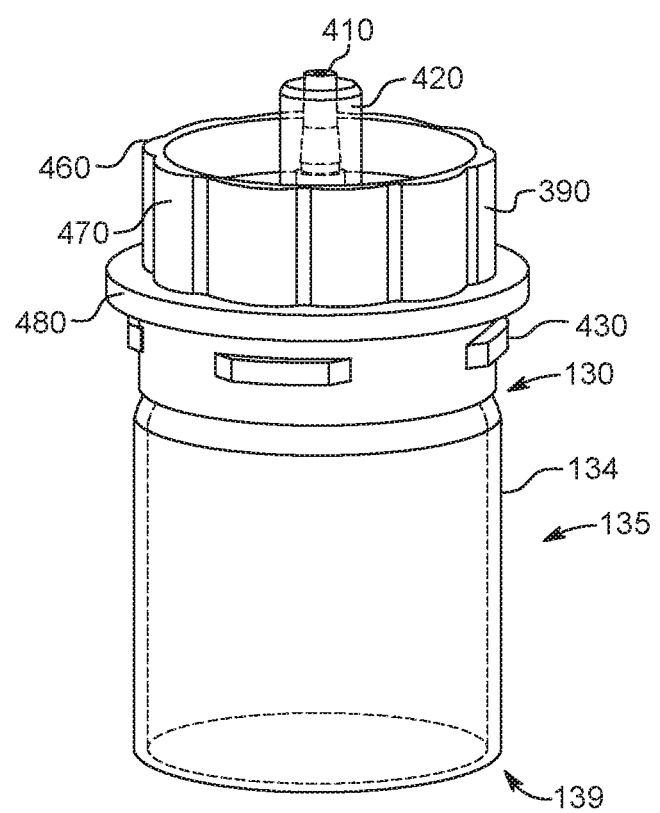
FIG. 16C is a perspective view of a rolling diaphragm syringe and a cap for use with the pressure jacket shown in FIG. 16A.

With reference to FIG. 16B and with continued reference to FIG. 16A, the pressure jacket 210 may have a cap 390 that is releasably secured to the distal end 216. In some aspects, the cap 390 may be secured by a threaded engagement, a bayonet fitting, or another mechanical fastening arrangement with the distal end 216 of the pressure jacket 210. For example, as shown in FIGS. 16B and 16C, the cap 390 may have at least one projection 430 that is received inside at least one groove 440 on the pressure jacket 210 such that the cap 390 may be locked with the pressure jacket 210 by aligning the at least one projection 430 to fit within the groove 440. The cap 390 may have an inner element 400 with a nozzle 410. The nozzle 410 may be in fluid communication with the interior volume of the rolling diaphragm syringe 135 (or directly formed on the rolling diaphragm syringe 135) to deliver fluid into or from the rolling diaphragm syringe 135. The nozzle 410 may have a connection member 420 for removably connecting to a connector of fluid path set 17 (shown in FIG. 1).

The annular sidewall 460 may have one or more gripping elements 470 (shown in FIG. 16C) to facilitate gripping of the cap 390 when the cap 390 is connected to and/or disconnected from the pressure jacket 210. The cap 390 may have a radial flange 480 that extends radially outward from a proximal portion of the annular sidewall 460.

With reference to FIG. 16C, at least a portion of the rolling diaphragm syringe 135 may be removably secured to the cap 390. In some aspects, the cap 390 may have a connection member that corresponds to and connects with the connection member 140a (shown in FIG. 15A) of the rolling diaphragm syringe 135. As further shown in FIG. 16C, the rolling diaphragm syringe 135 may initially be in a compressed configuration where the rolling diaphragm syringe 135 is rolled over on itself. Providing the rolling diaphragm syringe 135 in an initial compressed configuration may provide economic benefits during packaging and shipping by requiring less packaging material per syringe set up and/or allowing more syringe set-ups to be packaged.

2. Generating an Illuminated Identification Pattern with the Alternative Exemplary Syringe Having generally described the structure of the rolling diaphragm syringe 135, systems for generating an illuminated identification pattern with the rolling diaphragm syringe 135 to determine a fill status of the rolling diaphragm syringe 135 will be discussed in detail. In one example, with reference to FIGS. 17A and 17B, the piston 138 of the fluid injector 10 may have one or more electromagnetic radiation sources 212, such as LEDs, mounted to or embedded in a distal end thereof. When actuated, the piston 138 advances toward and engages the piston engagement portion 244 of the rolling diaphragm syringe 135. The LEDs emit light in the axial direction through the piston engagement portion 244 for producing an illuminated identification pattern at a distal end 137 of the rolling diaphragm syringe 135.

The wavelength of the electromagnetic radiation of the LEDs is chosen to match the material used to form the rolling diaphragm syringe to allow for the best transfer of energy. For example, the windows of a car are created from a material that prevents UV light from passing through to prevent sunburns while driving. The same principle holds true in the present application. The wavelength of the LEDs may be chosen to match the material used to manufacture the syringe to ensure maximum transmittance through the material of the piston engagement portion 244 and/or the wall thickness of syringe. Alternatively, instead of choosing the wavelength to match the material, a wavelength for the LEDs may be chosen that is the most visible to the human eye when combined with the halo effect described herein. For example, green light lies in the middle of the visible spectrum (approximately 532 nm) allowing light having such a wavelength to be readily visible to a technician. Also, depending on the solute concentration of the fluid contained within the syringe, along with the compounds present and their chemical properties, wavelengths for the LEDs can be selected to be selectively absorbed or transmitted by the fluid or having the desired reflection/dispersion properties. Accordingly, a wavelength of LEDs may be selected such that the light produced by the LEDs is dispersed by the fluid and generates more light therein, or the light may be absorbed/transmitted by the fluid and passes through similar to how the halo 120 is formed as described herein.

In other examples, the electromagnetic radiation source may be positioned in a variety of other locations such as, but not limited to, the piston engagement portion 244 of the rolling diaphragm syringe 135, the pressure jacket 210, external of the fluid injector 10 similar to the arrangement shown in FIGS. 10 and 11, a heat maintainer associated with the pressure jacket 210, or any other suitable location. In one example, with reference to FIGS. 18A and 18B, the electromagnetic radiation sources 212 may be positioned within another portion of the fluid injector, such as a clamp 213 positioned at the distal end of the syringe 135 used to secure the syringe 135 within the fluid injector. For instance, with reference to FIG. 18A, the electromagnetic radiation sources 212 may be positioned around a circumference of the side of the clamp 213 to direct light through the sides of the pressure jacket 210 to the syringe 135. Alternatively, with reference to FIG. 18B, the electromagnetic radiation sources 212 may be positioned on a top surface of the clamp 213 to direct light down through the syringe 135.

In one example, an end of the piston engagement portion 244 may be configured to expose the LEDs of the piston 138 when the piston 138 engages the piston engagement portion 244. More particularly, the piston engagement portion 244 may be configured to disengage a cover (not shown) to expose the LEDs when the piston 138 engages the piston engagement portion 244.

The piston engagement portion 244 of the rolling diaphragm syringe 135 may be shaped in a manner to collect light from the LEDs and direct light through the interior volume 214 of the rolling diaphragm syringe 135 towards the distal end thereof. For instance, the piston engagement portion 244 may have a convex lens shaped portion such that the portion focuses the light produced by the electromagnetic radiation sources 212 and directs the light up the piston engagement portion 244. In addition, if the light sources of the electromagnetic radiation sources are collimated, then the shape of certain portions of the piston engagement portion 244 may be flat or any other suitable geometrical shape.

The piston engagement portion 244 may also have a textured surface to enhance the light collecting and transmission capabilities thereof. In addition, the central portion 276 of the end wall 136 may also include a textured surface to enhance the transmission of light to the distal end 137 of the rolling diaphragm syringe 135 when the rolling diaphragm syringe 135 is filled with fluid, and diffuse light when the rolling diaphragm syringe 135 is filled with air or partially filled with air. Alternatively, central portion 276 of end wall 136 may be a lens to enhance transmission of light to the distal end 137 of the rolling diaphragm syringe 135.

Figure 19A:
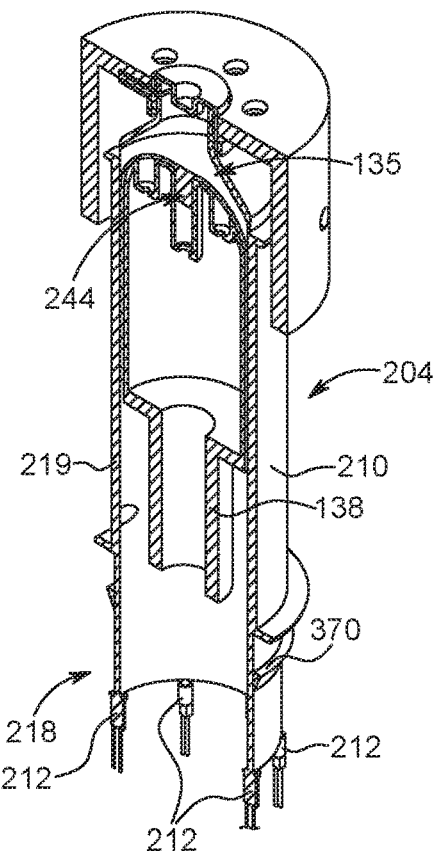
FIGS. 19A and 19B are a perspective cross-sectional view and cross-sectional view of a rolling diaphragm syringe and portions of an engagement mechanism illustrating a third configuration of an electromagnetic radiation source, according to aspects of the disclosure.
Figure 19B:
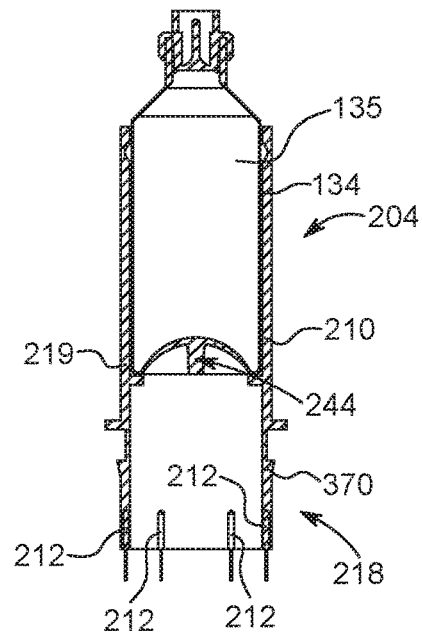

In another example, as shown in FIGS. 19A and 19B, the pressure jacket 210 may include the electromagnetic radiation source 212 as mentioned herein positioned at the proximal end 218 thereof. In such instances, the light produced by the electromagnetic radiation sources 212 may be directed up through the pressure jacket 210, and internal reflection within the pressure jacket 210 creates the illuminated identification pattern at the conical distal end 137 of the rolling diaphragm syringe 135 when the syringe is filled with fluid. In another aspect, the pressure jacket 210 may be coated with a substance that produces a "one way mirror" to properly distribute the internal reflection of the electromagnetic radiation while allowing observation by the technician. In addition or alternatively, the electromagnetic radiation source and the pressure jacket 210 may be polarized to prevent electromagnetic radiation from exiting pressure jacket 210.

Figure 20:
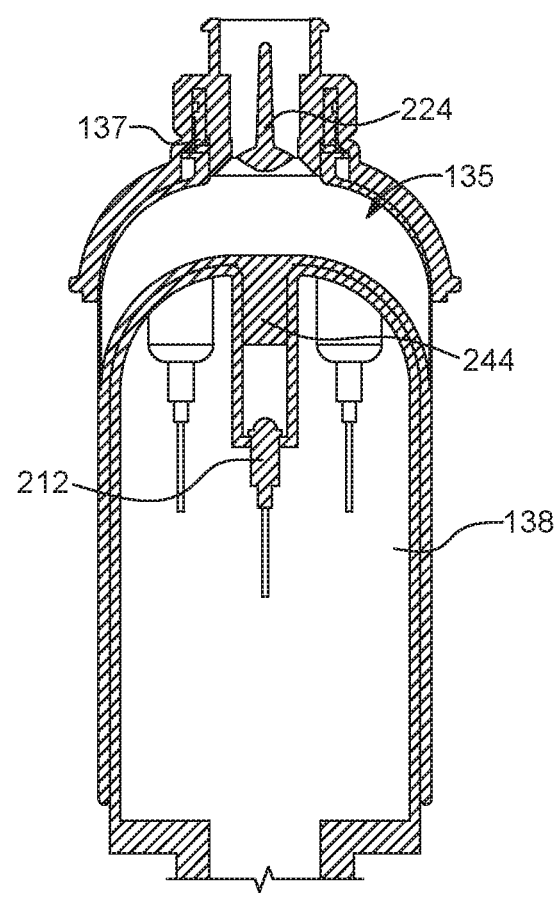
FIG. 20 is a cross-sectional view of the rolling diaphragm syringe and portions of the engagement mechanism illustrating a protruding element, according to an aspect of the disclosure.

The electromagnetic radiation is collected and directed towards the distal end 137 of the rolling diaphragm syringe 135 to create an illuminated identification pattern when filled with fluid. The inside of the distal end 137 of the rolling diaphragm syringe 135 may be angled similar to distal end 24 of syringe 12 discussed herein to generate a halo 120 in a similar manner. Alternatively or in addition, as shown in FIG. 20, a protruding component 224 may be incorporated in or positioned near the distal end 137 of the rolling diaphragm syringe 135 to distribute the light to generate the halo 120. The protruding component 224 may have various configurations for various purposes. For example, the protruding component 224 may be a reflective surface that reflects light in various directions to enhance visualization of the halo 120 or to show another indication that fluid is present. The protruding component 224 may be a prism, mirror, textured surface, or some other geometrical/material alteration to disperse/absorb light in such a way that it allows for indication of fluid presence, fluid type, or other characteristics of the syringe 135.

Since a cap 390 may be used with rolling diaphragm syringe 135 as described herein, the cap 390 may be manufactured from a translucent or transparent material so that the halo may be observed through the cap material. As the electromagnetic radiation is transmitted to the distal end 137 of the rolling diaphragm syringe 135, it causes such a transparent or translucent cap 390 to illuminate. The intensity of the illumination of the cap 390 varies depending on the fluid contained within the syringe as described herein. For instance, if a fluid is provided within the syringe, the cap 390 is illuminated much brighter than if air is present within the syringe.

II. Image Recognition of the Illuminated Identification Pattern and Various Other Aspects of the Fluid Injection System Having discussed various examples of radiation sources, syringes, how the electromagnetic radiation or light beam is directed through the syringe to form an illuminated identification pattern, sensors 114 for identifying the illuminated identification pattern and for monitoring or controlling operation of the injector 10 (shown in FIG. 1) based on identification of the illuminated identification pattern and various other aspects of the fluid injector 10 will now be discussed in detail. While the systems and methods discussed herein will be discussed with reference to the fluid injector 10 including the syringe 12, all of the concepts discussed herein may be utilized with the rolling diaphragm syringe 135 as well.

With reference to FIGS. 1, 6, and 9-12, the fluid verification system 110 is configured as an image recognition system that includes at least one sensor 114, such as an image capture device, positioned having a field of view directed to at least the distal end 24 of the syringe 12, a central processing unit 116 including a controller operatively connected to the sensor 114 and configured to process the images obtained from the sensor 114 using suitable image processing software, and a display 118 operatively connected to the central processing unit 116 for displaying the results of the image processing performed by the central processing unit. In one example, the image processing software may be the Insight Explorer software from Cognex Corporation of Natick, Mass. and the sensor 114 may be a DataMan 100 camera also from Cognex Corporation. In addition, the at least one sensor 114 and the central processing unit 116 may be integrated into a single component or provided as individual components. Further, the at least one sensor 114, the fluid injector 10, the display 118, and/or the central processing unit 116 may be in wired communication or may communicate wirelessly, for example via Bluetooth, WiFi, or other conventional wireless communication technology.

In another example, the sensors 114 can be an alternative type of optical sensor, such as an electromagnetic radiation detector or other suitable sensor as is known in the art. In some examples, the at least one sensor 114 is a digital camera that can be configured to obtain a digital image of at least the distal end 24 of the barrel 18 when the electromagnetic radiation source 112 is turned on. In other examples, the at least one sensor 114 can be an infrared radiation detector, ultraviolet light detector, ultrasound imaging device, or any other suitable sensor for identifying electromagnetic radiation emitted from the electromagnetic radiation source 112.

As will be appreciated by one of ordinary skill in the art, the at least one sensor 114 or detector can be adapted specifically for identifying a wavelength of electromagnetic radiation or light associated with the electromagnetic radiation source 112 and the illuminated identification pattern produced therewith. For example, the at least one sensor 114 can include various filters or tuned or attenuated optical elements for identifying only radiation within an expected wavelength (e.g., electromagnetic radiation within a wavelength emitted by the electromagnetic radiation source 112). Additionally, the syringe 12 itself can be used as a filter by altering the material properties (e.g., color, molecular alignment, pigment additive, polarized surface) to filter light of a given wavelength to achieve an optimized visualization by the user. Alternatively, image processing techniques, known in the art, can be used to remove portions of obtained images outside of the expected wavelength, thereby reducing an influence of ambient light and increasing sensitivity for the illuminated identification pattern.

Using features of the fluid verification system 110 described herein, various aspects of a fluid injection procedure can be monitored prior to and during delivery of a fluid to quickly provide information to a technician of details of the injection procedure in a readily apparent manner. These details of the injection will be discussed herein.

A. Air Detection

1. Using an Image of an Illuminated Identification Pattern

All current injector systems rely upon the personal inspection of the technician to determine if air is present in the syringe prior to the start of an injection procedure. The fluid verification system 110 is configured to provide detection of air using at least one sensor 114 and image recognition software executed by a central processing unit 116 to allow the technician to have additional corroboration of his/her conclusion on the status of the syringes. In addition, the technician can manually determine whether air is present by looking at the syringe to determine whether the illuminated identification pattern is present thus providing an alternative or two-pronged approach to air detection.

Figure 21:
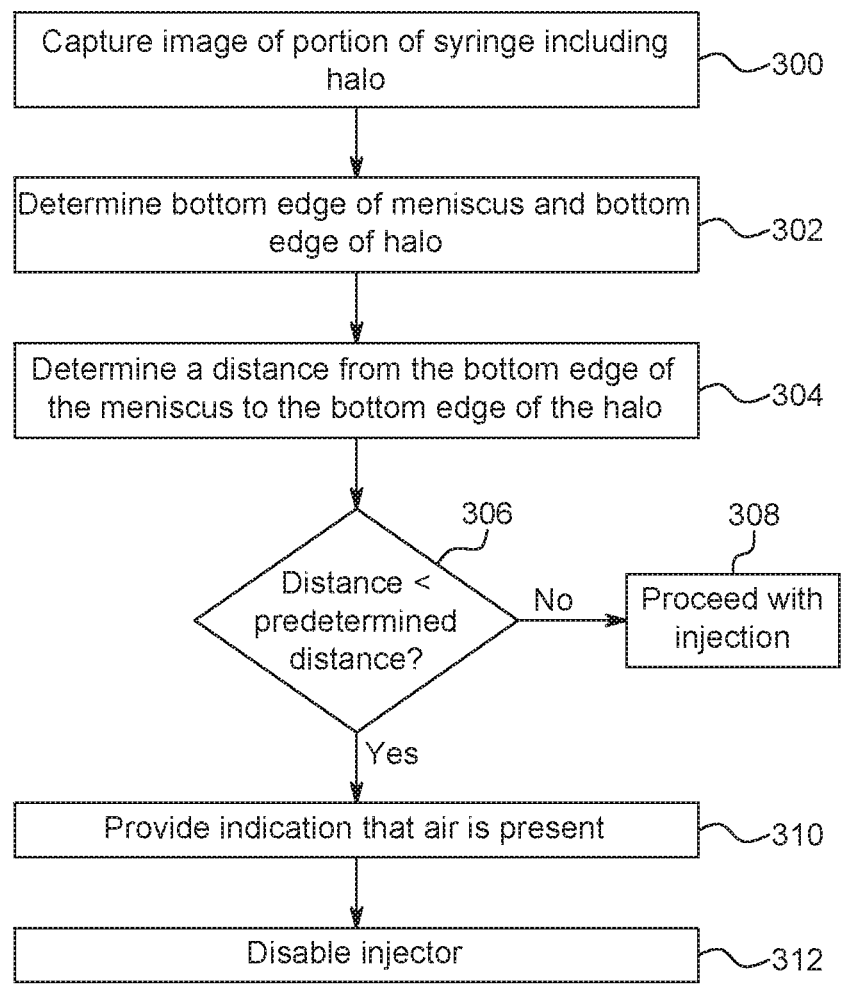
FIG. 21 is a flow chart of a method for determining presence of air within a syringe utilizing image processing techniques in accordance with an aspect of the present disclosure.

In one example, the fluid verification system 110 determines whether air is present by taking an image of the distal end of the syringe 12 to determine if the halo 120 has been generated in the syringe 12 by the electromagnetic radiation source 212 with the sensor 114 and using the image recognition software of the central processing unit 116 to review and analyze the image to measure one or more properties of the halo 120 or illuminated identification pattern to determine if the syringe is properly filled with fluid prior to injection. More specifically according to one aspect and with reference to FIG. 21, at step 300, the at least one sensor 114 is positioned to capture an image of at least a portion of the syringe 12 that includes the halo 120 or other illuminated identification pattern. Thereafter, and with reference to FIGS. 22 and 23, at step 302, a bottom edge 301 of a meniscus of the fluid contained within the syringe 12 and/or the bottom edge 303 of the halo 120 is measured or determined by the system 110. These edges 301, 303 are identified in the image by the software provided on the central processing unit 116. More specifically, the image processing software executed by the central processing unit 116 may be able to detect the edges through a variety of different methods. One method is to determine the change in contrast between neighboring pixels in the image of the edge. Alternatively, a contrast change over several adjacent pixels might indicate the presence of the edge. This change is indexed over each pixel within a search window to find areas where the contrast change reaches a threshold. For example, the change is flagged if the image recognition software finds a spot where a light colored pixel is adjacent to a dark pixel. If it is found that this threshold is crossed with several pixels in a row, oriented specifically in a predetermined direction, then the image processing software determines that this is an "edge". In this particular application, the dispersion of light caused by the lens effect of the meniscus causes a darkened area of fluid at the meniscus location. Specifically, there is an edge that can be found at the top and the bottom of the meniscus as shown most clearly in FIG. 23.

Figure 22:
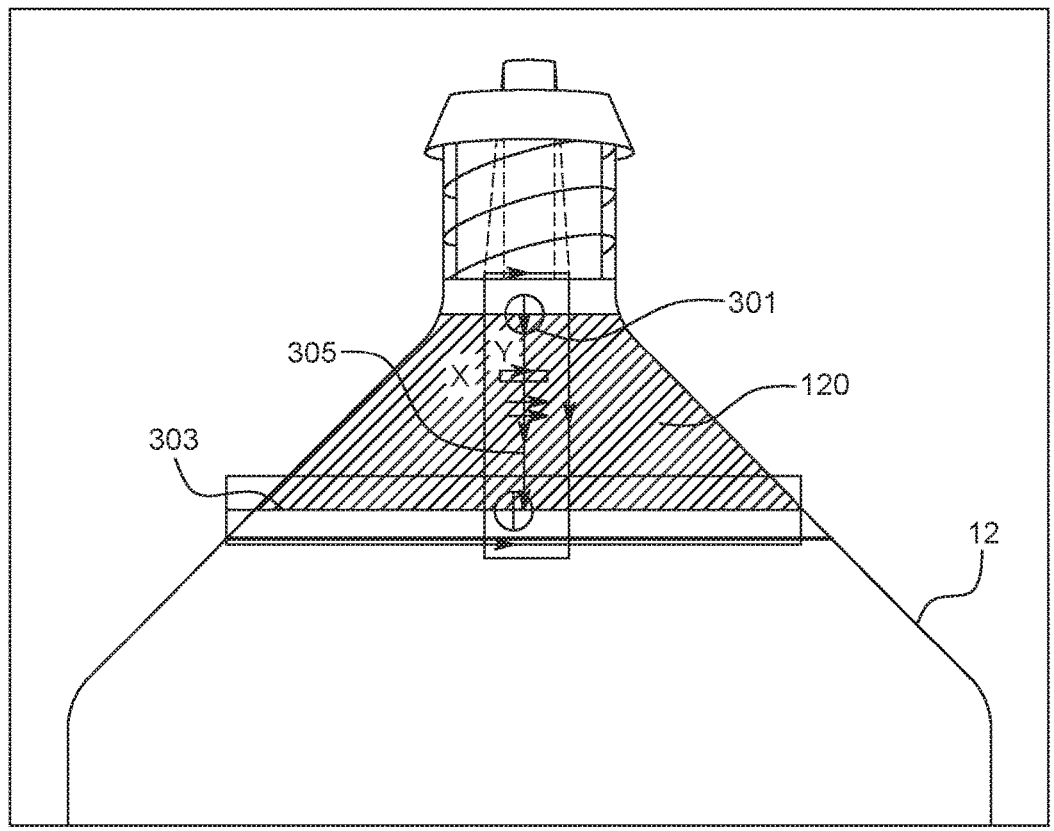
FIGS. 22 and 23 are drawings of exemplary images of a distal end of a syringe used in the method of FIG. 21.
Figure 23:
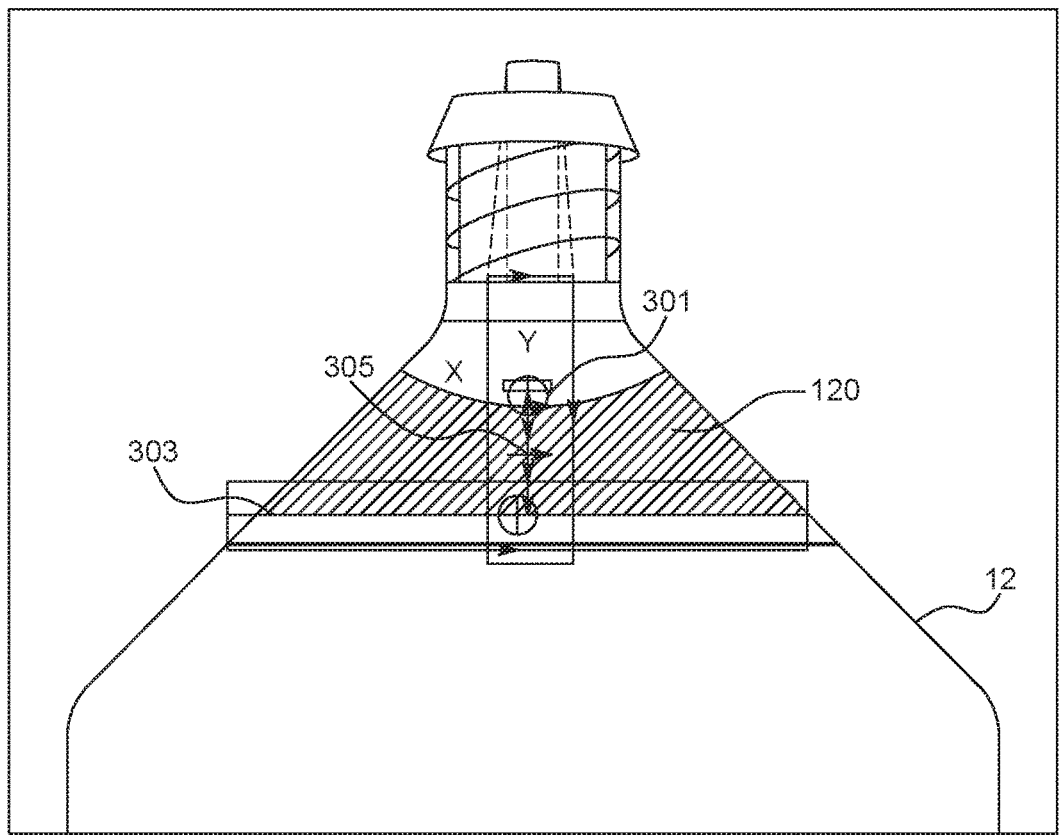

FIG. 22 is an image of a syringe 12 where no air is present, and FIG. 23 is an image obtained by sensor 114 where air is present in the syringe 12. As can be seen from these images, the halo 120 is larger when no air is present as shown in FIG. 22. This allows for the determination of air using imaging processing techniques as discussed in detail herein.

At step 304, a distance 305 from the bottom edge 301 of the meniscus to the bottom edge 303 of the halo 120 is determined using the image processing software provided on the central processing unit 116. Once the bottom edge 301 of the meniscus is determined, the location of this edge in space can be found. Specifically, the bottom edge 303 of the halo 120 can be determined and this bottom edge 303 of the halo 120 always stays fixed as long as the syringe 12 and the sensor 114 do not move. Accordingly, the image processing software is then able to determine a distance from the bottom edge 301 of the meniscus to the bottom edge 303 of halo 120.

Figure 24:
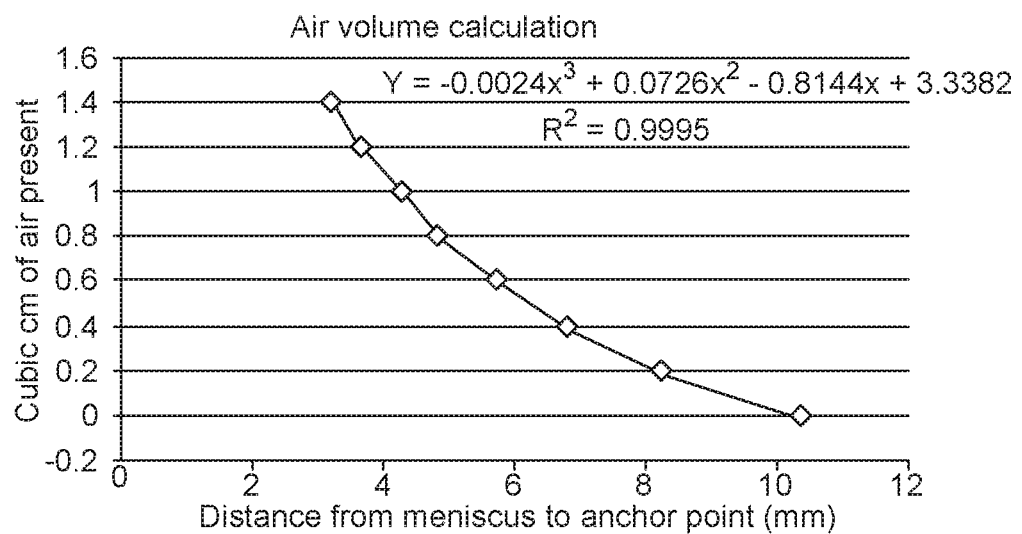
FIG. 24 is a graph illustrating the correlation between the presence of air and the size of the distance between the meniscus and the halo used in the method of FIG. 21

At step 306, the distance 305 determined in step 304 is compared to a predetermined distance. The predetermined distance was found by creating a curve, such as the curve shown in FIG. 24. This curve was created by taking a full syringe 12 and replacing known increments of fluid with equal volumes of air. Images were then taken after each increment of fluid was replaced and the distance from the bottom edge of the meniscus to the bottom edge of the halo 120 was measured using the image recognition software on the central processing unit 116. The curve is then plotted and an equation is fit. The equation is then provided to a logic algorithm in which the data of the curve in FIG. 24 is embodied to calculate the volume of air present based on the distance between the two edges.

If the measured distance 305 is greater than the predetermined distance, it can be determined that substantially no air is present and the injector can be armed to proceed with an injection at step 308. On the other hand, if the measured distance 305 is less than the predetermined distance, an indication that air is present in the syringe 12 is provided at step 310 and the fluid injector 10 is disabled from conducting an injection procedure at step 312. Alternatively, if air is present, the fluid injector 10 may perform a purge process to purge the air from the syringe and then repeat the measurement procedure of FIG. 21. This purge process may be repeated until the measuring process indicates that substantially no air is present in the syringe and the injection procedure may proceed.

2. Using Details Provided on the Barrel of the Syringe

Figure 25:
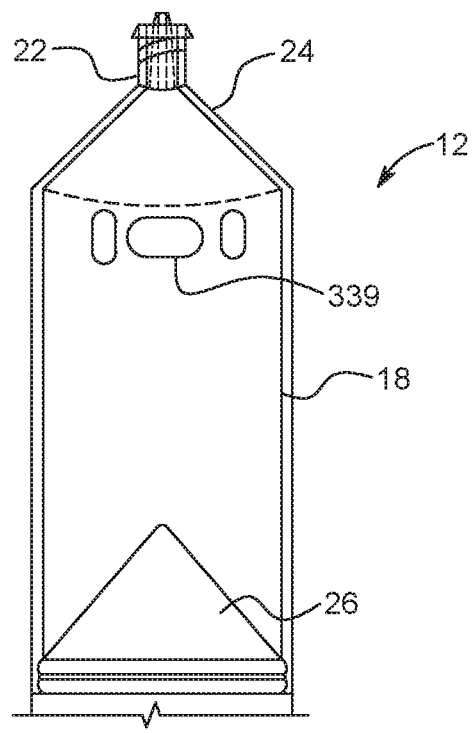
FIG. 25 is a schematic drawing of an alternative syringe for use with the injector of FIG. 1.
Figure 26:
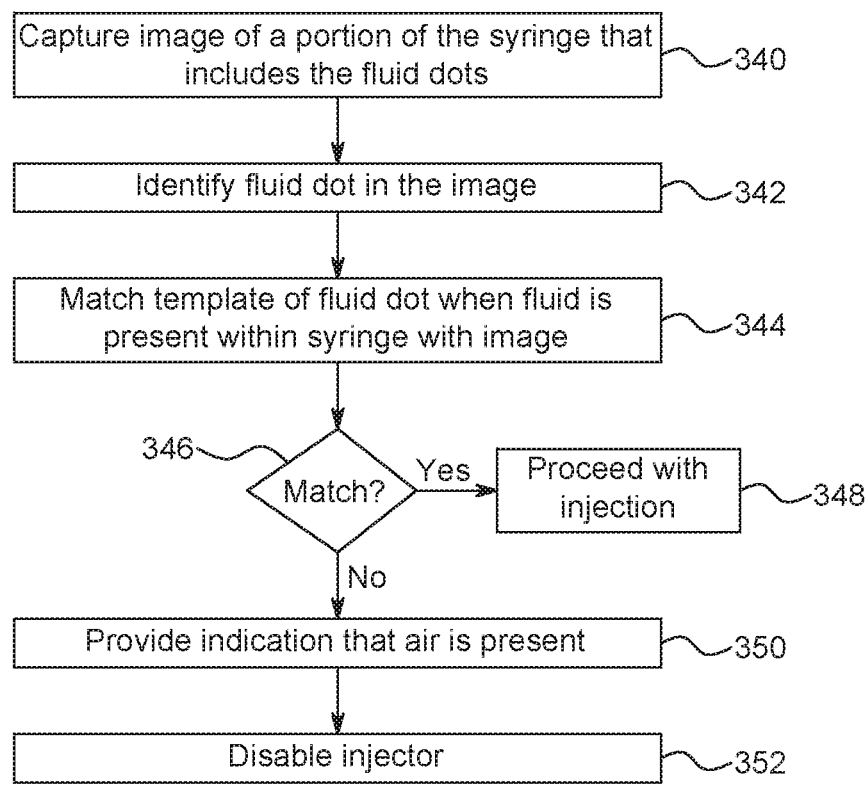
FIG. 26 is a flow chart of an alternative method for determining the presence of air within a syringe utilizing image processing techniques and the syringe of FIG. 25 in accordance with an aspect of the present disclosure.
Figure 27:
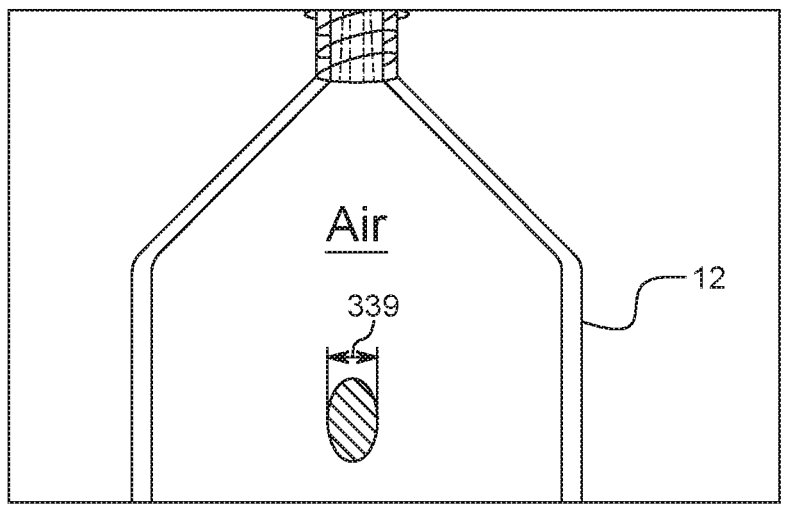
FIG. 27 is a drawing of an exemplary image of a distal end of a syringe containing air used in the method of FIG. 26.

An alternative approach to detecting air in a syringe using image processing techniques is to obtain an image of certain features provided on the barrel of the syringe. Specifically, and with reference to FIGS. 25 and 26, the syringe 12 may include at least one fluid dot 339 on the surface of the syringe 12 that is visible by the sensor through the fluid contained within the syringe 12. The use of fluid dots is described in U.S. Pat. No. 5,254,101, to Trombley, III, the disclosure of which is incorporated in its entirety by this reference. Due to the different properties of different fluids, this dot 339 will have a different appearance based on the fluid contained within the syringe. Accordingly, if air is contained within the syringe 12, the fluid dot 339 will have a certain configuration, such as an oval shape, when viewed in an image, which can be detected as followed. First, at step 340, the at least one sensor 114 is positioned to capture an image of at least a portion of the syringe 12 that includes the fluid dot 339 through the fluid contained within the syringe 12. Thereafter and with reference to FIG. 27, at step 342, the fluid dot 339 is identified in the image using pixel contrast thresholds. Specifically, the fluid dot 339 is identified by detecting the edges thereof in a manner similar to the manner in which the bottom edge of the meniscus is determined as described herein.

Next, at step 344, since the shape of the fluid dot 339 when various fluids are provided within the syringe are known, pattern matching techniques can be utilized to determine whether air or fluid is within the syringe 12. Accordingly, a template of a fluid dot 339 when fluid is present within the syringe can be matched to the image obtained in step 340. At step 346, if the template matches the image obtained in step 340, it can be determined that no air is present and the injector can be armed to proceed with an injection at step 348. On the other hand, if the template does not match, an indication that air may be present in the syringe 12 is provided at step 350 and the fluid injector 10 is disabled from conducting an injection procedure at step 352 until a repeated analysis step indicates that the air has been removed, for example by purging.

While fluid dots 339 were described herein as being utilized, various other shapes can be utilized and imaged to determine whether air is present in the syringe. This is due to the fact that a cylindrical syringe barrel is, in effect, a lens itself. Utilizing the curvature of the barrel wall, images can be captured which will appear different to the at least one sensor 114 if there is air or fluid in the syringe 12. This phenomenon can be utilized to detect the presence of gross air inside of a syringe. Additionally, the relative size of the image may allow for determination of fluid type within the syringe (e.g., larger image will be seen through contrast, while a small image will be seen through saline, for example, due to differences in index of refraction between the fluids). More specifically, since the syringe barrel 18 acts as a cylindrical lens when it is full of fluid, the fluid dots 339 stretch on the horizontal axis. Therefore, an oval shaped fluid dot 339 is stretched horizontally without impacting the vertical height. This is the way the oval fluid dot 339 on an empty syringe becomes a circle or more circular on a filled syringe to the sensor 114. The sensor may measure the change in the horizontal width of the fluid dot 339 to determine various features of the fluid contained within the syringe. Due to this principle a variety of different shapes may be used to achieve the above described effect of the fluid dots 339, for example by measuring differences in the non-vertical features of the fluid dots 339.

3. Using Brightness Measurements

Figure 28:
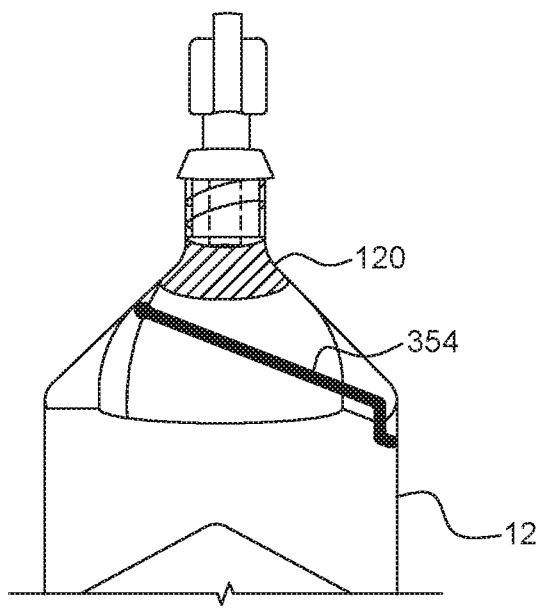
FIG. 28 is a drawing of an exemplary image used by an image recognition system to determine whether air is present within a syringe using brightness measurements in accordance with an aspect of the present disclosure.

According to other aspects, air detection is also possible by imaging a portion of syringe having electromagnetic radiation from a source thereof passing therethrough and determining the average pixel brightness value of a region of interest, such as a portion of the distal end 24 of the syringe, for example the halo region as described herein. Such an arrangement is illustrated in FIG. 28, for instance, which shows a syringe 12 filled with contrast having electromagnetic radiation, in the form of laser light beam 354, having a specific wavelength, passing therethrough. As can be seen in FIG. 28, when the syringe is filled with contrast, a path of a distinct laser beam 354 can be seen as it passes through the contrast. Without being limited by any theory, it is believed that the contrast agent dissolved in the solution scatters the electromagnetic radiation in the laser beam 354, providing an observable laser beam pathway. No such laser beam is present if the syringe 12 is filled with air (see FIG. 27). Accordingly, an average pixel brightness (e.g., 0-255 intensity units) in an image of the portion of the distal end 24 of the syringe 12 when filled with fluid, as shown in FIG. 28, is much higher than when the syringe is filled with air as evidenced by the presence of laser beam 354 due to scattered laser light. Accordingly, the presence of air or contrast can be determined using brightness by shining a laser electromagnetic radiation through a portion of the syringe barrel, obtaining an image of the syringe through which the electromagnetic radiation is being passed; determining a region of interest, such as near the distal end 24, of the syringe; determining the average pixel brightness value for the region of interest by assigning each 8 bit pixel within the region of interest a brightness value from 0-255 intensity units then averaging these brightness values; and comparing the average brightness value to a known brightness value to determine whether fluid or air is present within the syringe 12. Scattering of laser light by contrast, compared to non-scattering by air, may be observed by shining the laser light through any portion of the fluid in the syringe. In the aspect described herein, the laser light may be shown through the distal end of the syringe due to a particular location of the at least one sensor relative to the syringe barrel. One skilled in the art would recognize that other locations of the at least one sensor may be used to determine intensity of laser light depending on the location of the path of the laser light.

B. Fluid Differentiation

All of the above described image processing techniques for distinguishing air from fluid within a syringe may also be utilized to identify the type of fluid contained within a syringe. For instance, contrast can be accurately differentiated from saline and different types of contrast can be accurately differentiated from each other using the above described imaging processing techniques due to the manner in which different fluids interact with light. In particular, with reference to FIGS. 29 and 30, scattering of the laser light may differ according to the fluid within the syringe. For example, laser beam path 354 displays a weak intensity passing through saline compared to intensity of a laser beam path 354 passing through contrast in a syringe.

1. Utilizing the Illuminated Identification Pattern

Figure 29:
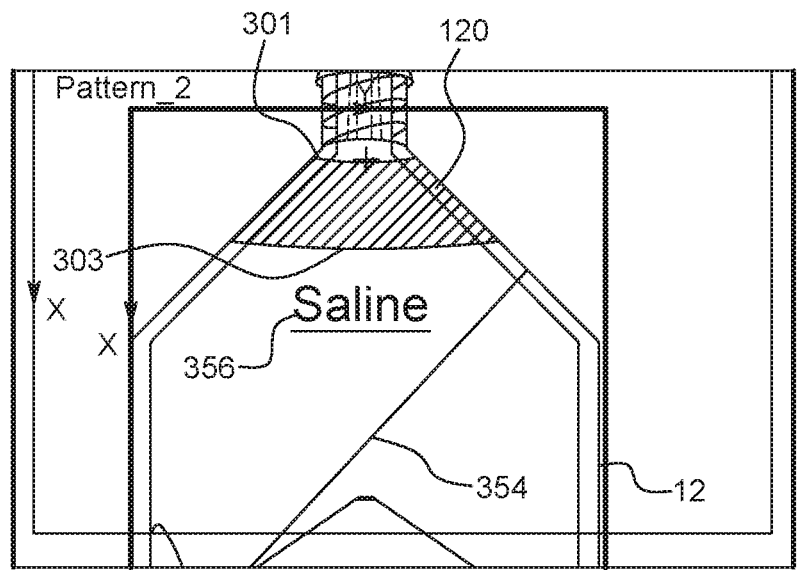
FIGS. 29 and 30 are drawings of exemplary images used by an image recognition system to determine the type of fluid contained within a syringe in accordance with an aspect of the present disclosure.
Figure 30:
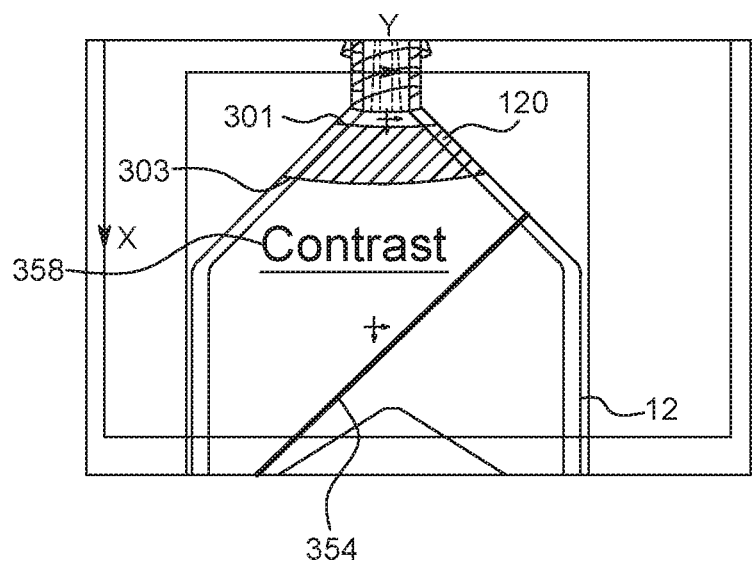

With further reference to FIGS. 29 and 30, the fluid verification system 110 according to various aspects herein may determine whether a syringe contains saline or contrast by taking an image of the halo 120 generated in the syringe 12 by the electromagnetic radiation source 112 with the sensor 114 and using the image recognition software of the central processing unit 116. While other methods for differentiation between saline and contrast are described in detail herein, the same technique may be used to differentiate between different types or concentrations of contrast. First, the at least one sensor 114 is positioned to capture an image of at least a portion of the syringe 12 that includes the halo 120. Thereafter, a distance between a bottom edge 301 of a meniscus at the air/fluid interface within the syringe 12 and the bottom edge 303 of the halo 120 is measured by the system 110. These edges 301, 303 are identified in the image by the software provided on the central processing unit 116 from pixel contrast thresholds as described herein. FIG. 29 is an image obtained by sensor 114 of a syringe 12 containing saline and FIG. 30 is an image obtained by sensor 114 where contrast is present in the syringe 12. As can be seen from these images, the distance between edges 301 and 303 is greater (FIG. 29) when saline is present in the syringe compared to the distance between edges 301 and 303 when contrast is present in the syringe (FIG. 30). With respect to differentiation of contrast, the halo 120 will also be a different size depending on the type of contrast that is present in the syringe. This allows for differentiation of the type of fluid—saline, and various contrast agents—contained in the syringe using imaging processing techniques as discussed in greater detail herein.

A distance from the bottom edge 301 of the meniscus between the air/fluid interface and the bottom edge 303 of the halo 120 is determined using the image processing software provided on the central processing unit 116 as described herein. Then, this distance may be compared to various predetermined distances corresponding to various fluids contained within the memory of the central processing unit 116. If the distance corresponds to the first predetermined distance for saline, an indication 356 that saline is contained in the syringe 12 is automatically displayed on the display 118, and if the distance corresponds to the second predetermined distance for a specific contrast, an indication 358 that the specific contrast is contained in the syringe 12 is automatically displayed on the display 118.

Alternatively, pattern matching techniques based on the halo 120 size may be utilized to determine whether the syringe contains air, saline, or various contrast agents. For instance, the image processing software provided on the central processing unit 116 can determine a height of the halo 120 from the bottom of the threads of nozzle 22 to the bottom edge of the halo 120 and determine the presence and fluid type based on the height as described in detail herein. In addition, the image processing software may also be programmed for specific contrast agents or other fluids utilizing pattern recognition by taking a training image of a syringe known to have a particular contrast contained therein. This training image records all of the dimensions of the halo 120 including height. Then, the image processing software compares all of the features of later images it captures to the training image for comparison. If the images exceed a threshold of similarity then the system will provide an indication that the syringe 12 contains contrast or saline other than the contrast it has been trained for.

2. Using Details Provided on the Barrel of the Syringe

Figure 31:
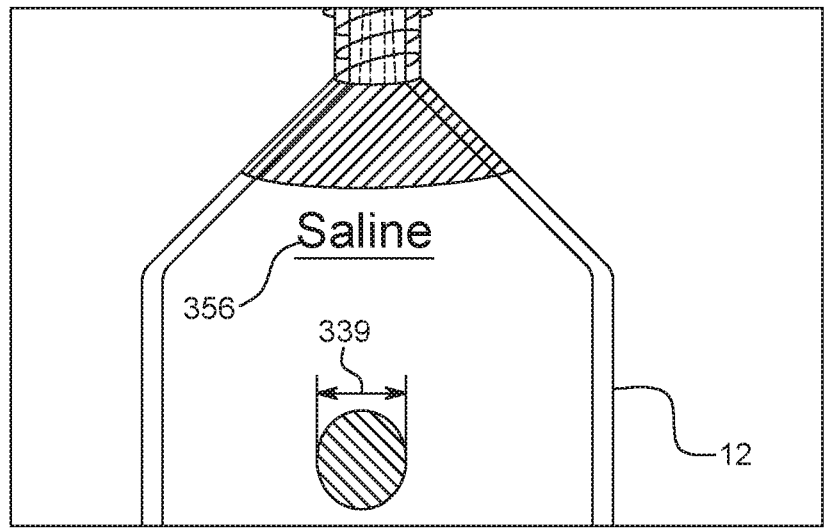
FIGS. 31 and 32 are drawings of alternative exemplary images used by an image recognition system to determine the type of fluid contained within a syringe in accordance with an aspect of the present disclosure.
Figure 32:
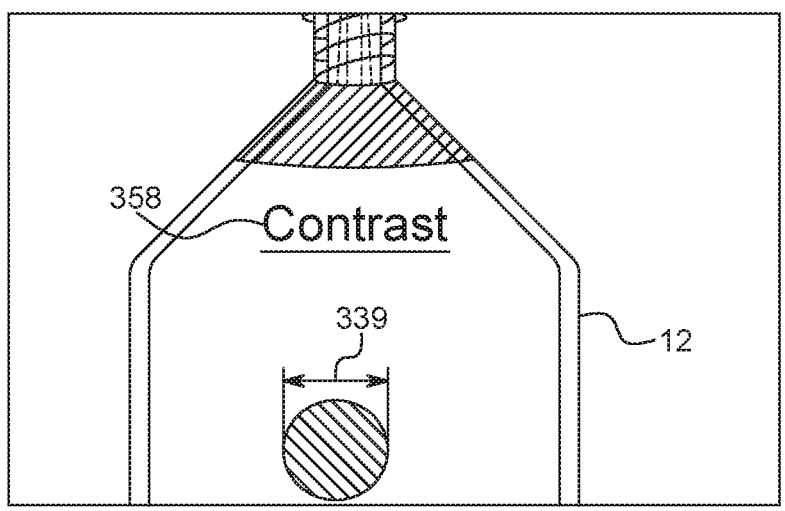

An alternative approach to determining the type of fluid contained within a syringe using image processing techniques is to obtain an image of certain features provided on the syringe. Specifically, and with reference to FIGS. 27, 31 and 32, the syringe 12 may include at least one fluid dot 339 that is visible by the sensor through the air or fluid contained within the syringe as described herein. Due to the different properties of air and different fluids, this dot 339 will have a different appearance, specifically along a horizontal axis, based on air or the fluid contained within the syringe as seen by comparing the fluid dot 339 of FIG. 27, seen through a syringe 12 containing air, the fluid dot 339 of FIG. 31, which is seen through a syringe 12 containing saline, and the fluid dot 339 of FIG. 32, which is seen through a syringe 12 containing contrast. Accordingly, if air is contained within syringe 12, the fluid dot 339 will have a more shorter distance in the horizontal direction when viewed by the sensor, if saline is contained within the syringe 12, the fluid dot 339 will have a certain configuration when viewed in an image and if contrast is contained within the syringe 12, the fluid dot 339 will have a certain configuration (i.e., longer distance in the horizontal direction) when viewed in an image. Therefore, the type of fluid contained within the syringe can be detected as follows.

First, the sensor 114 is positioned to capture an image of at least a portion of the syringe 12 that includes the fluid dot 339 or other indicator feature on the syringe barrel through the fluid contained within the syringe 12. Thereafter, the fluid dot 339 is identified in the image using pixel contrast thresholds as described herein. Next, at step 344, since the shape of the fluid dot 339 when various fluids are provided within the syringe are known, pattern matching techniques can be utilized to determine whether air, saline or contrast is present within the syringe 12. For example, a template of a fluid dot 339 when saline is present within the syringe can be matched to the image. If the template matches the image, it can be determined that saline is present and an indication 356 that saline is present in the syringe 12 is provided on the display 116. On the other hand, if the template does not match, a template of a fluid dot 339 when contrast is present within the syringe can be matched to the image. If the template matches the image, it can be determined that contrast is present and an indication 358 that contrast is present in the syringe 12 is provided on the display 118. Further if the template for saline or various contrasts do not match, a template for a fluid dot 339 when air is present within the syringe can be matched to the image. If air is determined to be in the syringe, the injection procedure may be halted automatically.

Various other shapes, other than oval fluid dots 339, can be utilized and imaged to determine the type of fluid contained within the syringe as described in greater detail herein.

3. Using Brightness Measurements

According to certain aspects, fluid differentiation may also be possible by imaging a portion of syringe having electromagnetic radiation from a source thereof passing therethrough and determining the average pixel brightness value of a region of interest, such as a portion of the distal end 24 of the syringe. Returning to FIGS. 27, 29, and 30, when the syringe is filled with contrast (see FIG. 30), a distinct laser beam path 354 can be seen. The laser beam path 354 is much less distinct if the syringe 12 contains saline (see FIG. 29) and is essentially indiscernible when passing through a syringe filled with air. According to certain embodiments, a laser that emits light having wavelengths within the green region of the visible light spectrum may be used. Accordingly, an average pixel brightness (e.g., 0-255 intensity units) in an image of the portion of the distal end 24 of the syringe 12 when filled with contrast is much higher than when the syringe is filled with saline or air. Accordingly, the type of fluid contained within the syringe can be determined by obtaining an image of the syringe through which the electromagnetic radiation is being passed; determining a region of interest of the syringe, such as near the distal end 24 (although other regions of the syringe may be used); determining the average pixel brightness value for the region of interest by assigning each 8 bit pixel within the region of interest a brightness value from 0-255 intensity units then averaging these brightness values; and comparing the average brightness value to a known brightness value to determine whether contrast, saline, or air is present within the syringe 12. This methodology may also be used to differentiate between different types (e.g., brands or solute concentration) of contrast.

C. Fluid Source Status

According to other aspects, by using the at least one sensor 114 to obtain images of various portions of the fluid injector 10, various information regarding the status of fluid sources can be obtained. For example, an image of a fluid container, such as a saline bag or contrast bottle, and its contents can be obtained and the amount of fluid within the bottle can be determined using image processing techniques. This information can be provided to the central processing unit and a bottle may be displayed on display 118 illustrating the amount of fluid present or remaining within the bottle. In addition, optical character recognition may be used to determine the type of fluid contained within the bottle and this information can also be displayed on the display 118. Moreover, in certain aspects the fluid remaining in the bottle may be constantly monitored prior to, during, and after an injection procedure and the updated remaining volume may be displayed real-time on the display 118. In still other aspects, the central processing unit 116 may monitor the remaining volume and provide a warning if the volume of one or more of the contrast or saline are not sufficient to complete an injection procedure. This feature may be combined with a patient schedule for a series of patients to provide real-time feed-back on the required volume of contrast and/or saline so that a technician may be sure to have sufficient supply on hand to complete all scheduled injection procedures and may, for example when a contrast warmer is used, ensure that the subsequent container(s) of contrast is at the desired injection temperature when the contents of the currently used bottle are almost used up.

More specifically, the same methodology utilized for recognizing the size of the halo 120 with pattern recognition techniques described herein may be utilized for determining fluid source status. For example, the image processing software looks for geometrical components in the image to compare to training images with known objects. In one example, if the image processing software is trained to know what the letters of the alphabet look like and the size and angular thresholds for recognition are lowered, then the image processing software is effectively able to read the label of the bottle and determine the manufacturer, contrast type, expiration dates, etc. Additionally, the fluid level within the bottle can be identified using edge detection techniques described herein and the image processing software can be programmed to calculate the volume remaining in the bottle until it needs to be replaced by a user. This aspect utilizes similar calculations as used with the volume of air present in the syringe as described herein. Specifically, a curve may be generated and an equation fit for each of the bottle sizes and shapes or an algorithm may be developed to determine remaining volumes.

D. Determination of Syringe Type (Size/Presence)

Figure 33:
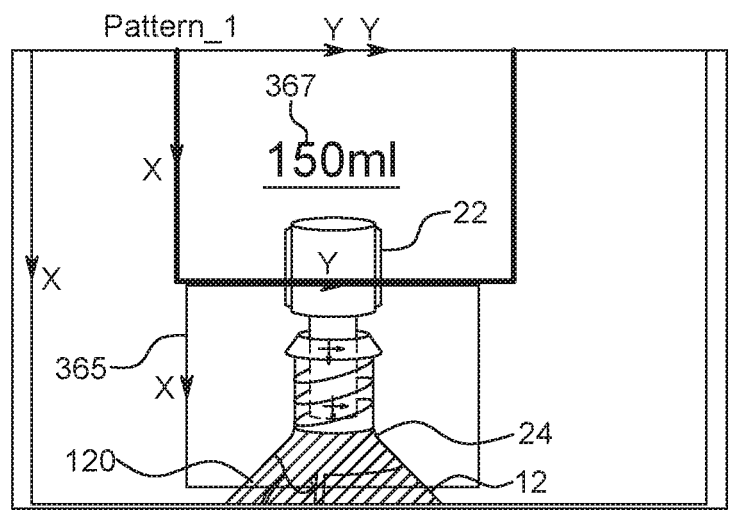
FIGS. 33 and 34 are drawings of exemplary images used by an image recognition system to determine the size of a syringe in accordance with aspects of the present disclosure.
Figure 34:
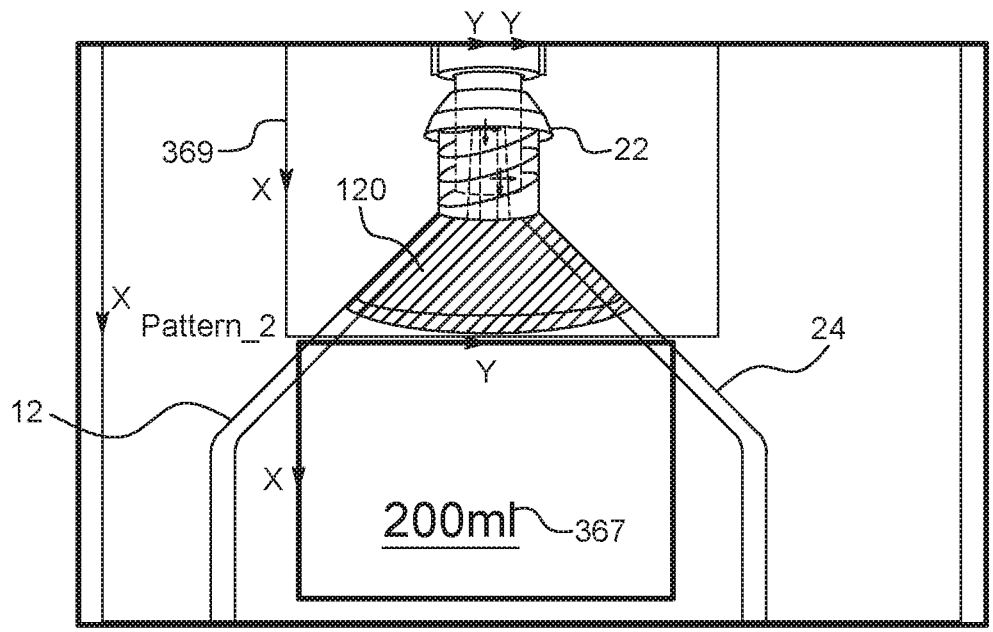

In certain aspects, the fluid verification system 110 may also be utilized to determine various properties or parameters of the syringe 12 inserted into the injector, for example, syringe type, size, manufacturer, manufacturing date or lot number, suitability for a specific injection procedure, prior use, remaining use lifetime, maximum pressure, etc., prior to a fluid injection procedure. This information may be used to identify the syringe and manufacturer, determine whether the syringe is previously used, and determine desired flow rates, pressures, volumes, etc. In one example, with reference to FIGS. 33 and 34, the size of the syringe may be determined as follows. First, the at least one sensor 114 is positioned to capture an image of at least a portion of the syringe 12 such as the distal end 24 of the syringe 12. Since the position of the at least one sensor 114 is known, the location of certain features of a syringe 12 of a first size, such as the nozzle 22 or the halo 120, and the location of certain features of a syringe 12 of a second size, such as the nozzle 22 or the halo 120, in the image of the distal end 24 of the syringe are also known. Using this fact, pattern matching techniques can be utilized to determine the size of a syringe 12 used with the fluid injector 10. For example, a template 365 of a syringe of a first size (e.g., 150 mL) can be applied to the image. If the template matches the image, the central processing unit 116 can determine that the syringe is a 150 mL syringe and an indication 367 of the size of the syringe 12 is provided on the display 118. On the other hand, if the template 365 does not match, a template 369 of a syringe of a second size (e.g., 200 mL) can be applied to the image. If the template matches the image, the central processing unit 116 can determine that the syringe is a 200 mL syringe and an indication 367 of the size of the syringe 12 is provided on the display 118. If none of the stored templates match, an indication can be provided on the display 118 that no syringe is present or that the syringe identity cannot be determined. In another aspect, the at least one sensor 114 may be located in a position to image at least one identification marking on syringe 12, such as a bar code containing information on the syringe, such as for example, manufacturer, manufacturing date or lot, one or more syringe parameters, a specific identity/security code that can be confirmed by the central processing unit to determine if the syringe is authentic or is potentially being reused, etc., and transmit the image of the identification marking to the central processing unit 116 for deconvolution.

E. Tubing Presence Indicator

Figure 35:
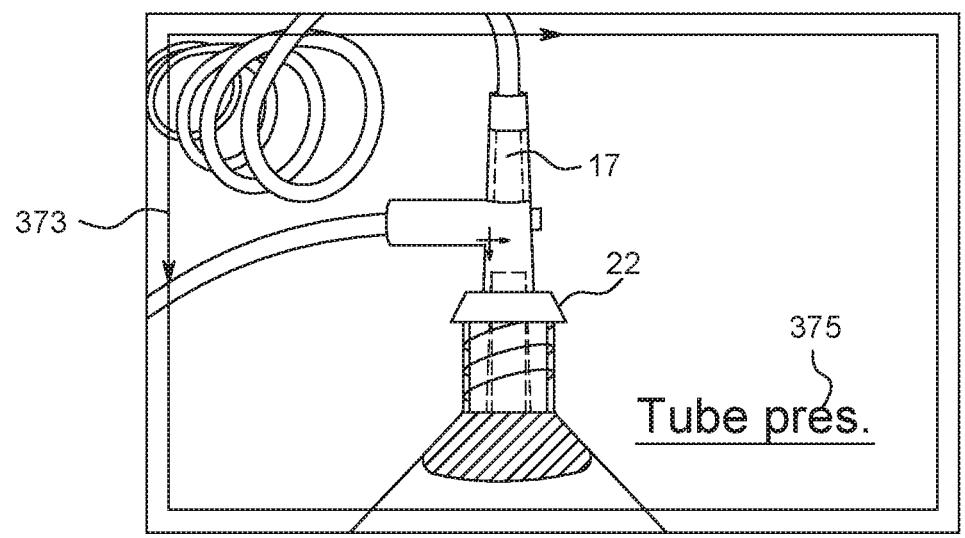
FIGS. 35 and 36 are drawings of exemplary images used by an image recognition system to determine whether a fluid path set is connected to a syringe in accordance with an aspect of the present disclosure.
Figure 36:
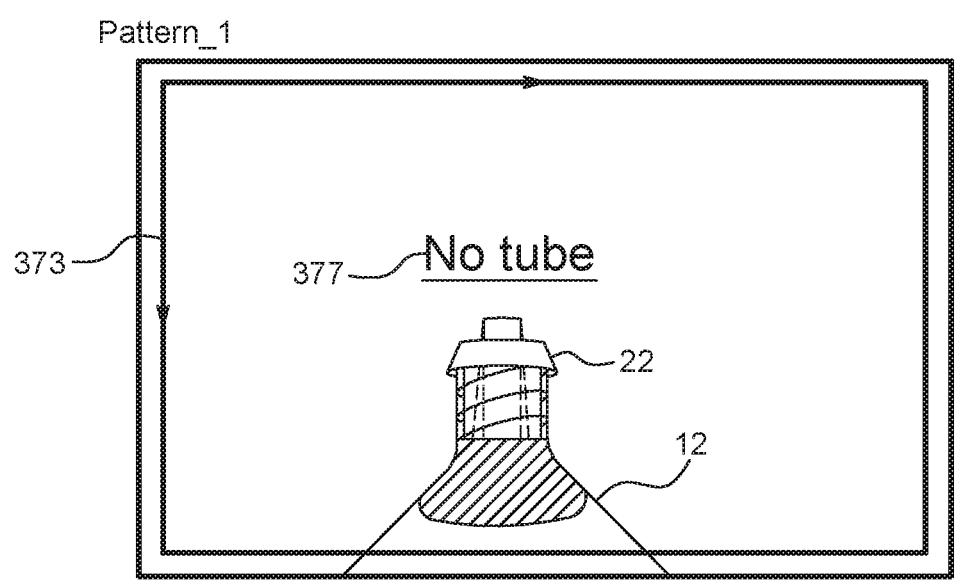

Similar to the determination of the syringe type, in other aspects the presence or absence of a fluid path set 17 connected to the syringe 12 can also be determined using imaging processing techniques. This information can be utilized by the central processing unit 116 to disable the injector if an operator inadvertently attempts to start an injection procedure without a fluid path set 17 being connected to the nozzle 22 of the syringe or if the fluid path set has not been primed. In one example, with reference to FIGS. 35 and 36, the sensor 114 is positioned to capture an image of the nozzle 22 of the syringe 12. Since the position of the sensor 114 is known, the location of certain features of the syringe 12, such as the nozzle 22 and the fluid path set 17, if connected to the nozzle 22, in the image of the syringe 12 are also known. Using this fact, pattern matching techniques can be utilized to determine whether a fluid path set 17 is connected to the syringe 12. For example, a template 373 of a syringe 12 having a fluid path set 17 connected thereto can be applied to the image. If the template matches the image, the central processing unit 116 can determine that the fluid path set 17 is connected to the syringe 12 and an indication 375 that the fluid path set 17 is present is provided on the display 118 (see FIG. 31). On the other hand, if the template 373 does not match, the central processing unit 116 can determine that no fluid path set 17 is present and an indication 377 that no fluid path set 17 is present is provided on display 118.

F. Spike or Transfer Set Presence Indicator

Figure 37:
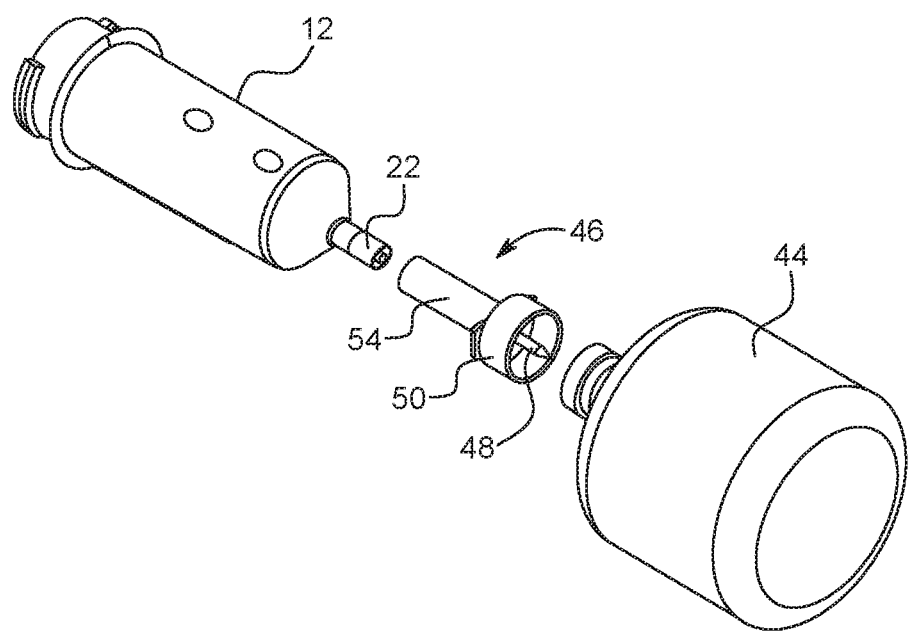
FIG. 37 is a perspective view of a fluid transfer system including a fluid transfer device for transferring fluid from a fluid container into a syringe in accordance with an aspect of the present disclosure.

With reference to FIG. 37, according to certain aspects, a fluid transfer device 46 is often used to fill a syringe 12 from a fluid container 44. The transfer device 46 typically includes a spike 48 having at least one fluid path, and in certain aspects an air passage, for puncturing the seal of the fluid container 44, a container holder or cup 50 for holding the fluid container 44 on the spike 48, a valve (not shown), such as a check valve, for allowing fluid to enter the syringe 12 and a syringe support member or sleeve 54 for holding the syringe 12 in relationship to the transfer device 46.

During a filling procedure, after the syringe 12 is mounted on the fluid injector 10, the plunger 26 is advanced to expel air from the syringe 12. The syringe 12 is then ready to be filled with fluid. The transfer device 46 may then be inserted onto the fluid container 44 such that the spike 48 pierces the seal of the fluid container 44. The syringe support member 54 of the transfer device 46 may then be placed over the nozzle 22 of the syringe 12. Within the support member 54, the luer tip of the syringe 12 engages and actuates the valve to open a passage for fluid to flow from the container 44 to the syringe 12. To aspirate the contents of the fluid container 44 into the syringe 12, the injector piston (not shown) retracts the plunger 26 of the syringe 12. After filling the syringe 12, the fluid container 44 is removed from the transfer device 46. Filling of the syringe with fluid may be monitored, for example in real-time, by the at least one sensor 114 to ensure accurate filling of the syringe.

Figure 38:
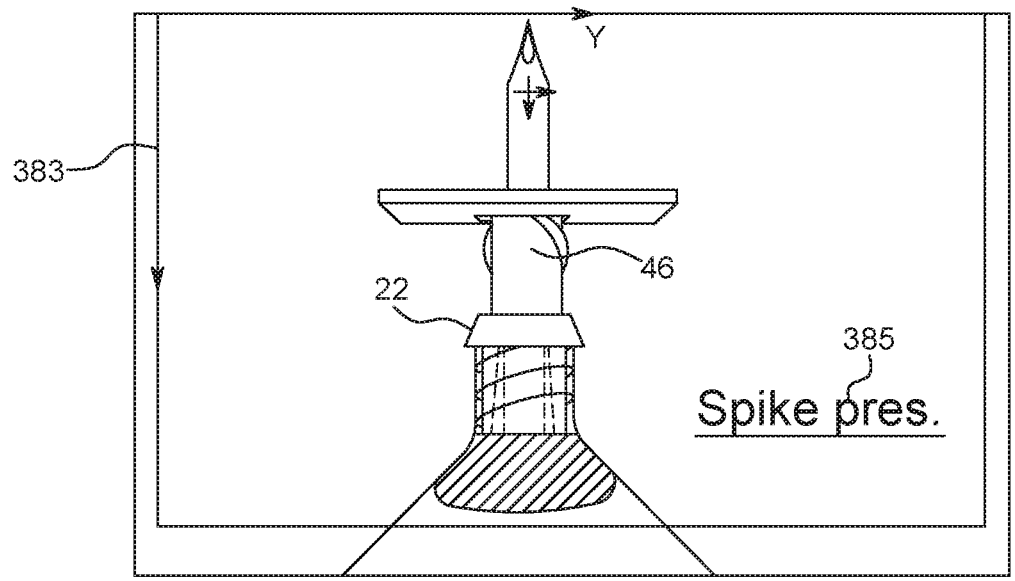
FIGS. 38 and 39 are drawings of exemplary images used by an image recognition system to determine whether a fluid transfer device is connected to a syringe in accordance with an aspect of the present disclosure.
Figure 39:
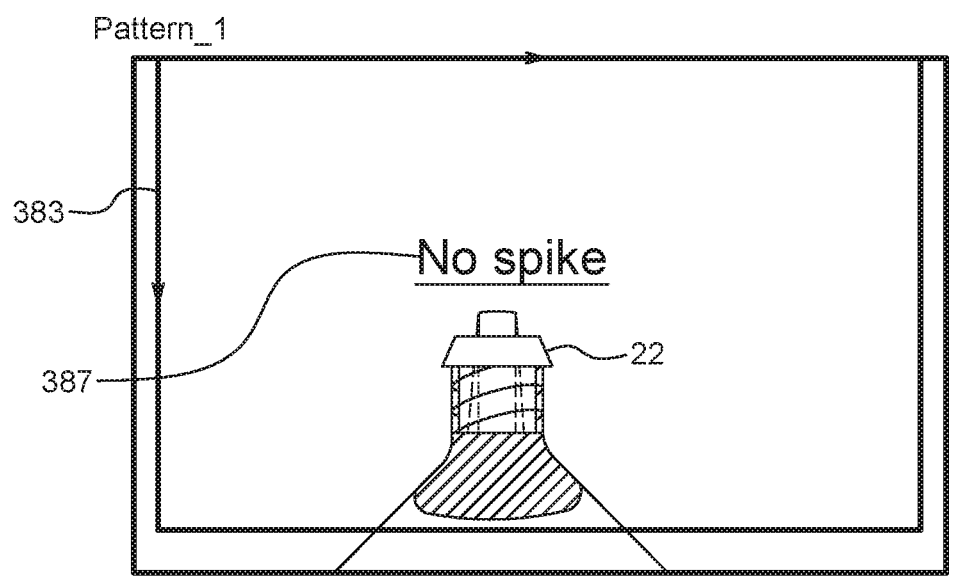
Figure 58:
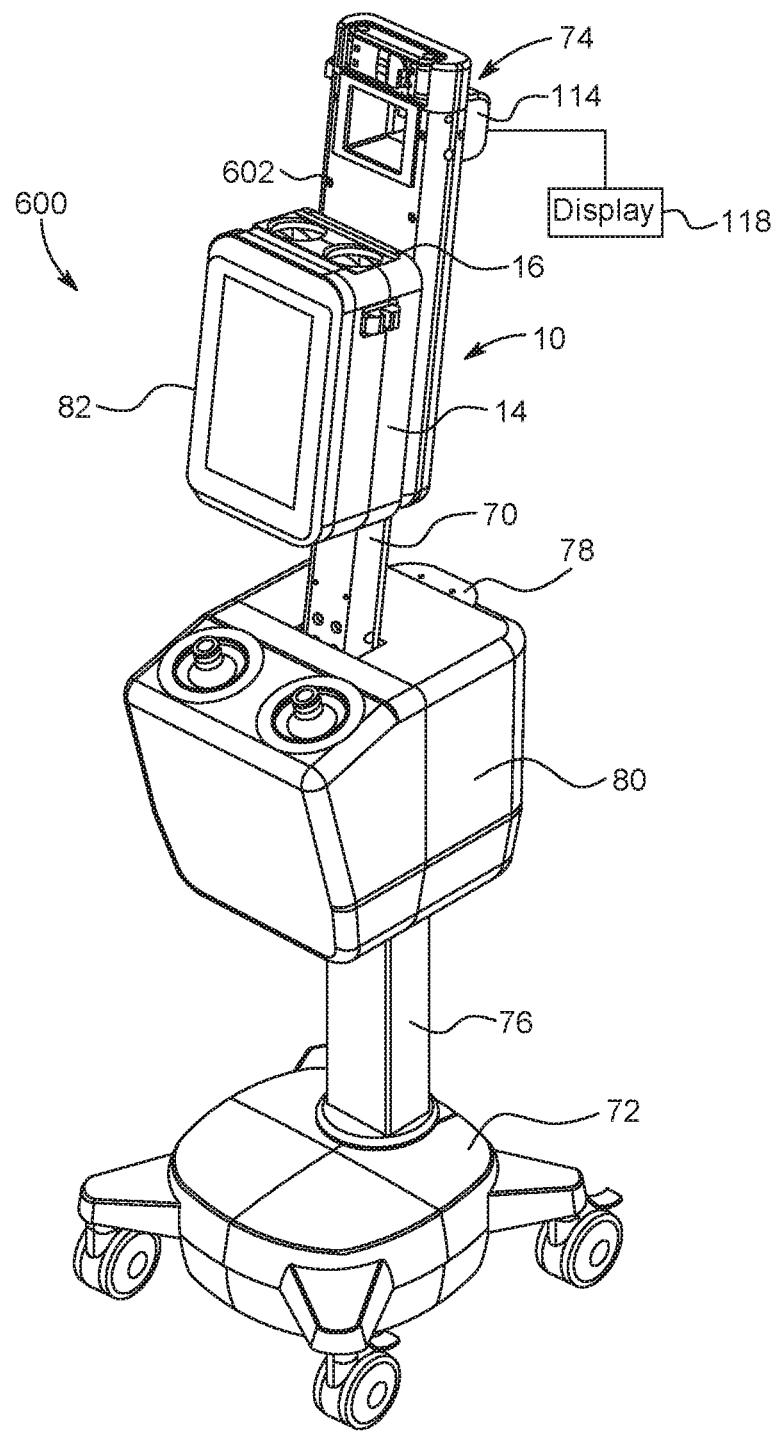
FIG. 58 is a front perspective view of a fluid injection system in accordance with an aspect of the present disclosure.

Once filling is complete, it may be desirable for the operator to be provided with an indication of whether the fluid transfer device 46 has been removed. This can be automatically done using the fluid verification system 110 described herein. Specifically, with reference to FIGS. 38 and 39, the at least one sensor 114 is positioned to capture an image of the nozzle 22 of the syringe 12. Since the position of the at least one sensor 114 is known, the location of certain features of the syringe 12, such as the nozzle 22 and the fluid transfer device 46, if connected to the nozzle 22, in the image of the syringe 12 are also known. Using this fact, pattern matching techniques can be utilized to determine whether a fluid transfer device 46 is connected to the syringe 12. For example, a template 383 of a syringe 12 having a fluid transfer device 46 connected thereto can be applied to the image. If the template matches the image, the central processing unit 116 can determine that the fluid transfer device 46 is connected to the syringe 12 and an indication 385 that the fluid transfer device 46 is present is provided on the display 118 (see FIG. 38). This information may also be displayed on a touch screen controller 82 of a fluid injection system 600 as shown in FIG. 58. On the other hand, if the template 383 does not match, the central processing unit 116 can determine that no fluid transfer device 46 is present and an indication 387 that no fluid transfer device 46 is present is provided on the display 118 (see FIG. 39).

G. Tubing Purged Indicator

Figure 40:
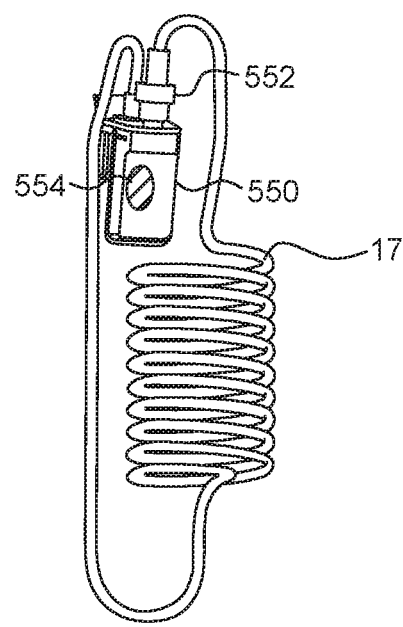
FIG. 40 is a perspective view of a purge container connected to a fluid transfer set in accordance with an aspect of the present disclosure.

With reference to FIG. 40, in certain aspects of the fluid injectors 10 described herein, a purge container 550 may be configured to be connected to the end of a connector 552 of the fluid path set 17 that delivers contrast media or other fluid to a patient during a purging procedure prior to an injection. When the fluid path set 17 is primed or purged of air prior to an injection procedure, the purge container 550 may collect the discharge of contrast media from the end of the fluid path set 17 that delivers the media to the patient when the syringe 12 and fluid path set 17 are purged and primed and provide an indication that the purge is acceptable based on the amount of contrast contained therein. In certain aspects, an operator may visually inspect the purge container 550 to determine that an acceptable amount of contrast is contained therein and that the purge was acceptable and the syringe and fluid path are primed with fluid. However, in certain aspects this process may be automated by capturing an image of the purge container 550 with the at least one sensor 114 and processing the image using the image processing techniques discussed herein.

Figure 41:
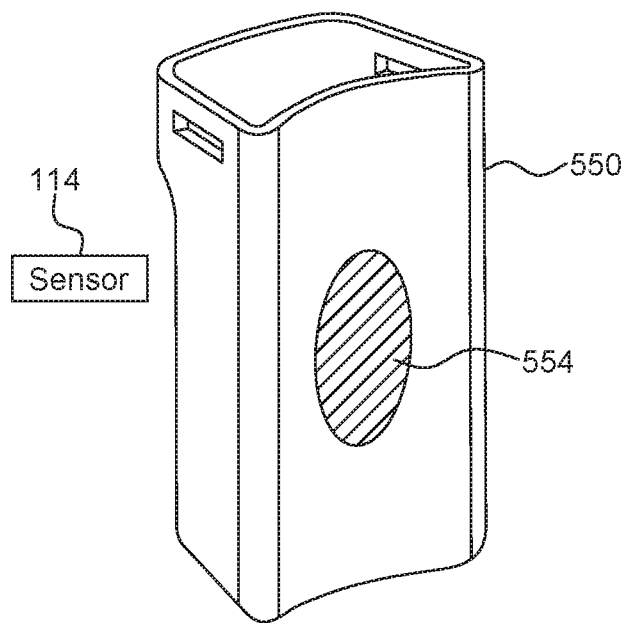
FIG. 41 is a perspective view of the purge container of FIG. 40.
Figure 42A:
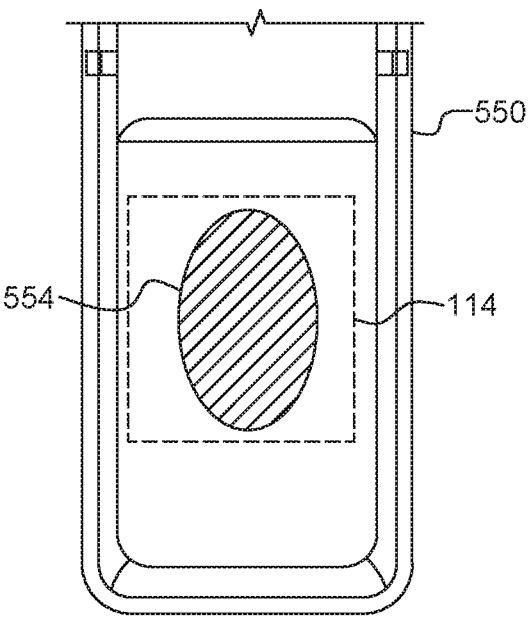
FIG. 42A is a front plan view of the purge container of FIG. 40 with no fluid contained therein.
Figure 42B:
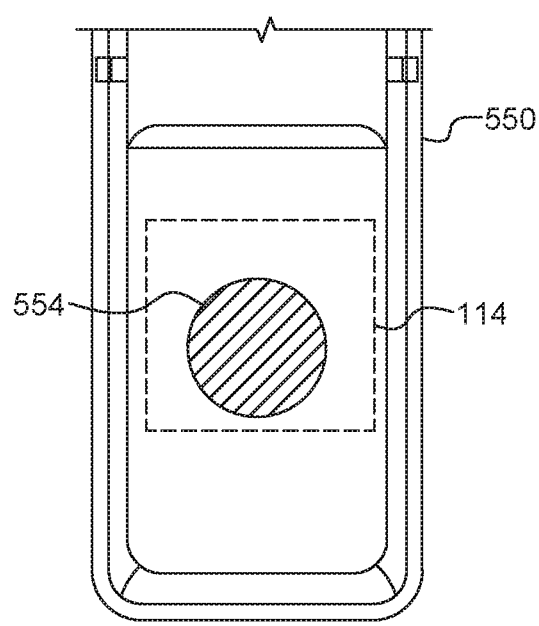
FIG. 42B is a front plan view of the purge container of FIG. 40 with fluid contained therein.

For instance, with reference to FIGS. 41, 42A, and 42B, a fluid dot 554 or other indicator marking, similar to the fluid dot 339 discussed herein, may be formed or provided on a surface of the purge container 550. The at least one sensor 114 is positioned such that it will image the fluid dot 554 through any fluid contained within the purge container 550. Due to the different properties, such as index of refraction, of different fluids and/or the selected curvature of the purge container 550, this dot 554 will have a different appearance based on the fluid contained within the syringe and purge container 550. Accordingly, if air is contained within the purge container 550, the fluid dot 554 will have a first configuration when viewed in an image, for example according to one aspect as shown in FIG. 42A and, if a fluid, such as contrast or saline, is contained within the purge container 550, the fluid dot 554 will have a second configuration, for example as shown in FIG. 42B. The configuration of the fluid dot 554 can be detected as followed. First, the at last one sensor 114 is positioned to capture an image of at least a portion of the purge container 550 that includes the fluid dot 554 through the fluid contained within the purge container 550 after the syringe and tubing set 17 have been primed and purged of air. Thereafter, since the shape of the fluid dot 554 when various fluids are provided within the purge container 550 are known, pattern matching techniques can be utilized to determine whether air or fluid is within the purge container 550. Accordingly, a template of a fluid dot 554 when a certain fluid, such as contrast or saline, is present within the purge container 550 can be matched to the image of the fluid dot 554 obtained by the sensor 114. If the template matches the image, it can be determined that no air is present in the syringe and tubing set 17 and that purge container 550 contains sufficient fluid to indicate that the system has been primed and a signal can be sent to the fluid injector 10 that the fluid path set 17 has been properly purged and primed. An indication may also be provided on display 118 that the fluid path set 17 has been properly purged and primed and that the injector is ready for the injection procedure. According to certain aspects, the priming and purging of the syringe and fluid path set may be monitored real-time. In this aspect, the at least one sensor 114 monitors the fluid dot 554 on purge container 550 as the configuration of the fluid dot 554 changes during the priming procedure, thus monitoring the change in volume of the purge container 550 and indicating when sufficient fluid has been primed into the system and no additional air remains in the system. According to one aspect, an algorithm may be utilized that correlates volume change in purge container 550 with fluid flow through tubing set 17 to confirm completion of the priming operation.

Figure 43A:
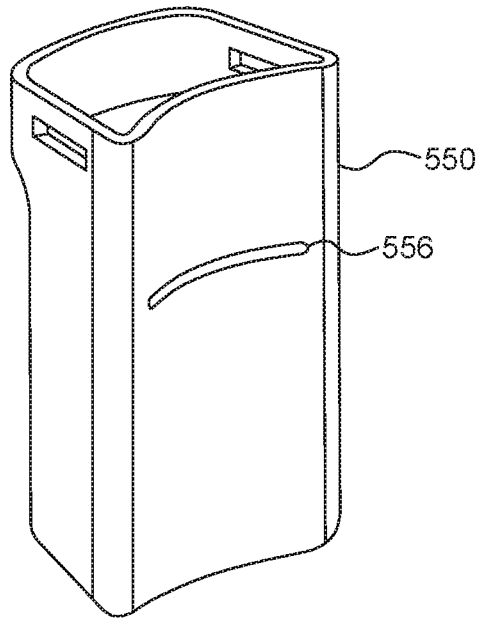
FIG. 43A is a perspective view of an alternative configuration of the purge container of FIG. 40 with no fluid contained therein.
Figure 43B:
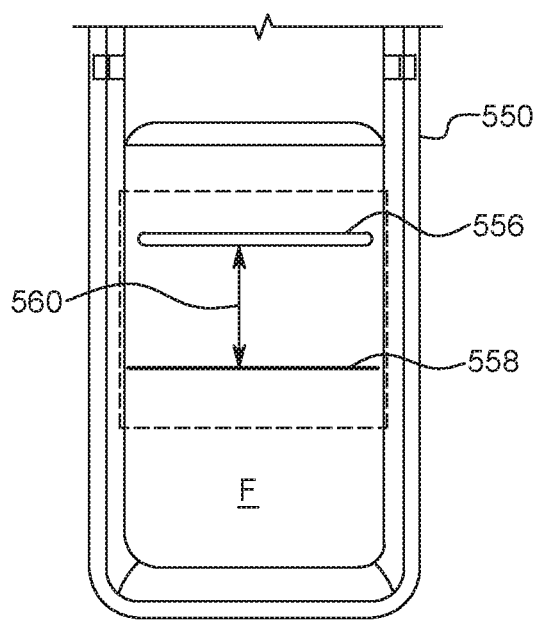
FIG. 43B is a front plan view of the purge container of FIG. 43A with fluid contained therein.

Alternatively according to another aspect, with reference to FIGS. 43A and 43B, rather than using a fluid dot 554, one or more reference lines 556 may be formed or provided on a surface of the purge container 550. The reference line 556 may be printed on the surface of the purge container 550, molded onto the surface of the purge container 550, or formed or provided on the surface of the purge container 550 in any other suitable manner. The at least one sensor 114 is positioned such that it will image the reference line 556 through any fluid contained within the purge container 550. Once an image of the purge container 550 is obtained, the image processing software provide on central processing unit 116 identifies a top edge 558 of the fluid F contained within the purge container 550 along with the reference line 556 using pixel contrast thresholds as described herein. A distance 560 from the top edge 558 of the fluid F contained within the purge container 550 to the reference line 556 is determined using the image processing software provided on the central processing unit 116. The central processing unit 116 compares this distance 560 to various predetermined distances corresponding to acceptable and unacceptable purging processes to determine if the purge is acceptable and the system is primed. Again, the purge/prime operation and change in volume in the purge container 550 may be monitored real-time as the syringe and fluid path set 17 are primed to ensure accurate priming of the system.

Figure 44A:
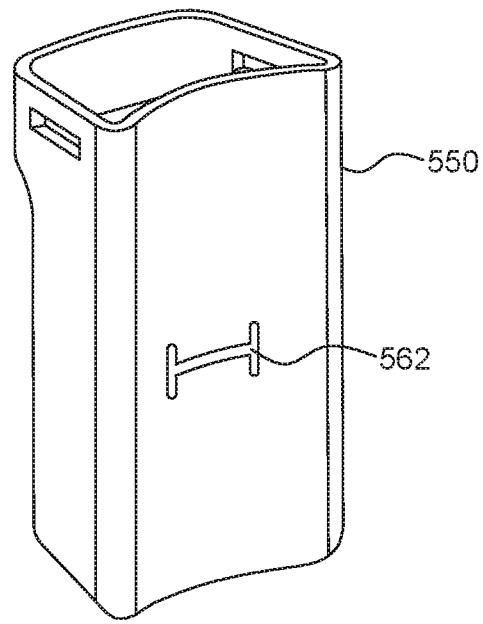
FIG. 44A is a perspective view of another alternative configuration of the purge container of FIG. 40 with no fluid contained therein.
Figure 44B:
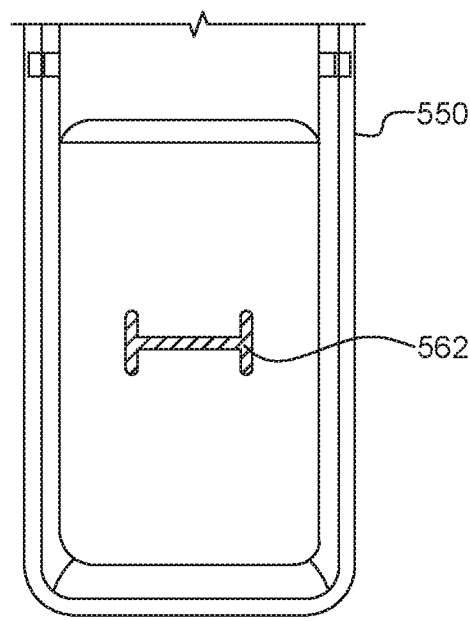
FIG. 44B is a front plan view of the purge container of FIG. 44A with fluid contained therein.

In yet another alternative, with reference to FIGS. 44A and 44B, an indicator line 562 having the shape shown may be formed or provided on a surface of the purge container 550. The indicator line 562 may be printed on the surface of the purge container 550, molded onto the surface of the purge container 550, or formed or provided on the surface of the purge container 550 in any other suitable manner. The sensor 114 is positioned such that it will image the indicator line 562 through any fluid contained within the purge container 550. Due to the properties of different fluids and/or the selected curvature of the purge container 550, the indicator line 562 appears to be a different length in an image when fluid is present as compared to when air is present. In addition, the indicator line 562 may have a brighter appearance when viewed in air than when viewed in fluid. Accordingly, pattern matching techniques and/or brightness level measurement of the indicator line 562 can be performed on an image of the indicator line 562 by the image processing software on the central processing unit 116 to determine whether fluid or air is present within the purge container 550. Based on this determination, the central processing unit 116 can determine the acceptability of the purge and provide an indication, via display 118, to an operator. Again, the purge/prime operation and change in volume in the purge container 550 based on changes in indicator line 562 may be monitored real-time as the syringe and fluid path 17 are primed to ensure accurate priming of the system. One of skill in the art will recognize that other configurations of the indicator line 562 are possible and that the image recognition software and algorithms described herein may monitor changes in the configuration of the indicator line 562 during a purging/priming operation and indicate to the technician that the system has been correctly primed and is ready for use in an injection procedure. Such other configurations are within the scope of this disclosure.

Figure 45:
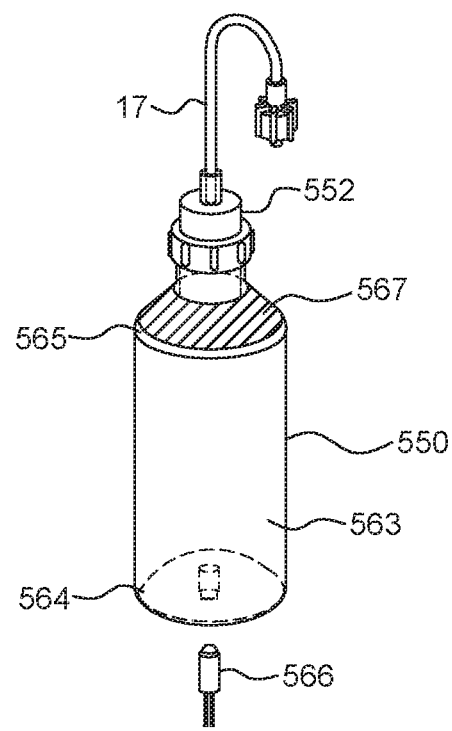
FIG. 45 is a perspective view of an example of a purge container connected to a fluid transfer set in accordance with an aspect of the present disclosure.

With reference to FIG. 45, an alternative configuration of the purge container 550 is illustrated. This purge container 550 is also configured to be connected, during a purging procedure, to the end of a connector 552 of the fluid path set 17 that is designed to deliver contrast media or other fluid to a patient during a subsequent diagnostic injection procedure. The purge container 550 includes a cylindrical body 563 having a proximal end 564 and a tapered distal end 565 similar to the tapered distal end 24 of the syringe 12 described herein. An electromagnetic radiation source 566, such as an LED, is positioned beneath the proximal end 564 of the cylindrical body 563. Accordingly, when the purge container 550 is filled with an appropriate amount of fluid, a halo 567 is generated similar to the manner in which halo 120 is formed within the syringe 12 as described herein. This allows the operator to quickly and easily determine if an acceptable amount of contrast is contained therein and that the purge was acceptable if the halo 567 is present and that the syringe and fluid path set 17 are appropriately primed. In addition, this process may be automated, and in certain aspects monitored real-time, by capturing one or more image of the halo 567 generated within the purge container 550 with at least one sensor 114 and processing the image using the image processing techniques discussed herein.

Figure 46:
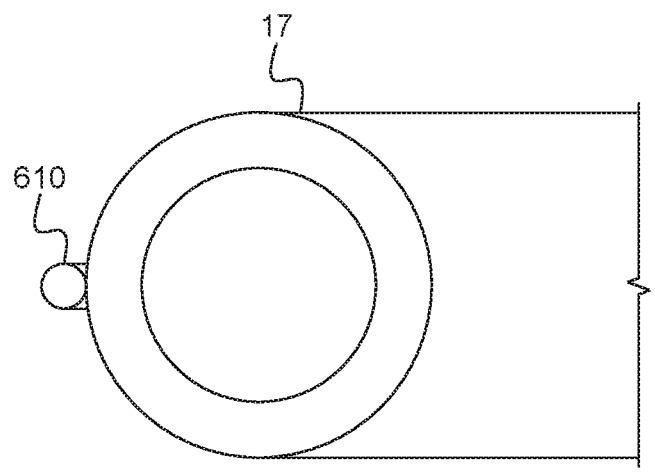
FIG. 46 is a front view of an end of tubing used with the fluid transfer set in accordance with an aspect of the present disclosure.

With reference to FIG. 46, according to an aspect, the fluid path set 17 may be altered to allow for image recognition of an image of the tubing obtained by at least one sensor 114 to determine whether the fluid path set 17 has been sufficiently purged. For example, as shown in FIG. 46, the tubing of the fluid path set 17 may include a fiber optic cable 610 positioned adjacent thereto. The fiber-optic cable 610 may also be co-extruded with the tubing of the fluid path set 17 such that the fiber-optic cable 610 is embedded within the tubing or it may be placed inside the tubing of fluid path set 17. In another example, a reflective surface may be provided on the inside or the outside of the tubing of the fluid path set 17 to transmit light via internal reflection throughout the tube length or alternatively the fluid path material may be selected to have an index of refraction suitable for internal reflection as described herein. This will allow light to be reflected throughout the length of the tubing of the fluid path set 17 when fluid is present (similar to how a light pipe works) and result in a visible indicator that the tubing of the fluid path set 17 is purged and filled with fluid. This visual indicator can be an illuminated component at the end of the tube set which can be recognized by the sensor 114 or simply by the operator. If air is present in the fluid path set 17, for example when the tubing has not been totally primed, internal reflection of the light will not occur and the "light pipe" effect will not be observed.

Furthermore, the tubing of the fluid path set 17 can be configured to have a connector (not shown) on the end thereof that is attached to the injector 10 or positioned in a location where an electromagnetic radiation source is emitting through a section of the connector. The entire connector would only light up according to this embodiment if it is full of fluid indicating that the tubing of the fluid path set 17 is completely purged of air and is primed and ready for use. The electromagnetic radiation source may be wireless, battery powered, or connected to a power source on the injector. This means that it can have either direct or indirect contact with the tubing of the fluid path set 17 and can be either disposable or re-usable according to specific aspects.

In yet another example, the image processing software provided on the central processing unit 116 can be used to determine the volume of fluid required to purge the fluid path set 17. More specifically, the system can determine how much air is present within the syringe 12 using any of the methods described herein. Thereafter, the image processing software on the central processing unit 116 can determine the type of fluid path set 17 connected to the syringe using pattern matching techniques as described herein. Using this information, the central processing unit 116 can calculate the volume of fluid required to purge/prime the fluid path set 17. Using this information, the central processing unit 116 may instruct the injector 10 to operate the syringe to move the plunger a sufficient distance corresponding to the volume of air calculated to be in the syringe and fluid path set 17. The plunger may be moved an additional distance to eject a further volume to ensure complete priming of the system.

In another configuration of the purge container 550, one or more sensors may be associated therewith. More particularly, a component (not shown) may be provided in the purge container 550 that moves when fluid enters (meaning the tubing is being purged). The moving component may be detected by the sensor 114 or be a visual indicator for the operator and a volume of fluid coming into the purge container 550 may be determined to confirm when priming of the syringe and fluid path set 17 is complete.

For example, in one aspect, the component could be an air filter (e.g. a Porex brand filter) which allows air to pass through as the priming is taking place and then is contacted by the fluid, builds up pressure, breaks friction with the surface and is driven forward to a position that can be detected by sensor 114 or the operator. The component could also be floating balls which rise and fall relative to the presence and the density of the fluid present, discussed in detail herein with regard to positioning such balls in the syringe.

H. Capacitance Measurement Based on Swell and Stretch of at Least a Portion of the Syringe Capacitance is defined as the change in volume of a fluid path element, elements, or the whole system as a result of a change in pressure on the system, for example when the internal pressure of the system is increased by operation of the plunger to pressurize the system during an injection process. Total system expansion volume, capacity, or capacitance volume represents the total amount or volume of suppressed fluid (i.e., backflow volume) that is captured in the swelling of the injector system components due to the applied pressure. Total system capacitance and capacitance volume is inherent to each fluid injection system and depends on a plurality of factors, including injector construction, mechanical properties of materials used to construct the syringe, piston, pressure jacket surrounding the syringe, pressure jacket and restraint movement or flexing, fluid density, compressibility, and/or viscosity, change in flow volume under constant pressure, fluid lines delivering the contrast and saline to a flow mixing device, the starting pressure, the ending pressure, etc. For example, in dual syringe injectors, the amount of back or reverse flow increases when the relative speed difference between the two pistons of the injection system is large and the pressure required is high, which can occur when the simultaneous fluid flow is through a small restriction, the speed of the total fluid injection is large, and/or the viscosity of the fluid is high. The back or reverse flow can prevent different ratios of simultaneously delivered fluid from ever occurring in certain injections, which can be a detriment for all two-syringe type injector systems, such as fluid injector 10.

Capacitance measurement can be used to correct for changed flow rate and volume delivered dynamically to enhance clinical imaging practices. More specifically, in medical procedures, such as in the intravenous infusion of a contrast medium for contrast-enhanced radiographic imaging, it is often desirable to introduce a "sharp bolus" of fluid in which the medication and/or diagnostic fluid is introduced at increased pressure for rapid delivery into a specific location within the body. In the case of contrast-enhanced radiographic imaging, sufficient contrast media must be present at the specific location or region of interest in the body at a predetermined time for diagnostic quality images to be taken during the procedure. Therefore, accuracy in the amount or volume of contrast media delivered to the patient and the time at which this volume of contrast media reaches a particularly point in the body of a patient is important. A "sharp bolus" of contrast media in practice may be defined as a distinct or defined column of liquid having well-defined opposing ends or boundaries. Accordingly, accuracy in the amount of fluid delivered intravenously to a patient is often of importance in medical therapeutic and diagnostic procedures and such accuracy can be diminished by capacitance volume expansion of the fluid delivery path components when the fluid delivery system is under pressure. Further details of capacitance measurement and capacitance correction is described in U.S. Pat. No. 8,403,909 to Spohn et al., which is hereby incorporated by reference in its entirety.

Figure 47:
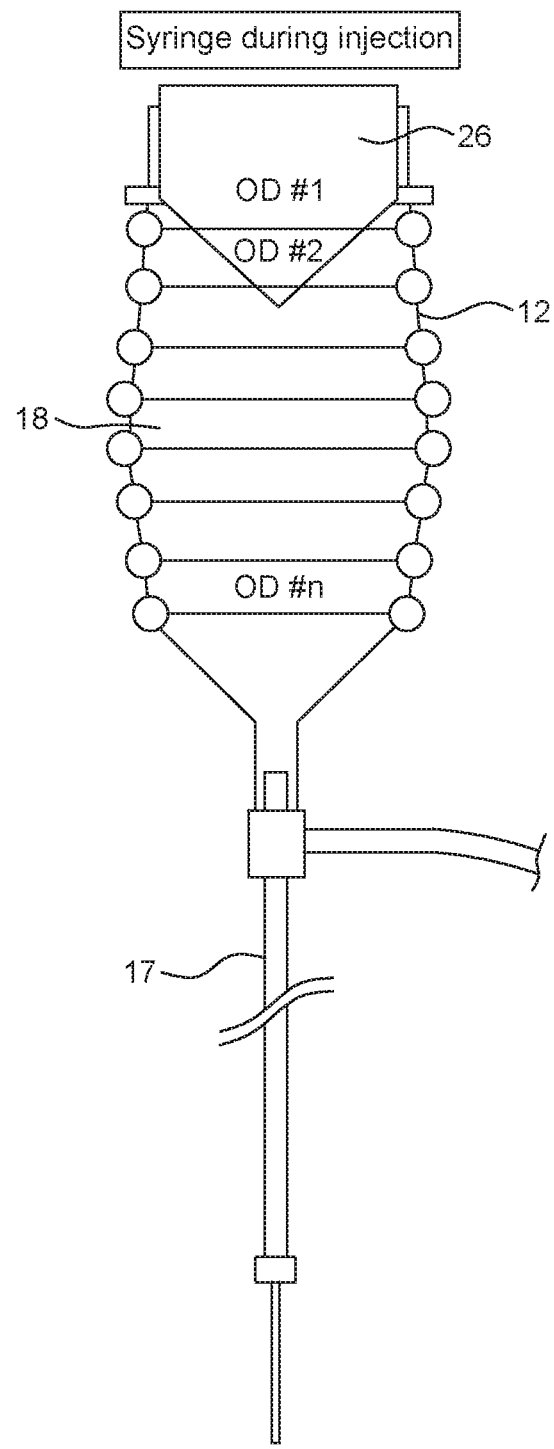
FIG. 47 is a schematic view of a syringe during an injection procedure illustrating the manner in which the syringe stretches and swells in accordance with an aspect of the present disclosure.

With reference to FIG. 47, as a fluid is delivered portions, of the syringe 12 will swell and stretch due to increase in internal pressure during an injection procedure. According to aspects of the present disclosure, the capacitance volume can then be determined as follows. This swell and stretch can be detected real-time by the at least one sensor 114 and the extent thereof can be measured using the image processing software provided on the central processing unit 116. For instance, the outside diameter of the syringe 12 along the length of the barrel 18 of the syringe 12 can be determined as shown in FIG. 47. The central processing unit 116 can then integrate across the different outer diameter measurements along the length of the barrel 18 above the bottom seal of the plunger 26 to determine an accurate volume within the syringe 12 dynamically. Thereafter, the expected volume if the syringe 12 had no capacitance is subtracted from the determined dynamic volume and this results in a remaining volume which corresponds to the capacitance volume. Once a capacitance volume is known, fluid injector 10 can be controlled to control piston 124 to compensate for expansion of barrel 18 under pressure ensuring delivery of a sharp bolus.

Figure 48:
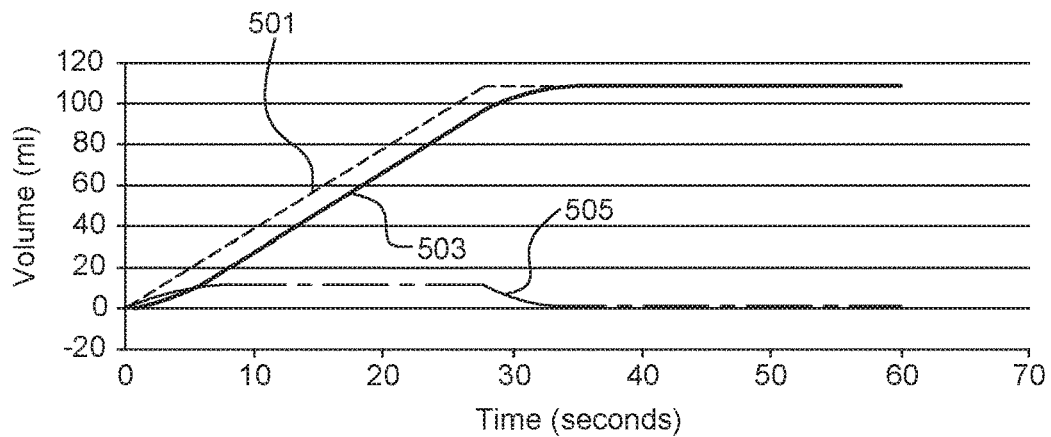
FIG. 48 is a graph illustrating volume delivered versus time during an exemplary injection procedure.

With reference to FIG. 48, a volume versus time graph of an injection procedure performed by fluid injector 10 is illustrated in which line 501 represents a volume of fluid the fluid injector 10 has been programmed to believe has been delivered absent any correction for capacitance; line 503 represents the volume of the fluid that has actually been delivered to the patient; and line 505 represents the difference due to system capacitance between what is believed to have been delivered and what has actually been delivered. The scanner (not shown) used to capture an image for diagnostic purposes is activated and instructed to start capturing images at the exact time interval the drug is expected to be passing through the particular part of the body that is desired to be imaged. That time is based on the amount of fluid the fluid injector 10 believes is being introduced over a certain period of time (i.e., line 501 in FIG. 48). Since the actual amount of fluid is delivered later than expected, the scanner may in certain instances capture images when the fluid (i.e., contrast) is not fully introduced into the part of the body being imaged. This is due to the capacitance, or swelling of the syringe and tube set with pressure as described herein. To correct for this, most operators introduce an estimated delay to try to compensate for capacitance. However, by determining the flow rate and the capacitance based on swell and stretch sections as described herein, the controller of the fluid injector 10 can automate this delay for the operator and capture the best quality images for diagnostic purposes.

I. Determination of Volume Remaining

Figure 49:
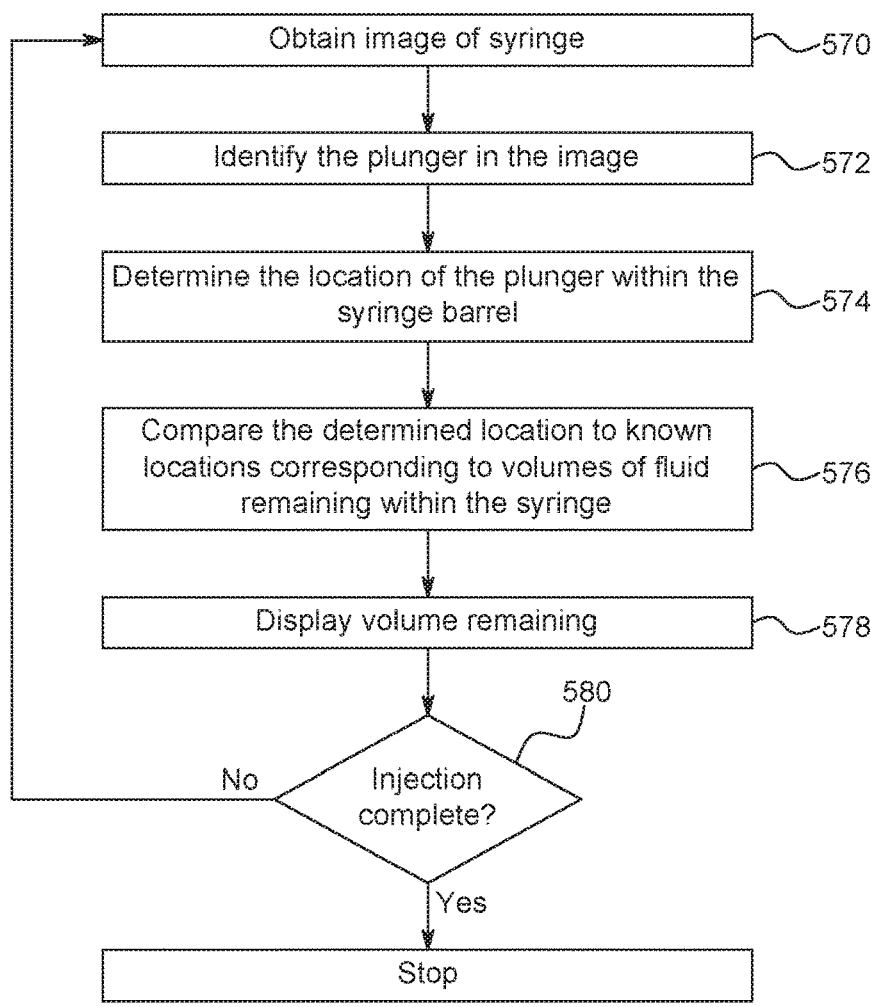
FIG. 49 is a flow chart of a method for determining the volume of fluid remaining within a syringe utilizing image processing techniques in accordance with an aspect of the present disclosure.

In one example, the fluid verification system 110 may be arranged such that the at least one sensor 114 can capture an image of the syringe 12 that includes the syringe barrel 18 and the plunger 26 such that a position of the plunger 26 in each of the images can be determined. Based on these images, the volume of contrast or saline remaining within the syringe 12 can be determined. Specifically, with reference to FIG. 49, an image of the syringe 12 is obtained by the sensor 114 at step 570. Then, at step 572, the image processing software identifies the plunger 26 in the image by using pattern recognition based on a training image as discussed herein. Next, at step 574, the image processing software determines the position of the plunger 26 within the barrel 18 of the syringe 12 by determining the change in location of the plunger 26 relative to a reference point. Once the position of the plunger 26 within the barrel 18 of the syringe 12 has been determined, this position can be compared to known positions corresponding to a volume of fluid remaining within the syringe 12 at step 576. The central processing unit 116 then sends a signal to display the volume remaining to the display 118 at step 578. The volume remaining may be displayed as a numerical value or a graphical representation of the syringe 12 may be displayed that illustrates the real-time volume remaining within the syringe. Images are continuously taken and the display of volume remaining is continuously updated until the injection procedure is complete as determined at step 580. Correction of remaining syringe volume by measurement of syringe expansion during injection due to capacitance may also be incorporated into the protocol. Accordingly, the at least one sensor may measure the change in outer diameter of the syringe, for example by comparison of an image to a reference template, and calculate the volume due to capacitance. This capacitance volume may be monitored real-time and transmitted to the central processing unit where algorithmic analysis may allow compensation for capacitance to adjust fluid delivery and provide for delivery of a sharp bolus.

In an alternative example, the volume remaining in the syringe 12 can be determined using only an image of the halo 120 if the plunger 26 of FIGS. 5A and 5B is utilized. More specifically, the plunger 26 can be formed from or coated with a reflective material having a plurality of different colored stripes 38. The reflective material forming the stripes 38 reflect light directed toward the plunger 26 in the distal direction through the syringe barrel 18 to produce the halo. As the plunger or plunger cover 26 moves through the barrel, light reflects from a different stripe 38 depending on the position of the plunger 26 within the syringe barrel 18. Since each of the stripes 38 of the plunger 26 is different in color, the color and/or appearance of the halo changes depending on the stripe 38 upon which the light is reflected as the plunger 26 advances or retracts through the syringe barrel 18 during an injection or filing procedure. The at least one sensor 114 may be positioned to capture images of the halo as the plunger advances or retracts through the syringe barrel 18. The image processing software provided on the central processing unit 116 detects the change in color of the halo. The central processing unit is configured to then determine a position of the plunger 26 within the syringe barrel 18 based on the color of the halo. Once the central processing unit 116 determines the position of the plunger 26, the volume of fluid remaining within the syringe is determined. The central processing unit 116 then sends a signal to display the volume of fluid remaining on the display 116. The volume of fluid remaining may be displayed as a numerical value or a graphical representation of syringe 12 may be displayed that illustrates the volume remaining within the syringe. In an alternative embodiment, different colored LED lights may be located in the piston to transmit light through a translucent/transparent plunger material in similar concentric circles on the plunger.

J. Pressure Feedback Based on Swell and Stretch of the Syringe

In another example, image processing techniques may be utilized to determine the pressure at which a fluid within the syringe 12 is being delivered to a patient during a fluid injection procedure due to the fact that portions, such as a portion of the distal end 24, of the syringe 12 will swell and stretch during an injection procedure. The extent of this swell and stretch may correspond to the pressure that the fluid exerts within the syringe at a given time.

Figure 50:
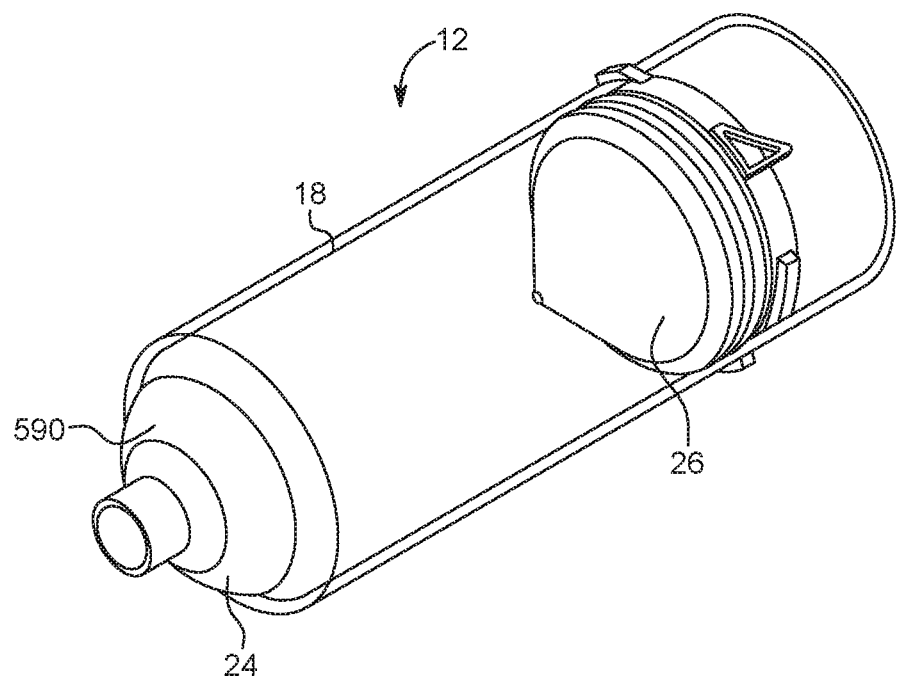
FIG. 50 is a perspective view of an alternative syringe for use with the system of FIG. 1.
Figure 51:
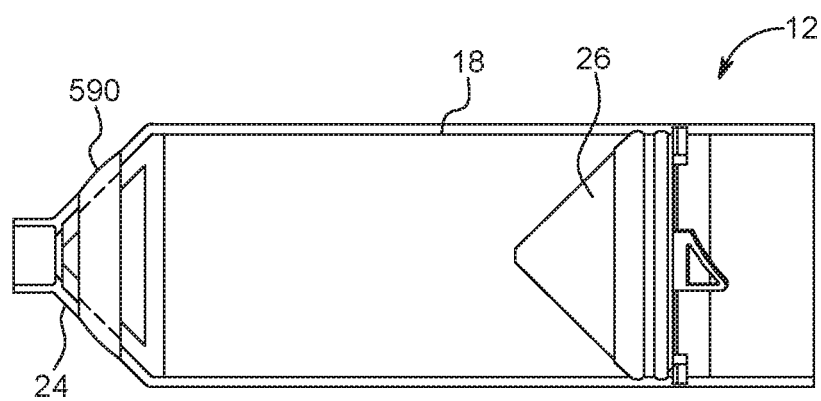
FIG. 51 is a side view of the syringe of FIG. 50.

With reference to FIGS. 50 and 51, according to one embodiment, in order to enhance this swell and stretch, an alternative example of the syringe 12 having a flexible section 590 positioned at a distal end 24 thereof may be utilized. Many components of the syringe 12 shown in FIGS. 50 and 51 are substantially similar to the components of the syringe 12 described herein with reference to FIG. 2. Reference numerals in FIGS. 50 and 51 are used to illustrate identical components as the corresponding reference numerals in FIG. 2. As the previous discussion regarding the syringe 12 generally shown in FIG. 2 is applicable to the aspect shown in FIGS. 50 and 51, only the relevant differences between these systems are discussed herein.

In one aspect, the flexible section 590 may be configured to expand when the internal pressure of the syringe 12 increases during an injection procedure. The flexible section 590 may be insert molded from a more flexible material than the syringe barrel 18. The material forming the flexible section 590 may be any suitable flexible material such as, but not limited to TPU, TPE, polypropylene, polyethylene, and, thermoplastic elastomers. In addition, flexible material 590 may be a transparent or translucent material which when illuminated with electromagnetic radiation source 112 shows a halo feature described herein.

While the flexible section 590 is illustrated in FIGS. 50 and 51 as being positioned at the distal end 24 of the syringe 12, this is not to be construed as limiting the present disclosure, as flexible section 590 may be applied to many areas of syringe 12. Factors to consider include minimizing fluid capacitance while maximizing swell for better pressure resolution.

Figure 52:
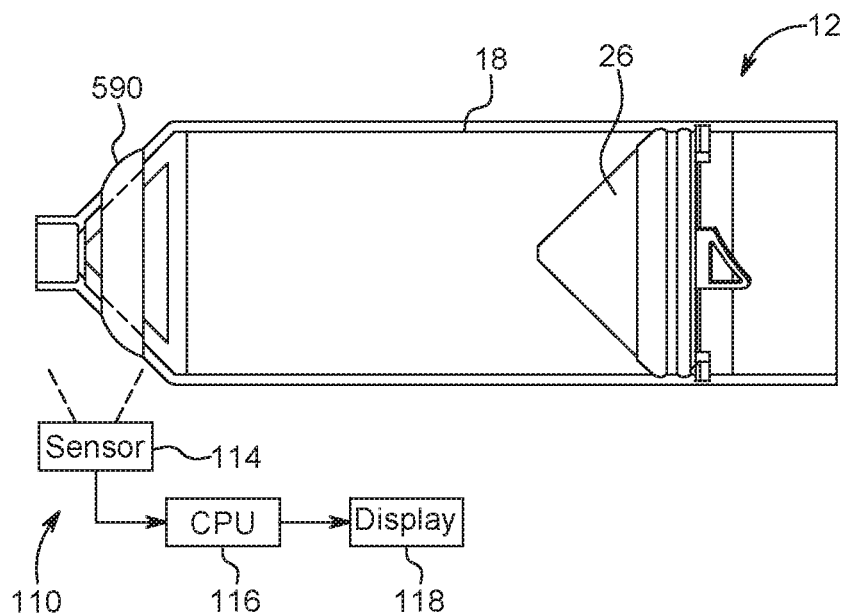
FIG. 52 is a schematic view of the syringe of FIG. 50 delivering fluid at low pressure and a fluid verification system in accordance with aspects of the present disclosure.
Figure 53:
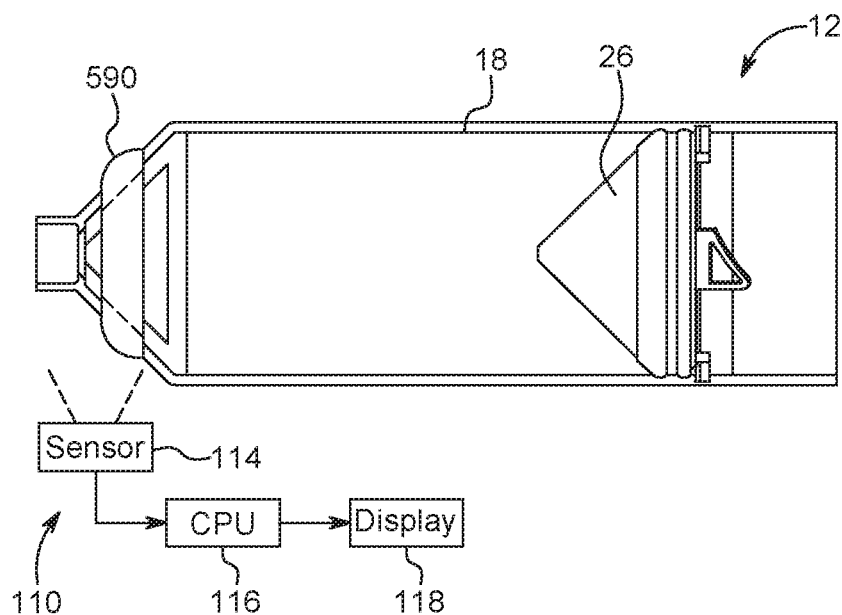
FIG. 53 is a schematic view of the syringe of FIG. 50 delivering fluid at high pressure and a fluid verification system in accordance with aspects of the present disclosure.

With reference to FIGS. 52 and 53 and continued reference to FIGS. 50 and 51, the fluid verification system 110 comprising the at least one sensor 114, central processing unit 116, and display 118 according to this aspect may be positioned such that the sensor 114 is capable of capturing an image of the flexible section 590 during an injection procedure. Once an image of the flexible section 590 is obtained, the image processing software of the central processing unit 116 measures an increased diameter of the flexible section 590 and correlates the increased diameter with syringe internal pressure. For example, FIG. 52 illustrates the flexible section 590 having a small increase in diameter that corresponds to a small syringe internal pressure while FIG. 53 illustrates the flexible section 590 having a large increase in diameter that corresponds to a large syringe internal pressure. Central processing unit 116 may display this syringe internal pressure on display 118 and control fluid injector 10 to allow active pressure control within the syringe during injections.

Figure 54:
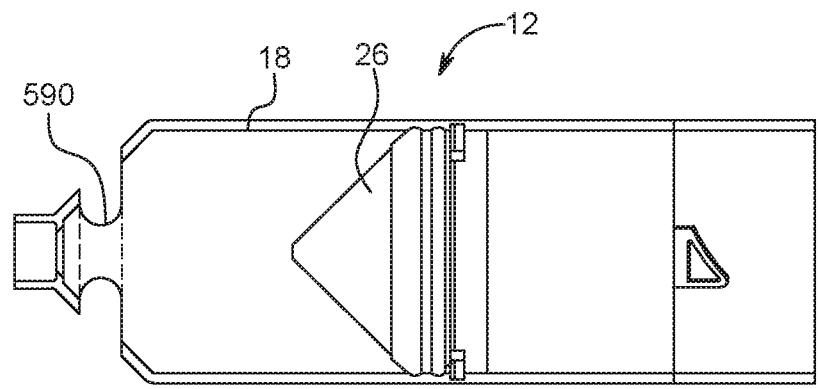
FIG. 54 is a schematic view of the syringe of FIG. 50 drawing in fluid at negative pressure in accordance with an aspect of the present disclosure.

Accordingly, the flexible section 590 provides a "live" or real-time readout on pressure within the barrel 18 of the syringe 12 during an injection procedure. With reference to FIG. 54, the negative pressure created during a filling procedure causes the flexible section 590 to move inward. The dimensional changes of the flexible section 590 can be measured using the sensor 114 and image processing software provided on the central processing unit 116 and the subsequent vacuum level can thereafter be determined.

Figure 55:
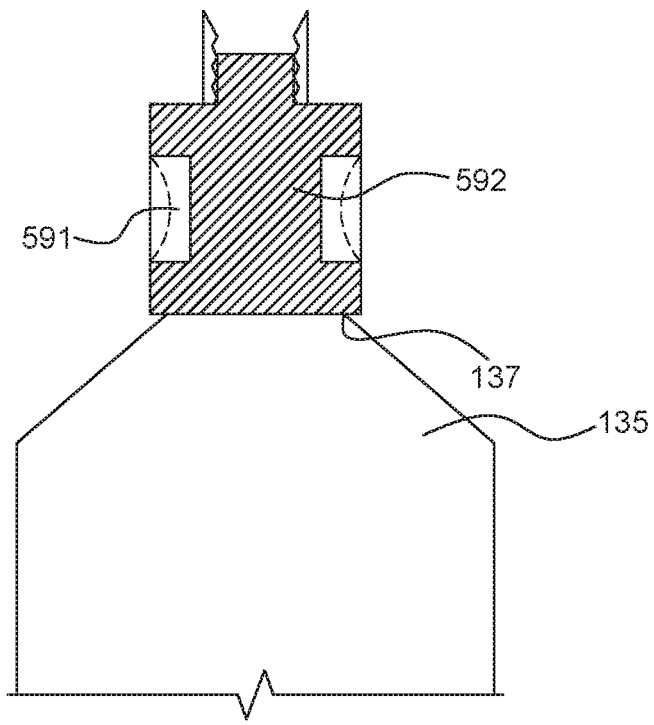
FIG. 55 is a schematic view of the syringe of FIG. 15A having a pressure indicating mechanism associated therewith in accordance with an aspect of the present disclosure.

Such negative pressure may be important to the rolling diaphragm syringe 135 described herein because having a high vacuum level during a fill of such syringe 135 could crush or deform the walls of the syringe 135. Accordingly, with reference to FIG. 55, one embodiment of the rolling diaphragm syringe 135 may be adapted to include a flexible section or diaphragm 591 on a connector 592 attached to the distal end 137 of the rolling diaphragm syringe 135 or provided in the cap 390 (not shown). The outer diameter of the flexible section 591 can be measured dynamically in real-time using the at least one sensor 114 and image processing software provided on the central processing unit 116 as described herein with regard to the measurement of the diameter of the flexible section 590. The outside diameter of the flexible section 591 decreases as the vacuum within the rolling diaphragm syringe increases during a filling procedure. Therefore, the size of the outside diameter of the flexible section 591 can be used to determine the vacuum level within the rolling diaphragm syringe 135. Thereafter, vacuum level can be maintained under a specified threshold by adjusting the rate at which piston 138 is withdrawn to prevent crushing of the rolling diaphragm syringe 135.

Figure 56A:
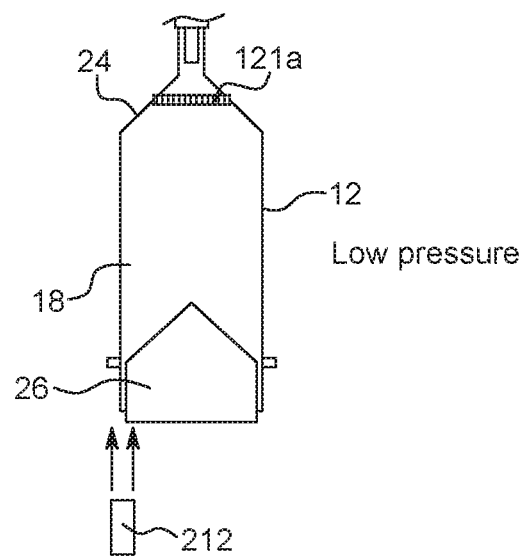
FIG. 56A is a schematic view of a syringe delivering fluid at low pressure and a fluid verification system in accordance with another aspect of the present disclosure.
Figure 56B:
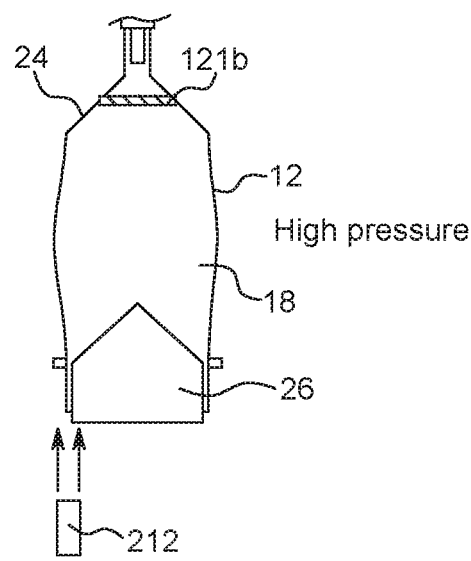
FIG. 56B is a schematic view of the syringe of FIG. 56A delivering fluid at high pressure and the fluid verification system.

With reference to FIGS. 56A and 56B, according to an aspect, a determination of the pressure within the syringe 12 can also be obtained by positioning the electromagnetic radiation source 212 such that it reflects through at least a portion of a sidewall of the syringe barrel 18. Light that shines through the sidewall of the syringe barrel 18 is visualized at the bottom of the halo 120 as shown by the lines 121a and 121b. For example, if there is no light shining up the sidewall of the syringe barrel 18, this area will appear as a black line (121b). Placing the electromagnetic radiation source 212 underneath the syringe 12 facing up towards the sidewall of the syringe barrel 18 causes the line at the bottom of the halo 120 to appear lit up (see element 121a in FIG. 56A) because the light travels up the interior of the sidewall of the syringe barrel 18 and is portrayed in the halo 120.

As the syringe 12 is subjected to pressure for example during an injection procedure, it swells, pushing the walls of the syringe 12 outward as shown in FIG. 56B. This removes the straight-line path for the light from the electromagnetic radiation source 212 to the bottom of the halo 120. This line fades from light to dark as the syringe 12 swells (i.e., pressure increased) (see element 121b in FIG. 56B). The electromagnetic radiation source 212 may also be placed such that the light would completely disappear when the pressure limit of the syringe was reached (i.e., the syringe swells enough to block the light). Alternatively the brightness could be determined as a function of pressure (i.e., swelling) and be used to determine pressure. For example, image recognition software may be used to monitor change in intensity of the line to provide real-time feedback on syringe capacitance.

K. Flow Rate Feedback

Feedback regarding the flow rate of the fluid delivered by the fluid injector could also be provided to an operator using many of the concepts described herein. More specifically, the position of the plunger 26 axially within the syringe barrel 18 can be monitored by the sensor 114 and the image processing software during an injection procedure. Thereafter, a curve can be created showing the position of the plunger relative to the time during the injection procedure. An equation to fit the curve can then be derived. The equation is then provided to a logic algorithm in which the data from the curve is embodied to calculate the flow rate of fluid being delivered by the injector. This flow rate can be displayed to the operator on display 118.

L. Syringe Filling Feedback

When filling the syringe 12, with contrast or saline, it has been observed that the halo or illuminated identification pattern 120 described in detail herein is only present if the syringe is being filled at a proper rate. For example, using a syringe such as the syringe 12, the proper fill rate is about 4 mL/sec because this is the fastest fill rate with the thickest fluid that can be achieved before a vacuum head is drawn into the syringe. However, the fastest specified fill rate will depend upon the particular restrictions of the fluid injection system at issue. The piston should be drawn back such that the syringe is filled in the fastest possible manner depending on the fluid injection system that is being utilized. This is accomplished using the concepts described herein by dynamically examining the halo 120 using the sensor 114 and the image processing software provided on the central processing unit 116 during a filling procedure. As long as the halo 120 is determined to be completely present then the vacuum has not reached a threshold where a vacuum head (i.e., air) is generated in the syringe. The halo 120 is recognized using the sensor 114 and the image processing software provided on the central processing unit 116 as described herein and the position of the top edge of the halo 120 relative to the bottom edge of the halo 120 is detected. If the top edge of the halo 120 begins to move downward, an indication that air is being pulled into the syringe 12 can be provided to the operator. In addition, the fluid injector 10 can be controlled to adjust the rate at which the piston 124 is drawing the plunger 26 back to reestablish the appropriate size of the halo 120. This allows the fluid injector 10 to achieve the fastest possible fill rate independent of the size of the syringe, the fluid type, or the fill rate.

In other words, if the syringe is being filled too fast, which leads to air being introduced into the syringe, the halo 120 will not be present. Accordingly, the sensor 114 can be positioned to capture an image of the halo 120 during a filling procedure. The image processing software of the central processing unit 116 processes the image to determine the presence of the halo 120. If an absence of the halo 120 results, a signal is sent to the fluid injector 10 to stop the filling process and adjust the rate at which the piston rod 124 retracts the plunger 26 so that the halo 120 is present throughout the filling process.

M. Other Features of the Syringe that May be Identified with Image Processing

Several other features of the syringe 12 may be imaged using the fluid verification system 110 and information obtained thereby may be provided to the fluid injector 10. For example, it is often necessary for the operator or technician to validate the syringe prior to performing the injection. Validation may include confirming that the syringe is acceptable for the injector and determining various characteristics of the syringe and fluid contained therein. For example, the operator must verify that identifying information, such as the syringe dimensions (e.g., diameter, length, and fluid volume), and fluid contents are correct for the procedure being performed. In addition, the operator may be required to provide certain information about the syringe, such as the date of manufacture, source, frictional characteristics between the plunger and syringe barrel, fluid viscosity, and the like (referred to generally herein as "syringe injection parameters") to the fluid injector or the injector operating system to control piston force and acceleration to deliver fluid at a desired flow rate. The identifying information may be contained on or associated with a machine readable identification tag, such as a barcode. Accordingly, an image of such a barcode may be obtained by the sensor 114. The image processing software provided on the central processing unit 116 may then be configured to read the identifying information from the barcode and provide this information to the fluid injector 10. In certain examples, the barcode may be backlit by the electromagnetic radiation source 112, thereby making it more clearly visible to the sensor 114.

In addition, the cylindrical syringe barrel 18 is, in effect, a lens itself. Utilizing the curvature of the barrel wall, images that are captured and recognized appear different to the image processing software provided on the central processing unit 116 if there is air in the syringe 12 or if fluid is present in the syringe 12. If there is air in the syringe 12, the image of the barcode received by the sensor 114 appears in a first size and/or orientation. If there is fluid present in the syringe 114, the image of the barcode appears in a second size and is inverted. Accordingly, in one example, the barcode may be encoded with information such that when it is read by the sensor 114 when there is air in the syringe 12, the code informs the system that the syringe 12 is present, the size of the syringe 12, and that air is present in the syringe 12. When fluid is present within the syringe 12, the barcode image inverts and the image processing software provided on the central processing unit 116 recognizes the new code which provides a signal to the system indicating that fluid is present within the syringe 12. Furthermore, the relative size of the barcode provides an indication of the fluid type within the syringe 12 (i.e., saline, contrast, or the type of contrast).

Figure 57:
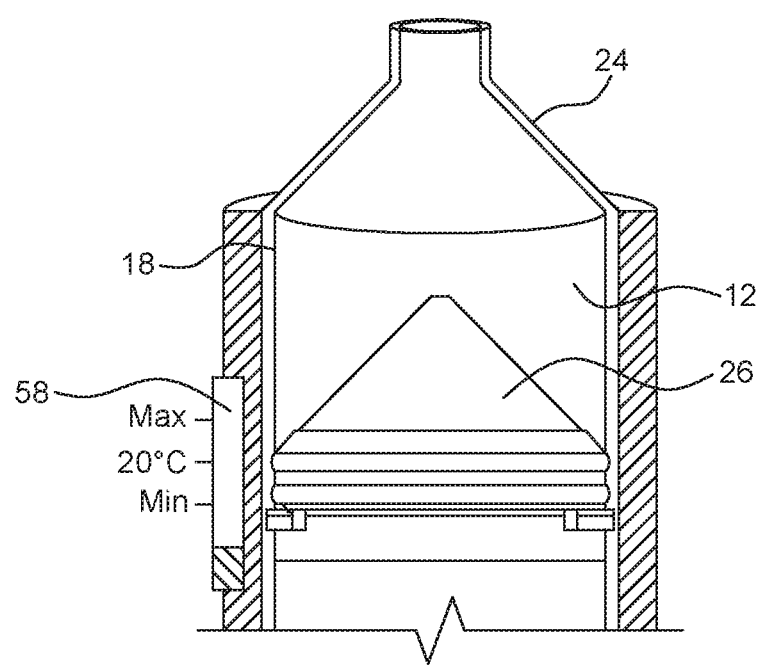
FIG. 57 is a schematic view of a syringe having a temperature strip incorporated therewith in accordance with an aspect of the present disclosure.

In another example, with reference to FIG. 57, a temperature strip 58 may be added to the syringe 12 to provide an indication of the temperature of the contents of the syringe 12 to an operator. This temperature strip 58 may be imaged by the sensor 114 and automatically read by the image processing software. Specifically, the sensor 114 is positioned to capture an image of the temperature strip 58 on the syringe barrel 18. The temperature strip 58 is configured to change color with temperature or have some other method that indicates the temperature. The image processing software is configured to detect this change in color and determine the temperature based on the change in color. Thereafter, the temperature information may be provided to the fluid injector. In certain examples, temperature strip and barcode may both be provided on a label applied to the syringe 12.

N. Exemplary Fluid Injection System Utilizing Image Recognition Techniques

Figure 59:
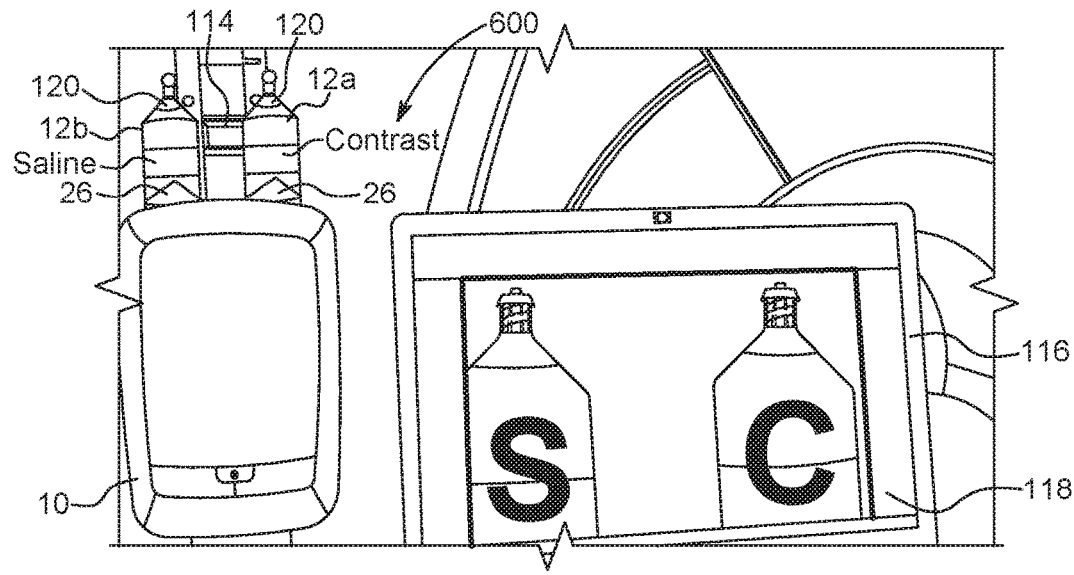
FIG. 59 is a schematic view of the fluid injection system in accordance with an aspect of the present disclosure.
Figure 60:
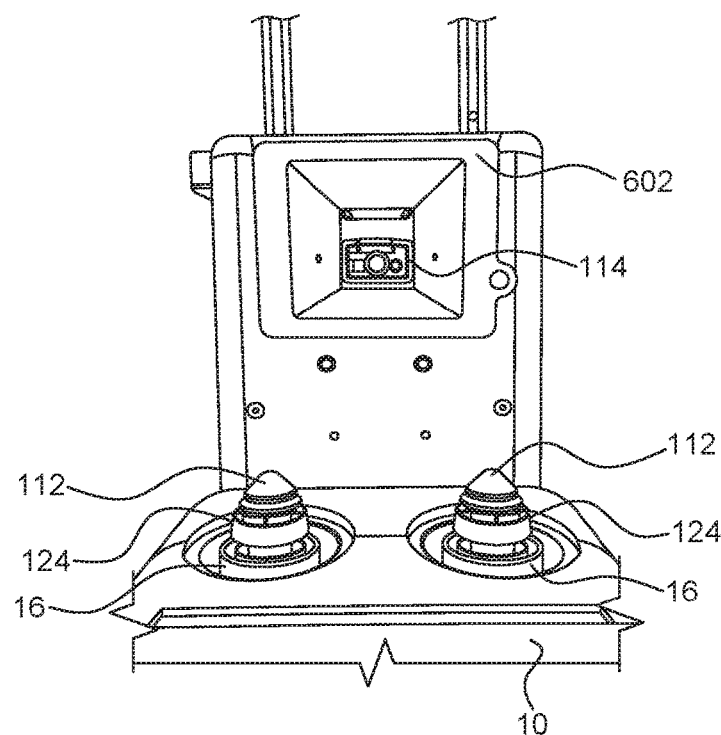
FIG. 60 is a schematic view of a portion of the fluid injector of the fluid injection system of FIG. 59.

With reference to FIGS. 58-60, an exemplary fluid injection system 600 comprises a fluid injector 10 that may have a housing 14 formed from a suitable structural material, such as plastic, a composite material, and/or metal. The housing 14 may be of various shapes and sizes depending on the desired application. For example, the fluid injection system 600 may be a freestanding structure having a support portion 70 connected to a base 72 with one or more rollers or wheels such that the fluid injector 10 is movable over the floor. The fluid injector 10 may include at least one syringe port 16 for releasably connecting the at least one syringe 12 to respective piston rods 124. In various examples, the at least one syringe includes at least one syringe retaining member configured for retaining the syringe within the syringe port 16 of the fluid injector 10. In non-limiting examples, the at least one syringe retaining member is configured to operatively engage a locking mechanism provided on or in the syringe port 16 of the fluid injector 10 to facilitate self-oriented loading and/or removal of the syringe to and from the injector 10. The syringe retaining member and the locking mechanism together define a connection interface for connecting the syringe to the fluid injector 10. An example of various connection interfaces is described in U.S. Pat. No. 9,173,995.

In certain non-limiting examples, it is desirable to temporarily rotate and/or invert the injector housing 14 including syringe ports between a substantially vertical position (i.e., with the syringe port(s) pointing upwards), which may facilitate, for example, the loading of a syringe into a syringe port or the filling of a syringe with medical fluid, and an inverted position, which may facilitate, for example, the removal of air bubbles in a medical fluid contained within a syringe, or the conducting of an injection procedure. Accordingly, in non-limiting examples, housing 14 may be connected to support portion 70 in a rotatable fashion such that housing 14 is rotatable relative to the support portion 70 and retractable pole 74.

The fluid injection system 600 may further include a lower support member 76 that may be extended or retracted in a vertical direction to adjust the height of the fluid injector 10. An operator may push down on a handle 78 to release a locking connection between the lower support member 76 and a fluid warmer 80 provided on the lower support member 76. As the handle 78 is pressed down, the operator can lift or lower the fluid warmer 80 to adjust the height of the fluid injector 10.

In non-limiting examples, at least one fluid path set 17 may be fluidly connected with the distal end of the at least one syringe for delivering medical fluid from the at least one syringe to a catheter, needle, or other fluid delivery connection (not shown) inserted into a patient at a vascular access site. Fluid flow from the at least one syringe may be regulated by a fluid control module operated by a controller, such as a detachable touch screen controller 82 or any suitable device. The fluid control module may operate various pistons, valves, and/or flow regulating devices to regulate the delivery of the medical fluid, such as saline and contrast, to the patient based on one or more user selected injection parameters, such as injection flow rate, duration, total injection volume, and/or ratio of contrast media and saline.

The controller 82 may include one or more processors, memory, network interfaces, and/or the like and may be configured to control a display comprising a graphical user interface ("GUI"), which may allow a user to view and/or interact with various injection parameters through graphical icons and visual indicators produced on the display. The controller 82 may include the central processing unit 116 having the image processing software provided thereon or on a separate unit. In non-limiting examples, the controller 82 may be formed as a detachable touch screen controller. The controller 82 may also be non-removably attached to the fluid injector 10. The controller 82 may be used to monitor one or more injection parameters, including, for example, patient specific information (age, weight, sex, organ to be imaged, dosage of imaging agent, etc.), which may be inputted by the user or recalled/downloaded from a database, a network, a memory, or another controller in communication with the system by a wired or wireless communication process. The controller 82 may be further configured to control various injection parameters which may be inputted by a user and/or calculated by one or more algorithmic calculations performed by the controller 82, the fluid control device, and/or another controller or processor in communication with the fluid control device and/or the controller 82 based on data downloaded from a database and/or inputted by a user.

With specific reference to FIGS. 59 and 60, the exemplary fluid injection system 600 utilizes the illuminated identification pattern and image processing techniques discussed herein. As described above, the system 600 includes a fluid injector 10 similar to the fluid injector described with reference to FIG. 1. The fluid injector 10 is configured to engage a pair of syringes 12. The syringes 12 are mounted to syringe ports 16 of the fluid injector 10. A number of electromagnetic radiation sources 112, such as LEDs, are mounted to or embedded in a distal end of a piston rod 124 of the injector 10. The LEDs are configured to illuminate in a first color when a first fluid is detected within the syringe 12 and a second color when a second fluid is detected within the syringe 12. When actuated, the piston rod 124 advances toward and is received within the cavity (not shown) defined by the plunger 26. The LEDs emit light in the axial direction through the plunger cover 26 for producing the halo 120 adjacent to the distal end 24 of the syringe barrel 18 in the manner discussed above. The sensor 114 may be removably provided on a support portion 602 of the fluid injection system 600 such that the sensor 114 is positioned behind the syringes 12 when the syringes 12 are being filled with fluid from a multi-dose fluid bottle or bag. As described herein, the fluid injection system 600 may be configured to identify the type of fluid that is directed into the syringe 12 or the fluid level in each syringe 12 using image processing techniques. Based on the information identified by the imagining processing techniques, the injector 10 may adjust its operating parameters to achieve desired filling and injection parameters.

As discussed herein, the electromagnetic radiation source 112 may be a light bulb, LED bulb, visible light emitter, infrared emitter, or laser, positioned to project an electromagnetic radiation beam through an interior of the syringe 12. The electromagnetic radiation source emits electromagnetic radiation generally in an axial direction through the syringe 12. For example, an electromagnetic radiation beam may pass through a translucent or transparent plunger or plunger cover 26 and toward the distal end 24 of the syringe 12.

As discussed in greater detail herein, the electromagnetic radiation source 112 can be configured to increase conspicuousness of the halo 120 or to tailor the halo 120 for particular sensors or electromagnetic radiation detectors. In one example, the electromagnetic radiation source 112 includes a laser having a wavelength of about 532 nm (e.g., a green laser). The green laser electromagnetic radiation source can be used with neutral colored or transparent plungers and still produce a conspicuous colored halo. In other examples, the electromagnetic radiation source 112 can emit electromagnetic radiation outside the visible spectrum provided that the system includes a sensor or camera capable of detecting radiation (e.g., the halo) within the emitted wavelength. In one such aspect, an infrared sensor may be provided to detect the radiation on the syringe 12. In still other examples, the electromagnetic radiation source can be configured to emit polarized light or certain wavelengths of filtered light, which can be more easily distinguished from ambient light. In other examples, the electromagnetic radiation source can be configured to emit pulses of light according to a predetermined and identifiable sequence, which can be identified by a system operator or automatically detected by a sensor.

Light or electromagnetic radiation passing through the plunger or plunger cover 26 substantially radiates through the syringe 12 to form the halo 120. When the syringe 12 is empty or only partially filled, the electromagnetic radiation beams pass through the syringe 12, but do not form a distinctive illuminated portion or halo near the distal end thereof as shown in FIG. 8. In contrast, when the syringe 12 is entirely filled with fluid, the electromagnetic radiation beams are refracted by the fluid, which produces a halo 120 near the distal end 24 of the syringe 12. A system operator or automated image reading or optical device, such as sensor 114, can identify whether the halo, if present, is the correct shape and size. If the halo is too small, not bright enough, or not present at all, the system operator can add additional fluid to the syringe 12 for complete filling. If a halo having the correct size, shape, and brightness is identified, then verification is complete and the fluid contents of the syringe 12 are ready for administration to a patient.

In certain examples, the system 600 is also capable of, through the use of image recognition, determining whether two syringes 12 are present on the fluid injector 10 simultaneously. In addition, the system 600 detects whether the syringes 12 are filled with fluid or air. The system 600 also, using images obtained from sensor 114, visualizes features on the syringe barrel 18, visualizes height differences of the halo 120, or visualizes laser light passing through the fluid to detect which of the two syringes 12 has contrast and which has saline as described in greater detail herein. Once this has been determined, the system 600 can send a signal to the electromagnetic radiation source 112 positioned on the piston rod 124 underneath the translucent plungers on the injector head. This signal can alert the electromagnetic radiation source to light up the LEDs in a first color, such as green, underneath syringe 12 determined to have contrast, and light up the LEDs in a second color, such as blue, underneath syringe 12 determined to have saline. This light will illuminate halo 120 to have a color corresponding to that of the LEDs, for visualization by the operator.

The system can also send a signal to alert the operator of the type of fluid via any other method of visual, auditory, or sensory cues. For instance, once it has been determined by image recognition techniques that a syringe 12 contains contrast, visual cues (LEDs, laser light, graphics, and/or text) and/or auditory cues (alarms, bells, whistles, other sounds) alerts the operator to the fact that a particular syringe 12 contains contrast. For example, green overlay features may be used for the side of the injector 10 specified for contrast. Green LEDs can be used to illuminate the halo 120 on the syringe 12 that has been determined to have contrast, regardless of which side the syringe 12 is on. This will be achieved by having circuits of both LED colors (green and blue) where the green will be illuminated if contrast is determined to be present and blue if saline is determined to be present. It is also possible to send messages to the operator in the control room alerting them to which syringe is on which side, and whether that conflicts with the protocol prescribed by the attending physician.

Figure 61:
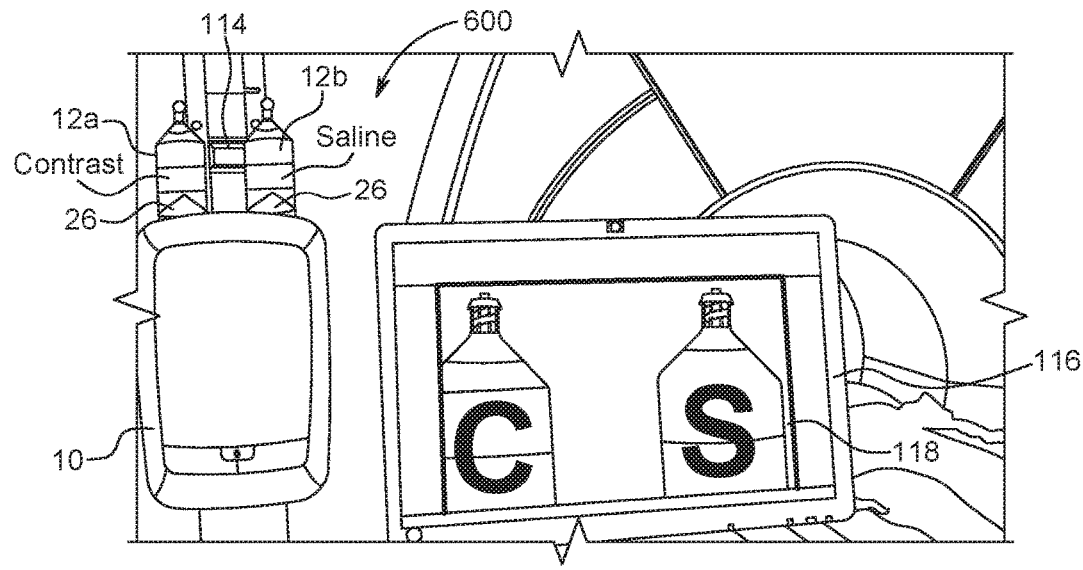
FIGS. 61-63 are schematic views of various configurations of the fluid injection system of FIG. 59.
Figure 62:
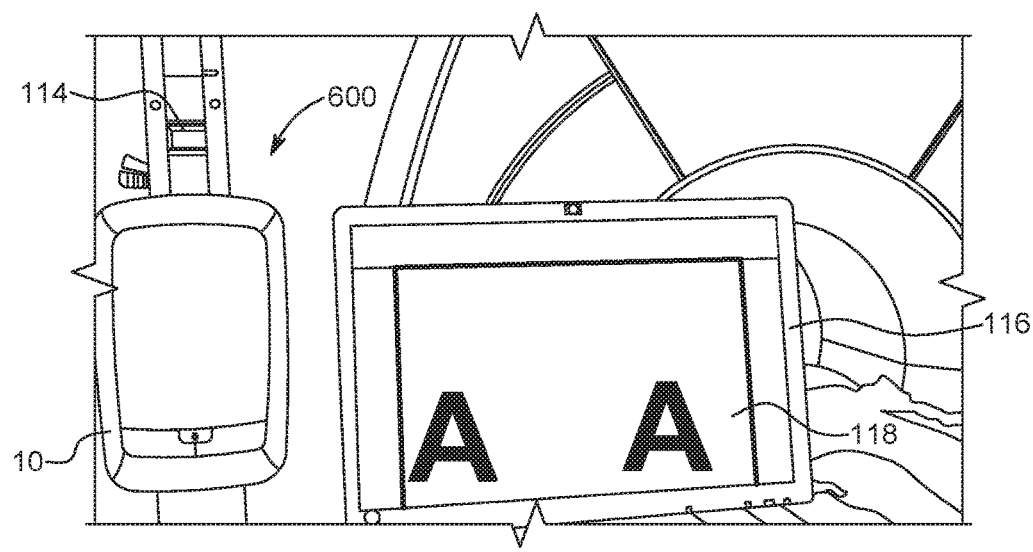
Figure 63:
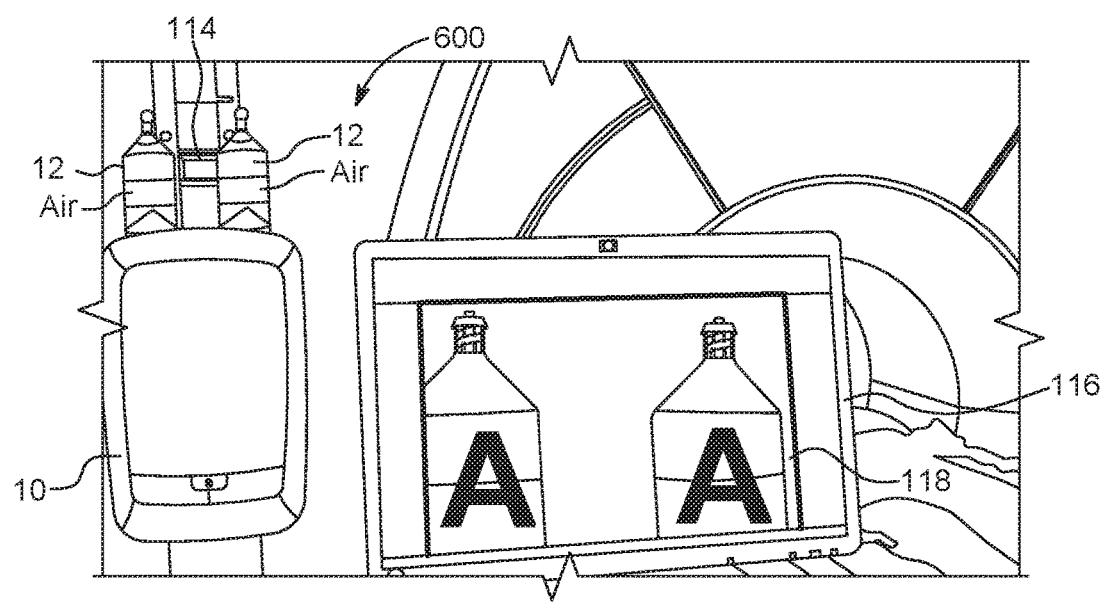

With specific reference to FIG. 59, the system 600 has determined that a contrast syringe 12a is installed at right and a saline syringe 12b at left as shown. On the display 118, "C" is displayed at right and "S" at left to indicate that the image processing software of the central processing unit 116 has identified contents of syringe at left as saline and contents of syringe at right as contrast. With reference to FIG. 61, the contrast syringe 12a has been moved to the left position and saline syringe 12b to the right position as shown. On the display 118, "C" is now displayed at the left and "S" is now displayed at the right to indicate that the image processing software of the central processing unit 116 has identified contents of syringe at left as contrast and contents of syringe at right as saline. With reference to FIG. 62, the fluid injector 10 is shown with the syringes 12a, 12b absent. On the display 118, "A" is now displayed at both left and right to indicate that the image processing software of the central processing unit 116 has identified air present at both locations. With reference to FIG. 63, an empty syringe 12 has been installed at the left position and another empty syringe 12 has been installed at right position as shown. On the display 118, "A" is now displayed at both left and right to indicate that the image processing software of the central processing unit 116 has identified air present in both syringes.

O. Utilizing a Syringe with Floating Elements

Figure 64:
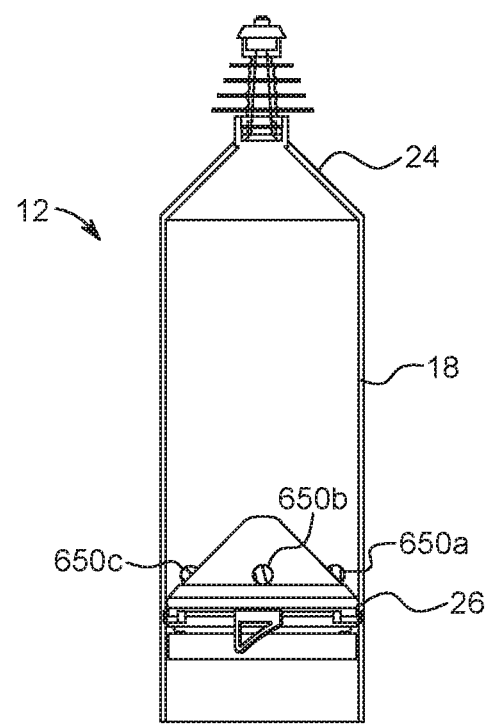
FIG. 64 is a schematic view of another alternative syringe for use with the system of FIG. 1.

With reference to FIG. 64, another alternative example of a syringe 12 that may be used with fluid injector 10 and fluid verification system 110 to determine the type of fluid within the syringe 12 is illustrated. This syringe 12 is similar to the syringe 12 of FIG. 2 except that it includes a plurality of objects, such as floating balls 650a, 650b, and 650c, positioned between the distal end 24 of the syringe 12 and the plunger. The density of the balls 650a, 650b, and 650c are different to allow the ball 650b to float in saline (density equal to or less than 1.0 g/ml) and the ball 650c to sink in saline but float in contrast (density greater than 1.1 g/ml but less than least dense contrast).

The floating balls 650a, 650b, and 650c for contrast and saline differentiation operate based on the principle of buoyancy. This is an upward force on an object in fluid opposing its weight downward. The driving variable of this phenomenon is density, specifically of the fluid and of the weight immersed in the fluid. If the density of the balls 650a, 650b, and 650c is greater than that of the fluid by enough margin, the weight overcomes the buoyant force and the balls 650a, 650b, 650c sink to the bottom. If the density of the balls 650a, 650b, 650c is less by enough margin, the ball 650a, 650b, 650c float.

Figure 65:
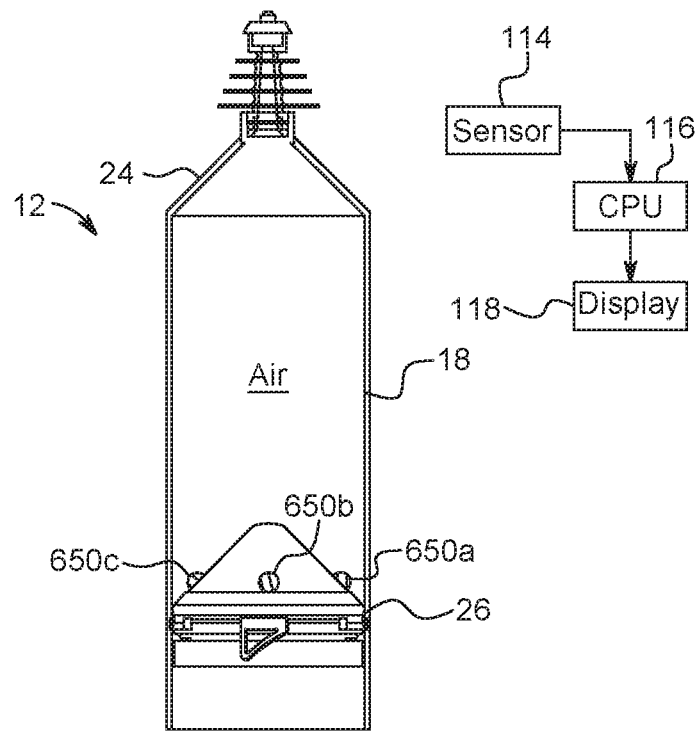
FIG. 65 is a schematic view of the syringe of FIG. 64 filled with air and a fluid verification system in accordance with an aspect of the present disclosure.
Figure 66:
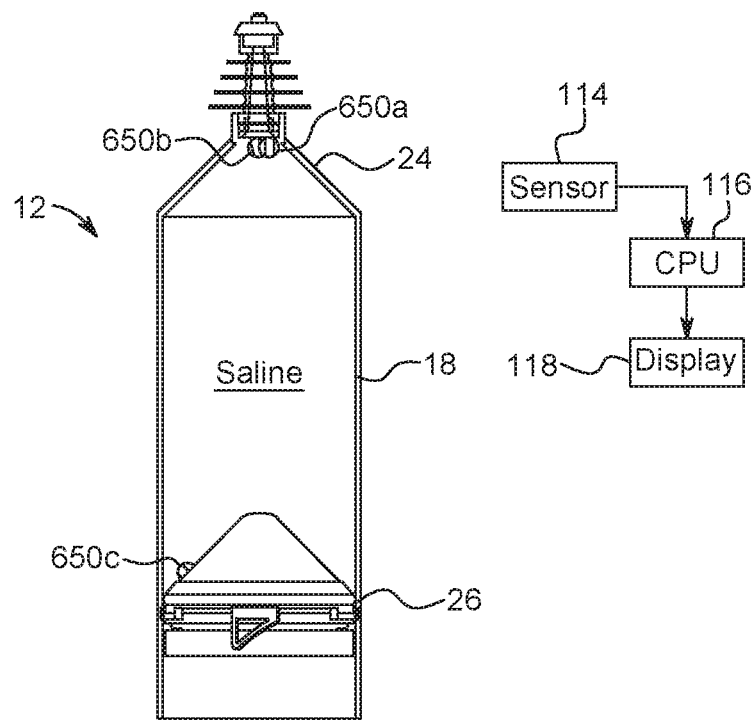
FIG. 66 is a schematic view of the syringe of FIG. 64 filled with saline and a fluid verification system in accordance with an aspect of the present disclosure.
Figure 67:
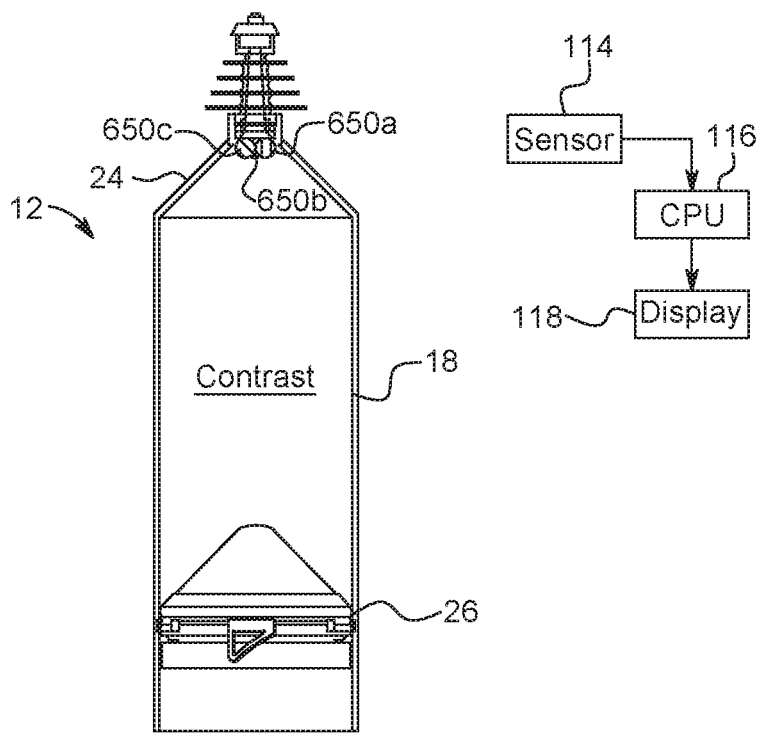
FIG. 67 is a schematic view of the syringe of FIG. 64 filled with contrast and a fluid verification system in accordance with an aspect of the present disclosure.

Saline and contrast have different densities. For example, saline may have a density around 1 g/mL, while the thicker contrasts have densities around 17 g/mL). In one example, ball 650b has a density of 0.5 g/mL and ball 650c has a density of 5 g/mL. With reference to FIG. 65, when the syringe 12 is full of air and positioned upright all of the floating balls 650a, 650b, and 650c sit at the bottom of the syringe 12 due to gravity. Accordingly, a syringe 12 filled with air has no balls floating near the distal end 24 thereof. With reference to FIG. 66, when the syringe 12 is filled with saline, based on the principle described above, the ball of density 0.5 g/mL (i.e., ball 650b) floats to the distal end 24 of the syringe 12, while the ball of density 5 g/mL (ball 650c) remains at the bottom as the buoyant force does not overcome its weight. A reference ball 650a may also be positioned within the syringe 12 having a density of less than 0.5 g/mL. This ball 650a also floats to the distal end 24 of the syringe 12 when saline is present within the syringe 12. Accordingly, a syringe 12 filled with saline has two balls floating near the distal end 24 thereof. With reference to FIG. 67, when syringe 12 is filled with contrast of density 17 g/mL, all three balls 650a, 650b, 650c float to the top as each ball has a density less than the fluid in which they are immersed.

With continued reference to FIGS. 65-67, the sensor 114 may be positioned to capture an image of the distal end 24 of the syringe 12. Thereafter, the image processing software on the central processing unit 116 can detect the presence or absence of the balls 650a, 650b, and 650c in the image. If the image processing software on the central processing unit 116 determines that no balls are present, a signal can be sent to the display 118 to display that air is present within the syringe 12. If the image processing software on the central processing unit 116 determines that balls 650a and 650b are present, a signal can be sent to the display 118 to display that saline is present within the syringe 12. Finally, if the image processing software on the central processing unit 116 determines that all three balls are present, a signal can be sent to the display 118 to display that contrast is present within the syringe. This principle works for any number of balls in the syringe as long as they have the proper corresponding densities. A more in-depth application is having several different balls of varying densities that correspond to the varying densities of different brands and concentrations of contrast. This principle can then be used to determine the different types of contrast present using image recognition of floating balls. In addition, the balls 650a, 650b, and 650c may have different sizes to provide another characteristic to allow the image processing software to differentiate between contrast and saline.

The syringe 12 of FIG. 64 may also be utilized to determine a temperature of a fluid contained within the syringe 12. The floating balls 650a, 650b, and 650c for temperature determination again operate based on the principle of buoyancy. This is an upward force on an object in fluid opposing its weight downward. The driving variable of this phenomenon is density, specifically of the fluid and of the weight immersed in the fluid. If the density of the balls 650a, 650b, and 650c is greater than that of the fluid by enough margin, the weight overcomes the buoyant force and the balls 650a, 650b, and 650c sink to the bottom. If the density of the balls 650a, 650b, and 650c is less by enough margin, the balls float. In this application, density changes with temperature. As a fluid contained within the syringe 12 is heated, its volume tends to increase which decreases its density. Accordingly, the floating balls 650a, 650b, and 650c may have incremental densities (e.g., 0.5 g/mL, 0.6 g/mL, 0.7 g/mL for saline and 15 g/mL, 15.5 g/mL, 16 g/mL for contrast) so that as the temperature of the fluid is increased, the corresponding decrease in density will cause specific balls 650*a*, 650*b*, and 650*c* to either float or sink. The distal end 24 of the syringe 12 may be imaged using the sensor 114 and the image processing software on the central processing unit 116 can determine the number of balls present in the image. Once the number of balls is determined, the central processing unit 116 can correlate the number of balls to the temperature of the fluid. The diameter of the balls 650*a*, 650*b*, and 650*c* may also be varied to correspond with their density/temperature relationship so that the image processing software on the central processing unit 116 can measure the diameter and correlate that to a density and from the density to a temperature of the fluid.

The syringe 12 of FIG. 64 may also be utilized as a pressure limiting tool. More specifically, one of the balls 650*a*, 650*b*, and 650*c* may be configured to have a lightly positive buoyancy at zero pressure when submerged in a fluid. Accordingly, such a ball floats when the syringe is not injecting fluid and is filled with fluid. As the injection begins, the pressure inside the syringe increases. Since the air in the floating ball is more compressible than the fluid contained within the syringe, the volume of the ball decreases, thereby increasing its density. Therefore, the floating balls can be designed to sink at a particular internal pressure within the syringe. For example, the ball could be designed to drop to the bottom of the syringe at pressures greater than 325 psi. The dropping ball is then captured in images taken by the sensor 114 and detected by the image processing software. A signal is then sent to the fluid injector to limit the pressure of the injection.

III. Other Concepts

In another example, the source 112 can emit light of a given wavelength and the speed at which the light travels through the syringe can be measured by a detector and processor and is indicative of the type of fluid contained within the syringe 12.

It should be noted that while all of the concepts described herein are described with reference to syringes and fluid injectors, this is not to be construed as limiting the present invention as these concepts may be utilized with any fluid container. For example, these concepts may be utilized in a beverage bottling setting to ensure that each bottle that is manufactured includes the correct volume of liquid and the correct liquid. The bottles may be provided with a colored translucent or transparent bottom and an angled neck. After the bottles are filled, an electromagnetic radiation source is positioned beneath the bottles to provide light through the bottles and generate a halo near the neck of the bottles. This halo can be identified using a sensor and image processing software as described herein. If the halo is absent or an improper size, a signal is generated that the bottle was not properly filled.

Although the disclosure has been described in detail for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements. For example, it is to be understood that the present disclosure contemplates that, to the extent possible, one or more features of any embodiment can be combined with one or more features of any other embodiment.

We claim:

1. A syringe configured for use with a powered injector, the syringe comprising:
   a barrel comprising a distal end having a tapered, conical surface, wherein the barrel defines an interior volume configured to receive a fluid, and a proximal end configured to be releasably connected to the powered injector; and
   a plunger slideably disposed in the barrel to advance through the barrel to expel the fluid therefrom, the plunger comprising a substantially conical shape having an exterior distal surface, wherein at least a portion of the distal surface is tinted a conspicuous color to reflect at least a portion of incident electromagnetic radiation off a surface of the barrel toward the distal end of the barrel such that a reflected identification brightness pattern of the same conspicuous color is formed at a predetermined portion of the tapered, conical surface of the distal end of the barrel when the syringe is filled with the fluid.

2. The syringe of claim 1, wherein the reflected identification brightness pattern is indicative of at least one property of at least one of the syringe and the fluid.

3. The syringe of claim 2, wherein the reflected identification brightness pattern is not formed at the predetermined portion of the tapered, conical surface of the distal end of the barrel when the syringe is completely or partially filled with air.

4. The syringe of claim 2, wherein the at least one property of at least one of the syringe and the fluid comprises an identity of the fluid in the syringe.

5. The syringe of claim 1, wherein the plunger comprises a plunger cover on the distal surface, wherein at least a portion of the plunger cover is tinted the conspicuous color.

6. The method of claim 1, wherein the reflected identification brightness pattern of the same conspicuous color comprises a halo of the conspicuous color formed at the predetermined portion of the tapered, conical surface of the distal end of the barrel.

7. The syringe of claim 1, wherein the conspicuous color is selected from the group consisting of red, green, orange, and yellow.

8. The syringe of claim 1, wherein the reflected identification brightness pattern of the same conspicuous color is noticeable by visual inspection when the syringe is filled with the fluid.

9. The syringe of claim 1, wherein the tapered, conical surface of the distal end has a taper angle of from about 30 degrees to about 60 degrees.

10. The syringe of claim 9, wherein the tapered, conical surface of the distal end has a taper angle of about 45 degrees.

11. A syringe configured for use with a powered injector, the syringe comprising:
    a barrel comprising a distal end having an angled surface and defining an interior volume configured to receive a fluid, and a proximal end configured to be releasably connected to the powered injector; and
    a plunger comprising a substantially conical shape slideably disposed in the barrel,
    wherein at least a portion of a distal surface of the plunger is tinted a conspicuous color to reflect at least a portion of incident electromagnetic radiation off a surface of the syringe barrel toward the distal end of the barrel such that a reflected identification brightness pattern of the same conspicuous color is formed at a predetermined portion of the angled surface of the distal end of the barrel when the syringe is filled with the fluid.

12. The syringe of claim 11, wherein the reflected identification brightness pattern is indicative of at least one property of at least one of the syringe and the fluid.

13. The syringe of claim 12, wherein the reflected identification brightness pattern is not formed at the predetermined portion of the angled surface of the distal end of the barrel when the syringe is completely or partially filled with air.

14. The syringe of claim 11, wherein the angled surface of the distal end of the barrel is a tapered surface.

15. The syringe of claim 14, wherein the tapered surface of the distal end has a taper angle of about 30 degrees to about 60 degrees.

16. The syringe of claim 11, wherein the plunger comprises a plunger cover, wherein at least a portion of the plunger cover is tinted the conspicuous color.

17. The syringe of claim 11, wherein the conspicuous color is selected from the group consisting of red, green, orange, and yellow.

18. A method for identifying a property of a syringe or a fluid therein, the method comprising:
providing a syringe comprising:
a barrel comprising a distal end having an angled surface, wherein the barrel defines an interior volume configured to receive a fluid; and
a plunger slideably disposed in the barrel, wherein at least a portion of a distal surface of the plunger is tinted a conspicuous color;
exposing at least the portion of the distal surface of the plunger to electromagnetic radiation such that at least a portion of the electromagnetic radiation is reflected from the distal surface of the plunger to produce a reflected identification brightness pattern on a predetermined portion of the angled surface of the distal end of the barrel; and
determining at least one property of the syringe or the fluid based on the reflected identification brightness pattern.

19. The method of claim 18, wherein determining the at least one property of at least one of the syringe and the fluid comprises determining whether the syringe is completely or partially filled with air.

20. The method of claim 19, wherein determining whether the syringe is completely or partially filled with air comprises observing a presence or absence of the reflected identification brightness pattern having the conspicuous color on the predetermined portion of the angled surface of the distal end of the syringe.

21. The method of claim 20, wherein the reflected identification brightness pattern having the conspicuous color comprises a halo of the conspicuous color formed at the predetermined portion of the angled surface.

22. The method of claim 18, wherein the plunger comprises a plunger cover, wherein at least a portion of the plunger cover is tinted the conspicuous color.

23. The method of claim 18, wherein the conspicuous color is selected from the group consisting of red, green, orange, and yellow.

24. The method of claim 18, wherein an angle of the angled surface of the distal end of the barrel is from about 30 degrees to about 60 degrees.

25. A system for indicating whether a syringe is ready for use in injecting a fluid therein into a patient, the system comprising:
a syringe comprising:
a barrel comprising a distal end having an angled surface, wherein the barrel defines an interior volume configured to receive a fluid; and
a plunger slideably disposed in the barrel; and
an electromagnetic radiation source provided to direct incident electromagnetic radiation onto at least a portion of a distal surface of the plunger,
wherein at least the portion of the distal surface of the plunger is tinted a conspicuous color to reflect the incident electromagnetic radiation such that a reflected identification brightness pattern of the same conspicuous color is formed at a predetermined portion of the distal end of the barrel when the syringe is filled with the fluid, the reflected identification brightness pattern being indicative of at least one property of the syringe or the fluid.

26. The system of claim 25, wherein the electromagnetic radiation source comprises a light bulb, an LED bulb, a photon emitter, an infrared emitter, a laser, or ambient light.

27. The system of claim 25, wherein the plunger comprises a plunger cover, wherein at least a portion of the plunger cover is tinted the conspicuous color.

28. The system of claim 25, wherein the conspicuous color is selected from the group consisting of red, green, orange, and yellow.

29. The system of claim 25, wherein the angled surface of the distal end has a conical angle of about 30 degrees to about 60 degrees.

30. The system of claim 25, wherein the at least one property of at least one of the syringe and the fluid comprises that the syringe is completely or partially filled with air.

\* \* \* \* \*

UNITED STATES PATENT AND TRADEMARK OFFICE
CERTIFICATE OF CORRECTION

PATENT NO. : 10,039,889 B2
APPLICATION NO. : 15/634513
DATED : August 7, 2018
INVENTOR(S) : Cowan et al.

Page 1 of 1

It is certified that error appears in the above-identified patent and that said Letters Patent is hereby corrected as shown below:

In the Specification
In Column 24, Line 35, delete "view the" and insert -- view of the --, therefor.
In Column 34, Line 57, delete "display 116." and insert -- display 118. --, therefor.
In Column 44, Line 20, delete "display 116." and insert -- display 118. --, therefor.
In Column 47, Line 46, delete "syringe 114," and insert -- syringe 12, --, therefor.

In the Claims
In Column 54, Line 31, in Claim 6, delete "method" and insert -- syringe --, therefor.

Signed and Sealed this
Thirtieth Day of October, 2018

Andrei Iancu
*Director of the United States Patent and Trademark Office*